US008258114B2

(12) United States Patent
 Bhanot

(10) Patent No.: US 8,258,114 B2
(45) Date of Patent: Sep. 4, 2012

(54) MODULATION OF GLUCOSE-6-PHOSPHATASE TRANSLOCASE EXPRESSION

(75) Inventor: Sanjay Bhanot, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/045,187

(22) Filed: Mar. 10, 2011

(65) Prior Publication Data

US 2011/0166065 A1  Jul. 7, 2011

Related U.S. Application Data

(62) Division of application No. 11/111,288, filed on Apr. 20, 2005, now abandoned.

(60) Provisional application No. 60/564,641, filed on Apr. 21, 2004, provisional application No. 60/576,478, filed on Jun. 2, 2004, provisional application No. 60/615,395, filed on Sep. 30, 2004.

(51) Int. Cl.
 *A61K 31/70* (2006.01)
 *C07H 21/02* (2006.01)
 *C07H 21/04* (2006.01)

(52) U.S. Cl. ...... 514/44 A; 435/375; 435/377; 536/23.1; 536/24.1; 536/24.5

(58) Field of Classification Search ........................ None
 See application file for complete search history.

(56) References Cited

U.S. PATENT DOCUMENTS

| | | | |
|---|---|---|---|
| 5,593,840 | A | 1/1997 | Bhatnagar et al. |
| 5,801,154 | A | 9/1998 | Baracchini et al. |
| 5,985,558 | A | 11/1999 | Dean et al. |
| 6,582,908 | B2 | 6/2003 | Fodor et al. |
| 6,623,947 | B2 | 9/2003 | Chen |
| 7,250,289 | B2 | 7/2007 | Zhou |
| 2001/0053519 | A1 | 12/2001 | Fodor et al. |
| 2002/0037555 | A1 | 3/2002 | Chen |
| 2003/0228597 | A1 | 12/2003 | Cowsert et al. |
| 2004/0259175 | A1 | 12/2004 | Guo |
| 2005/0272080 | A1 | 12/2005 | Palma et al. |
| 2006/0003322 | A1 | 1/2006 | Bentwich |
| 2007/0031844 | A1 | 2/2007 | Khvorova et al. |

FOREIGN PATENT DOCUMENTS

| | | |
|---|---|---|
| WO | WO 02/092772 | 11/2002 |
| WO | WO 03/010139 | 2/2003 |
| WO | WO 03/011887 | 2/2003 |
| WO | WO 2004080406 | 9/2004 |

OTHER PUBLICATIONS

Belkaid et al., "Silencing of the human microsomal glucose-6 phosphate translocase" FEBS Letters (2006) 580(15):3746-3752.
Bernard-Helary et al., "Stable Transfection of cDNAs Targeting Specific Steps of Glycogen Metabolism Supports the Existance of Active Gluconeogenesis in Mouse Cultured Astrocytes" GLIA (2002) 37:379-382.
Brauer et al., "Evolutionary chemistry approach towad finding novel inhibitors fo the type 2 diabetes target glucose-6-phosphate translocase" Journal of Combinatorial Chemistry (2005) 7(2):218-226.
Branch et al., "A good antisense molecule is hard to find," TIBS (1998) 23:45-50.
Buck et al., "Design Strategies and Performance of Custom DNA Sequencing Primers" Biotechniques (1999) 27(3):526-538.
Caruthers et al., "Chemical Synthesis of Deoxyoligonucleotides by the Phosphoramidite Method" Methods in Enzymology (1987) 154:287-313.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Gerin et al., "Sequence of a putative glucose 6-phosphate translocase, mutated in glycogen storage disease type Ib" FEBS Lett. (1997) 419(2):235-238.
Goh et al., "Evidence for the expression of both the hydrolase and translocase components of hepatic glucose-6-phosphatase in murine pancreatic islets" Biochem. Biophys. Res. Commun. (2003) 307(4):935-941.
Gustafson et al., "Fatty Acid and Amino Acid Modulation of Glucose Cycling in Isolated Rat Hepatocytes" Biochem. J. (2001) 358:665-671.
Herling et al., "Alterations of Carbohydrate and Lipid Intermediary Metabolism During Inhibition of Glucose-6-phosphotase in Rats" European J. of Pharmacology (1999) 386:75-82.
Herling et al., "Prolonged blood glucose reduction in mrp-2 deficient rats (GY/TR<>) by the glucose-6-phosphate translocase inhibitors S 3025" Biochimica et Biophysica Acta—General Subjects (2002) 1569(1-3):105-110.
Kurukulasuriya et al., "Potential Drug Targets and Progress Towards Pharmacologic Inhibition of Hepatic Glucose Production" Current Medicinal Chemistry (2003) 10:123-153.
Liang et al., "Reduction in Glucagon Receptor Expression by an Antisense Oligonucleotide Ameliorates Diabetic Syndrome in db/db Mice" Diabetes (2004) 53:410-417.
Lin et al., "Cloning and characterization of cDNAs encoding a candidate glycogen storage disease type b1 protein in rodents" J. Biol. Chem. (1998) 273:31656-31660.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Sewell et al., "Phase 1 Trial of ISIS 104838, a 2'-Methoxyethyl Modified Antisense Oligonucleotide Targeting Tumor Necrosis Factor-Alpha" J. Pharmacology and Experimental Therapeutics (2002) 303:1334-1343.
Simon et al., "Upregulation of Hepatic Glucose 6-Phosphatase Gene Expression in Rats Treated with an Inhibitor of Glucose-6-phosphate Translocase" Archives of Biochemistry & Biophysics (2000) 373(2):418-428.
Vickers eta l., "Efficient Reduction of Target RNAs by Small Interfering RNA and Rnase H-dependent Antisense Agents" J. Biological Chem. (2003) 278(9):7108-7118.
European Supplementary Search Report for application EP 5779344.0 dated Apr. 10, 2008.
International Search Report for application PCT/US05/14116 dated Feb. 22, 2006.

*Primary Examiner* — Sean McGarry
(74) *Attorney, Agent, or Firm* — Isis Pharmaceuticals Patent Dept.; Jones Day

(57) ABSTRACT

Compositions and methods are provided for decreasing blood glucose levels in an animal, comprising administering to said animal an antisense inhibitor of glucose-6-phosphatase translocase expression alone or in combination with at least one glucose-lowering drug. Also provided are compositions and methods for treating diabetes and other metabolic disorders.

34 Claims, No Drawings

SEQUENCE LISTING

<160> NUMBER OF SEQ ID NOS: 341

<210> SEQ ID NO 1
<211> LENGTH: 2040
<212> TYPE: DNA
<213> ORGANISM: H. sapiens

<400> SEQUENCE: 1
caggcttaat gattgtccag aaggcggcta taaagggagc ctgggaggct gggtggagga      60
gggagcagaa aaaacccaac tcagcagatc tgggaactgt gagagcggca agcaggaact     120
gtggtcagag gctgtgcgtc ttggctggta gggcctgctc ttttctacca tggcagccca     180
gggctatggc tattatcgca ctgtgatctt ctcagccatg tttgggggct acagcctgta     240
ttacttcaat cgcaagacct tctcctttgt catgccatca ttggtggaag agatcccttt     300
ggacaaggat gatttggggt tcatcaccag cagccagtcg gcagcttatg ctatcagcaa     360 gttttgtcagt ggggtgctgt ctgaccagat gagtgctcgc tggctcttct cttctgggct     420
gctcctggtt ggcctggtca acatattctt tgcctggagc tccacagtac ctgtctttgc     480
tgccctctgg ttccttaatg gcctggccca ggggctgggc tggcccccat gtgggaaggt     540
cctgcggaag tggttttgagc catctcagtt tggcacttgg tgggccatcc tgtcaaccag     600

| | |
|---|---|
| catgaacctg gctggagggc tgggccctat cctggcaacc atccttgccc agagctacag | 660 |
| ctggcgcagc acgctggccc tatctggggc actgtgtgtg ttgtctcct tcctctgtct | 720 |
| cctgctcatc cacaatgaac ctgctgatgt tggactccgc aacctggacc ccatgccctc | 780 |
| tgagggcaag aagggctcct tgaaggagga gagcaccctg caggagctgc tgctgtcccc | 840 |
| ttacctgtgg gtgctctcca ctggttacct tgtggtgttt ggagtaaaga cctgctgtac | 900 |
| tgactggggc cagttcttcc ttatccagga gaaaggacag tcagcccttg taggtagctc | 960 |
| ctacatgagt gccctggaag ttgggggcct tgtaggcagc atcgcagctg gctacctgtc | 1020 |
| agaccgggcc atggcaaagg cgggactgtc caactacggg aaccctcgcc atggcctgtt | 1080 |
| gctgttcatg atggctggca tgacagtgtc catgtacctc ttccgggtaa cagtgaccag | 1140 |
| tgactccccc aagctctgga tcctggtatt gggagctgta tttggtttct cctcgtatgg | 1200 |
| ccccattgcc ctgtttggag tcatagccaa cgagagtgcc cctcccaact tgtgtggcac | 1260 |
| ctcccacgcc attgtgggac tcatggccaa tgtgggcggc tttctggctg gctgcccctt | 1320 |
| cagcaccatt gccaagcact acagttggag cacagccttc tgggtggctg aagtgatttg | 1380 |
| tgcggccagc acggctgcct tcttcctcct acgaaacatc cgcaccaaga tgggccgagt | 1440 |
| gtccaagaag gctgagtgaa gagagtccag gttccggagc accatcccac ggtggccttc | 1500 |
| cccctgcacg ctctgcgggg agaaaaggag gggcctgcct ggctagccct gaacctttca | 1560 |
| cttttccattt ctgcgccttt tctctcaccc gggtggcgct ggaagttatc agtggctagt | 1620 |
| gaggtcccag ctccctgatc ctatgctcta tttaaaagat aacctttggc cttagactcc | 1680 |
| gttagctcct atttcctgcc ttcagacaaa caggaaactt ctgcagtcag gaaggctcct | 1740 |
| gtacccttct tcttttccta ggccctgtcc tgcccgcatc ctaccccatc cccacctgaa | 1800 |
| gtgaggctat ccctgcagct gcagggcact aatgacccctt gacttctgct gggtcctaag | 1860 |
| tcctctcagc agtgggcgac tgctgttgcc aataccctcag actccaggga agagaggag | 1920 |
| gccatcattc tcactgtacc actaggcgca gttggatata ggtgggaaga aaaggtgact | 1980 |
| tgttatagaa gattaaaact agatttgata ctgaaaaaaa aaaaaaaaa aaaaaaaaa | 2040 |

<210> SEQ ID NO 2
<211> LENGTH: 2560
<212> TYPE: DNA
<213> ORGANISM: H. sapiens

<400> SEQUENCE: 2

| | |
|---|---|
| ggcacgaggg gccaccgagg cgctgtccct gaccaccagc acgagacccc tttctatcgc | 60 |
| gccagtcctg tggtctccgc acctctccag ctcctgcacc cccggccccc gtggttccca | 120 |
| gccgcacagt agcgtgtcct gggtagcgtg aggacccacg gggctgagca ggtgccacga | 180 |
| gcccgccgcc tcttcgccgc ccgccgcctc tcctcctctc ccgcccgccg cctggccctc | 240 |
| ccctaccagg ctgagcctct ggctgccaga agcgcgggc ctccgggaga atacgtgcgg | 300 |
| tcgcccgctc cgcgtgcgcc tacgccttct gctccagttg cttccccaat tgagcggaaa | 360 |
| agccggggca tgttgccggg gccctgggcg ggacggttgt gccctgcagc ccgaagcccg | 420 |
| ccggggcacc ttcccgccca cgagctgccc agtccctctg cttgcggccc ctgccaacgt | 480 |
| cccacaggac actgggtccc cttggagcct ccccaggctt aatgattgtc cagaaggcgg | 540 |
| ctataaaggg agcctgggag gctgggtgga ggagggagca gaaaaaccc aactcagcag | 600 |
| atctgggaac tgtgagagcg gcaagcagga actgtggtca gaggctgtgc gtcttggctg | 660 |
| gtagggcctg ctcttttcta ccatggcagc ccagggctat ggctattatc gcactgtgat | 720 |

-continued

| | |
|---|---|
| cttctcagcc atgtttgggg gctacagcct gtattacttc aatcgcaaga ccttctcctt | 780 |
| tgtcatgcca tcattggtgg aagagatccc tttggacaag gatgatttgg ggttcatcac | 840 |
| cagcagccag tcggcagctt atgctatcag caagtttgtc agtggggtgc tgtctgacca | 900 |
| gatgagtgct cgctggctct tctcttctgg gctgctcctg gttggcctgg tcaacatatt | 960 |
| ctttgcctgg agctccacag tacctgtctt tgctgccctc tggttcctta atggcctggc | 1020 |
| ccaggggctg gctggcccc catgtgggaa ggtcctgcgg aagtggtttg agccatctca | 1080 |
| gtttggcact tggtgggcca tcctgtcaac cagcatgaac ctggctggag gctgggccc | 1140 |
| tatcctggca accatccttg cccagagcta cagctggcgc agcacgctgg ccctatctgg | 1200 |
| ggcactgtgt gtggttgtct ccttcctctg tctcctgctc atccacaatg aacctgctga | 1260 |
| tgttggactc cgcaacctgg accccatgcc ctctgagggc aagaagggct ccttgaagga | 1320 |
| ggagagcacc ctgcaggagc tgctgctgtc cccttacctg tgggtgctct ccactggtta | 1380 |
| ccttgtggtg tttggagtaa agacctgctg tactgactgg ggccagttct tccttatcca | 1440 |
| ggagaaagga cagtcagccc ttgtaggtag ctcctacatg agtgccctgg aagttggggg | 1500 |
| ccttgtaggc agcatcgcag ctggctacct gtcagaccgg gccatggcaa aggcgggact | 1560 |
| gtccaactac gggaaccctc gccatggcct gttgctgttc atgatggctg gcatgacagt | 1620 |
| gtccatgtac ctcttccggg taacagtgac cagtgactcc cccaagctct ggatcctggt | 1680 |
| attgggagct gtatttggtt tctcctcgta tggccccatt gccctgtttg gagtcatagc | 1740 |
| caacgagagt gcccctccca acttgtgtgg cacctcccac gccattgtgg gactcatggc | 1800 |
| caatgtgggc ggctttctgg ctgggctgcc cttcagcacc attgccaagc actacagttg | 1860 |
| gagcacagcc ttctggtgg ctgaagtgat tgtgcggcc agcacggctg ccttcttcct | 1920 |
| cctacgaaac atccgcacca agatgggccg agtgtccaag aaggctgagt gaagagagtc | 1980 |
| caggttccgg agcaccatcc cacggtggcc ttcccctgc acgctctgcg gggagaaaag | 2040 |
| gagggcctg cctggctagc cctgaacctt tcactttca tttctgcgcc ttttctgtca | 2100 |
| cccgggtggc gctggaagtt atcagtggct agtgaggtcc cagctccctg atcctatgct | 2160 |
| ctatttaaaa gataaccttt ggccttagac tccgttagct cctatttcct gccttcagac | 2220 |
| aaacaggaaa cttctgcagt caggaaggct cctgtaccct tcttcttttc ctaggccctg | 2280 |
| tcctgcccgc atcctacccc atccccacct gaagtgaggc tatccctgca gctgcagggc | 2340 |
| actaatgacc cttgacttct gctgggtcct aagtcctctc agcagtgggt gactgctgtt | 2400 |
| gccaataccct cagactccag ggaaagagag gaggccatca ttctcactgt accactaggc | 2460 |
| gcagttggat ataggtggga agaaaaggtg acttgttata aagattaaa actagatttg | 2520 |
| atactgaaaa aaaaaaaaaa aaaaaaaaaa aaaaaaaaa | 2560 |

<210> SEQ ID NO 3
<211> LENGTH: 1923
<212> TYPE: DNA
<213> ORGANISM: M. musculus

<400> SEQUENCE: 3

| | |
|---|---|
| cacagaaaaa cacagctcag cagatccagg cactaaagag agctagctgc aagcaggagc | 60 |
| agtcaagagt ctgtggtcag aagtactgga gtgggccagc agggccagct ttttctacca | 120 |
| tggcagccca aggctacggc tactatcgca ctgtcatatt tgcggccatg tttggaggct | 180 |
| acagcctgta ctatttcaac cgcaaaacct tctcctttgt catgccctcc ttggtggatg | 240 |
| agatcgctct ggacaaggac gatttggggc tcatcacaag cagccagtcg gcagcctacg | 300 |

```
ccatcagcaa gtttgtgagc ggggttctgt cagaccagat gagcgcccgc tggctcttct    360
cctctgggct gctcctggtt ggtctggtca acgtagtctt ctcatggagc tccacagtgt    420
cagcctttgc tgctccttgg tttcttaatg gtctggcaca ggggctgggc tggccccct    480 gtgggaagat cctgaggaag tggtttgagc catcccagtt tggcacttgg tgggctgtgt    540
tgtcaaccag catgaacctg gctggaagtt tgggacctat cttggcaacg atcctcgccc    600
agagctacac ctggcgcagc acactggccc tgtctgggc actgtgtgtg gttgtctcct    660
tcttctgtct gctgctcatc acaatgaac ctgctgatgt tggactccga aatctggacc    720
ctctgccctc tgagggcaag aagggctcct tgaaggagga gagcacccta caggagctgc    780
tgctgtcccc ctatctctgg gtgctgtcca ctggctacct tgtggtcttc ggagtaaaga    840
cttgctgtac agactgggc cagttcttcc ttatccagga gagagggcag tccgcccttg    900
tgggtagctc ctacatcagt gccctcgagg tcggaggcct tgtaggaagc attgcagctg    960
gttacctgtc agacagggcc atggcgaagg cagggctgtc tctgtatggg aaccctcgcc   1020
acggcctatt gctactcatg atggctggga tggcagcatc cacgtatctc ttccgagtaa   1080
cggtgaccag tgactcaccc aagatctgga tcctggtttt gggagccgtg tttggtttct   1140
cttcttatgg tcccattgcc ttgtttggag tcatagccaa tgagagtgca cctcccaact   1200
tgtgtggaac ctctcatgct attgtgggac ttatggccaa tgtgggtgga tttctggctg   1260
gcttacccct cagcaccatt gccaagcact atagctggag cacagccttc tgggtggcag   1320
aagtggtttg tggagccagc acagttgtct tcttcttgct tcgaaatatc cgcaccaaga   1380
tgggccgagt atccaagaag ggagagtgaa tcgagtcctc gctatggagc atccccaact   1440
gcagccttac tggcaggaca cggaaaggag agcggctgct ctggctaaca cagaaccttt   1500
acgtttctgt gtctccactg tctctctgaa cctccatggt gctgcaagtt accagtggct   1560
aatgaggtcc caactcccat ccatgctct atttaaaatg atgacgtttg gttctagact   1620
ccatcagctt ctgtttctac cttctggcag acaggcaact cctgaattca gggtgtctcc   1680 tataccttc ttcttctcct aggtcctgat ctcctagtga gtattaatgg cctgtggttt   1740
ctgccgtacc ccaaggcttc ttggcagggg gcaaaattga tgccaatacc tcagtcccta   1800
agggaggaga ggagtccacc actctcatga ataccctggg acaaaaggga agaatataga   1860
gggcaaaccg acttgtatag atcgaataaa gctagatttg atacaaaaaa aaaaaaaaa   1920 aaa                                                                 1923

<210> SEQ ID NO 4
<211> LENGTH: 1930
<212> TYPE: DNA
<213> ORGANISM: R. norvegicus

<400> SEQUENCE: 4
aaaaacacag ctcagcagat ccgggcactg gagagggagc tgcaagcagg agcagtcaag     60
agtgtggtca gaagcaccgt gagtggacca gcagggccgg cttttctac catggcggcc    120 caaggctatg gctattaccg cactgtcata ttcacagcca tgttcggagg ctacagcctt    180
tactacttca accgcaaaac cttctctttt gtcatgccct ccttggtgga tgagatcgct    240
ctggacaagg acgatttggg gctcatcacg agcagccagt cggcagccta cgccatcagc    300
aagtttgtga gcggggtgct gtctgatcag atgagtgccc gttggctctt ctcctctggg    360
ctgctcctgg ttggtctggt caacgtagtc ttctcgtgga gctctacagt accggctttt    420
gctgctctct ggtttcttaa tggtctggca cagggctag gctggccccc ctgtgggaag    480
```

```
atcctgagga agtggtttga gccatcccag tttggtactt ggtgggctgt gttgtcaacc      540
agcatgaacc tggctggaag cctgggacct atcttggcga caatccttgc tcagagctac      600
agctggcgca gcaccctggc cctgtctggg tcactgtgtg tggttgtctc cttcttctgt      660
ctcctgctca tccacaacga acctgctgat gttggactcc gaaatctgga ccctcgcccc      720
tccaagggca aaagggctc gtcaaggag gagagcaccc tacaggacct gctgctgtcc        780
ccctatctct gggtgctctc cactggctac ctcgtggtct ttggggtaaa gacttgctgt      840
acagactggg gccagttctt ccttatccag gagagagggc agtcggccct tgtgggtagt      900
tcctacatca gtgccctaga ggttggaggc cttgtaggca gcattgcagc tggctatctg      960
tcagacaggg ctatggcaaa ggcagggctg tctgtgtatg gaaccctcg ccacagcctg      1020
ttgctgctca tgatggctgg catggcagca tccatgttcc tcttccgggt aacagtgacc     1080
agcgactctc ccaagatctg gatcctggta ttgggagctg tatttggttt ctcttcttat     1140
ggtcccattg ccttgtttgg agtcatagct aatgagagtg cacctcccaa cttgtgtggt     1200
acctctcatg ctattgtggg gctcatggcc aatgtgggtg gatttctggc tgggttaccc     1260
ttcagtacca tcgccaagca ctatagctgg agcacagcct tctgggtggc agaagtgatc     1320
tgtatagcca gcacagttgt cttcttcttg cttcgaaata tccgcaccaa gatgggccga     1380
gtatccaaga aggcagagtg aaaagagcac tcactataga gcatcccaa ctgcaacctc      1440
attggcagga cacagaaagg aagagaggct gctctggcta aacagagcc tttacatatc      1500
tgtgtctaca ctgtctctct ggacctccgt ggtgctgcaa gttaccagtg ctaatgagg      1560
tcctatgctc tatttaaatg atgtttggtt ttaggctcca ttggcttctg tttctacctt     1620
ctagcagaca gacaactcct aaattcaggg tgtctcctat acccctcttc ctctcctgag     1680
tccccatctc ctagtgaggt ggttctatct ctgcagctgc agaatattaa tggcctgtgg     1740
tttctgctgt accccaaggc ttcttgttag gggtcaacac tgttgccaat acctcagtcc     1800
ctaagggagg agaggaggcc accactctca tcagttacct ggggacaaaa gggaggaatg     1860
tagagagcaa actgtcttgt atagactaat aaaactagat ttgatactaa aaaaaaaaa      1920
aaaaaaaaa                                                              1930
```

<210> SEQ ID NO 5
<211> LENGTH: 20
<212> TYPE: DNA
<213> ORGANISM: Artificial Sequence
<220> FEATURE:
<223> OTHER INFORMATION: Oligomeric compound

<400> SEQUENCE: 5
cgtgtgtctg tgctagtccc                                                    20

<210> SEQ ID NO 6
<211> LENGTH: 20
<212> TYPE: DNA
<213> ORGANISM: Artificial Sequence
<220> FEATURE:
<223> OTHER INFORMATION: Oligomeric compound

<400> SEQUENCE: 6
ggcaacgtga acaggtccaa                                                    20

<210> SEQ ID NO 7
<211> LENGTH: 18
<212> TYPE: DNA
<213> ORGANISM: Artificial Sequence
<220> FEATURE:

```
<223> OTHER INFORMATION: Oligomeric compound

<400> SEQUENCE: 7
gcccattgct ggacatgc                                                  18

<210> SEQ ID NO 8
<211> LENGTH: 20
<212> TYPE: DNA
<213> ORGANISM: Artificial Sequence
<220> FEATURE:
<223> OTHER INFORMATION: Oligomeric compound

<400> SEQUENCE: 8
agcccattgc tggacatgca                                                20

<210> SEQ ID NO 9
<211> LENGTH: 20
<212> TYPE: DNA
<213> ORGANISM: Artificial Sequence
<220> FEATURE:
<223> OTHER INFORMATION: Oligomeric compound

<400> SEQUENCE: 9
ttgtcccagt cccaggcctc                                                20

<210> SEQ ID NO 10
<211> LENGTH: 20
<212> TYPE: DNA
<213> ORGANISM: Artificial Sequence
<220> FEATURE:
<223> OTHER INFORMATION: Oligomeric compound

<400> SEQUENCE: 10
ctttccgttg gacccctggg                                                20

<210> SEQ ID NO 11
<211> LENGTH: 20
<212> TYPE: DNA
<213> ORGANISM: Artificial Sequence
<220> FEATURE:
<223> OTHER INFORMATION: Oligomeric compound

<400> SEQUENCE: 11
gtgcgcgcga gcccgaaatc                                                20

<210> SEQ ID NO 12
<211> LENGTH: 20
<212> TYPE: DNA
<213> ORGANISM: Artificial Sequence
<220> FEATURE:
<223> OTHER INFORMATION: Oligomeric compound

<400> SEQUENCE: 12
atccaagtgc tactgtagta                                                20

<210> SEQ ID NO 13
<211> LENGTH: 20
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: 1-20
<223> OTHER INFORMATION: n = A,T,C or G

<400> SEQUENCE: 13
```
nnnnnnnnnn nnnnnnnnnn                                                    20

<210> SEQ ID NO 14
<211> LENGTH: 20
<212> TYPE: DNA
<213> ORGANISM: Artificial Sequence
<220> FEATURE:
<223> OTHER INFORMATION: Oligomeric compound

<400> SEQUENCE: 14
gccctccatg ctggcacagg                                                    20

<210> SEQ ID NO 15
<211> LENGTH: 20
<212> TYPE: DNA
<213> ORGANISM: Artificial Sequence
<220> FEATURE:
<223> OTHER INFORMATION: Oligomeric compound

<400> SEQUENCE: 15
agcaaaagat caatccgtta                                                    20

<210> SEQ ID NO 16
<211> LENGTH: 20
<212> TYPE: DNA
<213> ORGANISM: Artificial Sequence
<220> FEATURE:
<223> OTHER INFORMATION: Oligomeric compound

<400> SEQUENCE: 16
tacagaaggc tgggccttga                                                    20

<210> SEQ ID NO 17
<211> LENGTH: 20
<212> TYPE: DNA
<213> ORGANISM: Artificial Sequence
<220> FEATURE:
<223> OTHER INFORMATION: Oligomeric compound

<400> SEQUENCE: 17
atgcattctg cccccaagga                                                    20

<210> SEQ ID NO 18
<211> LENGTH: 19
<212> TYPE: DNA
<213> ORGANISM: Artificial Sequence
<220> FEATURE:
<223> OTHER INFORMATION: PCR primer

<400> SEQUENCE: 18
gaaggtgaag gtcggagtc                                                     19

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
gaagatggtg atgggatttc                                                    20

<210> SEQ ID NO 20
<211> LENGTH: 20
<212> TYPE: DNA
<213> ORGANISM: Artificial Sequence
<220> FEATURE:

<223> OTHER INFORMATION: PCR probe

<400> SEQUENCE: 20
caagcttccc gttctcagcc                                                                 20

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
ggcaaattca acggcacagt                                                                 20

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
gggtctcgct cctggaagat                                                                 20

<210> SEQ ID NO 23
<211> LENGTH: 27
<212> TYPE: DNA
<213> ORGANISM: Artificial Sequence
<220> FEATURE:
<223> OTHER INFORMATION: PCR probe

<400> SEQUENCE: 23
aaggccgaga atgggaagct tgtcatc                                                         27

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
gggcactgtg tgtggttgtc                                                                 20

<210> SEQ ID NO 25
<211> LENGTH: 22
<212> TYPE: DNA
<213> ORGANISM: Artificial Sequence
<220> FEATURE:
<223> OTHER INFORMATION: PCR primer

<400> SEQUENCE: 25
gagtccaaca tcagcaggtt ca                                                              22

<210> SEQ ID NO 26
<211> LENGTH: 27
<212> TYPE: DNA
<213> ORGANISM: Artificial Sequence
<220> FEATURE:
<223> OTHER INFORMATION: PCR probe

<400> SEQUENCE: 26
ccttcctctg tctcctgctc atccaca                                                         27

<210> SEQ ID NO 27

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 27
ggactctctt cactcagcct                                                     20

<210> SEQ ID NO 28
<211> LENGTH: 20
<212> TYPE: DNA
<213> ORGANISM: Artificial Sequence
<220> FEATURE:
<223> OTHER INFORMATION: Oligomeric compound

<400> SEQUENCE: 28
ggtgcggatg tttcgtagga                                                     20

<210> SEQ ID NO 29
<211> LENGTH: 20
<212> TYPE: DNA
<213> ORGANISM: Artificial Sequence
<220> FEATURE:
<223> OTHER INFORMATION: Oligomeric compound

<400> SEQUENCE: 29
gatgaacccc aaatcatcct                                                     20

<210> SEQ ID NO 30
<211> LENGTH: 20
<212> TYPE: DNA
<213> ORGANISM: Artificial Sequence
<220> FEATURE:
<223> OTHER INFORMATION: Oligomeric compound

<400> SEQUENCE: 30
cattagtgcc ctgcagctgc                                                     20

<210> SEQ ID NO 31
<211> LENGTH: 20
<212> TYPE: DNA
<213> ORGANISM: Artificial Sequence
<220> FEATURE:
<223> OTHER INFORMATION: Oligomeric compound

<400> SEQUENCE: 31
tgcgcctagt ggtacagtga                                                     20

<210> SEQ ID NO 32
<211> LENGTH: 20
<212> TYPE: DNA
<213> ORGANISM: Artificial Sequence
<220> FEATURE:
<223> OTHER INFORMATION: Oligomeric compound

<400> SEQUENCE: 32
aggcaaagaa tatgttgacc                                                     20

<210> SEQ ID NO 33
<211> LENGTH: 20
<212> TYPE: DNA
<213> ORGANISM: Artificial Sequence
<220> FEATURE:
<223> OTHER INFORMATION: Oligomeric compound

<400> SEQUENCE: 33
```

```
atggcgaggg ttcccgtagt                                            20

<210> SEQ ID NO 34
<211> LENGTH: 20
<212> TYPE: DNA
<213> ORGANISM: Artificial Sequence
<220> FEATURE:
<223> OTHER INFORMATION: Oligomeric compound

<400> SEQUENCE: 34
agatagggcc agcgtgctgc                                            20

<210> SEQ ID NO 35
<211> LENGTH: 20
<212> TYPE: DNA
<213> ORGANISM: Artificial Sequence
<220> FEATURE:
<223> OTHER INFORMATION: Oligomeric compound

<400> SEQUENCE: 35
taaccagtgg agagcaccca                                            20

<210> SEQ ID NO 36
<211> LENGTH: 20
<212> TYPE: DNA
<213> ORGANISM: Artificial Sequence
<220> FEATURE:
<223> OTHER INFORMATION: Oligomeric compound

<400> SEQUENCE: 36
tgactgtcct ttctcctgga                                            20

<210> SEQ ID NO 37
<211> LENGTH: 20
<212> TYPE: DNA
<213> ORGANISM: Artificial Sequence
<220> FEATURE:
<223> OTHER INFORMATION: Oligomeric compound

<400> SEQUENCE: 37
ctgtagcccc caaacatggc                                            20

<210> SEQ ID NO 38
<211> LENGTH: 20
<212> TYPE: DNA
<213> ORGANISM: Artificial Sequence
<220> FEATURE:
<223> OTHER INFORMATION: Oligomeric compound

<400> SEQUENCE: 38
gatagcctca cttcaggtgg                                            20

<210> SEQ ID NO 39
<211> LENGTH: 20
<212> TYPE: DNA
<213> ORGANISM: Artificial Sequence
<220> FEATURE:
<223> OTHER INFORMATION: Oligomeric compound

<400> SEQUENCE: 39
cacctatatc caactgcgcc                                            20

<210> SEQ ID NO 40
<211> LENGTH: 20
<212> TYPE: DNA
<213> ORGANISM: Artificial Sequence
<220> FEATURE:
```

<223> OTHER INFORMATION: Oligomeric compound

<400> SEQUENCE: 40
tgactgcaga agtttcctgt                    20

<210> SEQ ID NO 41
<211> LENGTH: 20
<212> TYPE: DNA
<213> ORGANISM: Artificial Sequence
<220> FEATURE:
<223> OTHER INFORMATION: Oligomeric compound

<400> SEQUENCE: 41
ccacctatat ccaactgcgc                    20

<210> SEQ ID NO 42
<211> LENGTH: 20
<212> TYPE: DNA
<213> ORGANISM: Artificial Sequence
<220> FEATURE:
<223> OTHER INFORMATION: Oligomeric compound

<400> SEQUENCE: 42
cagggcactc atgtaggagc                    20

<210> SEQ ID NO 43
<211> LENGTH: 20
<212> TYPE: DNA
<213> ORGANISM: Artificial Sequence
<220> FEATURE:
<223> OTHER INFORMATION: Oligomeric compound

<400> SEQUENCE: 43
tctcttccac caatgatggc                    20

<210> SEQ ID NO 44
<211> LENGTH: 20
<212> TYPE: DNA
<213> ORGANISM: Artificial Sequence
<220> FEATURE:
<223> OTHER INFORMATION: Oligomeric compound

<400> SEQUENCE: 44
tccttgtcca aagggatctc                    20

<210> SEQ ID NO 45
<211> LENGTH: 20
<212> TYPE: DNA
<213> ORGANISM: Artificial Sequence
<220> FEATURE:
<223> OTHER INFORMATION: Oligomeric compound

<400> SEQUENCE: 45
gctgcgccag ctgtagctct                    20

<210> SEQ ID NO 46
<211> LENGTH: 20
<212> TYPE: DNA
<213> ORGANISM: Artificial Sequence
<220> FEATURE:
<223> OTHER INFORMATION: Oligomeric compound

<400> SEQUENCE: 46
cctgcttgcc gctctcacag                    20

<210> SEQ ID NO 47

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 47
ttcctgcttg ccgctctcac                                              20

<210> SEQ ID NO 48
<211> LENGTH: 20
<212> TYPE: DNA
<213> ORGANISM: Artificial Sequence
<220> FEATURE:
<223> OTHER INFORMATION: Oligomeric compound

<400> SEQUENCE: 48
ggttgccagg atagggccca                                              20

<210> SEQ ID NO 49
<211> LENGTH: 20
<212> TYPE: DNA
<213> ORGANISM: Artificial Sequence
<220> FEATURE:
<223> OTHER INFORMATION: Oligomeric compound

<400> SEQUENCE: 49
cttggcaatg gtgctgaagg                                              20

<210> SEQ ID NO 50
<211> LENGTH: 20
<212> TYPE: DNA
<213> ORGANISM: Artificial Sequence
<220> FEATURE:
<223> OTHER INFORMATION: Oligomeric compound

<400> SEQUENCE: 50
tagtggtaca gtgagaatga                                              20

<210> SEQ ID NO 51
<211> LENGTH: 20
<212> TYPE: DNA
<213> ORGANISM: Artificial Sequence
<220> FEATURE:
<223> OTHER INFORMATION: Oligomeric compound

<400> SEQUENCE: 51
tgcctacaag gcccccaact                                              20

<210> SEQ ID NO 52
<211> LENGTH: 20
<212> TYPE: DNA
<213> ORGANISM: Artificial Sequence
<220> FEATURE:
<223> OTHER INFORMATION: Oligomeric compound

<400> SEQUENCE: 52
cccactgaca aacttgctga                                              20

<210> SEQ ID NO 53
<211> LENGTH: 20
<212> TYPE: DNA
<213> ORGANISM: Artificial Sequence
<220> FEATURE:
<223> OTHER INFORMATION: Oligomeric compound

<400> SEQUENCE: 53
```

-continued

```
cagttcccag atctgctgag                                          20

<210> SEQ ID NO 54
<211> LENGTH: 20
<212> TYPE: DNA
<213> ORGANISM: Artificial Sequence
<220> FEATURE:
<223> OTHER INFORMATION: Oligomeric compound

<400> SEQUENCE: 54
tgtcctttct cctggataag                                          20

<210> SEQ ID NO 55
<211> LENGTH: 20
<212> TYPE: DNA
<213> ORGANISM: Artificial Sequence
<220> FEATURE:
<223> OTHER INFORMATION: Oligomeric compound

<400> SEQUENCE: 55
aaccacacac agtgccccag                                          20

<210> SEQ ID NO 56
<211> LENGTH: 20
<212> TYPE: DNA
<213> ORGANISM: Artificial Sequence
<220> FEATURE:
<223> OTHER INFORMATION: Oligomeric compound

<400> SEQUENCE: 56
gtcaagggtc attagtgccc                                          20

<210> SEQ ID NO 57
<211> LENGTH: 20
<212> TYPE: DNA
<213> ORGANISM: Artificial Sequence
<220> FEATURE:
<223> OTHER INFORMATION: Oligomeric compound

<400> SEQUENCE: 57
agggtgctct cctccttcaa                                          20

<210> SEQ ID NO 58
<211> LENGTH: 20
<212> TYPE: DNA
<213> ORGANISM: Artificial Sequence
<220> FEATURE:
<223> OTHER INFORMATION: Oligomeric compound

<400> SEQUENCE: 58
cagttcctgc ttgccgctct                                          20

<210> SEQ ID NO 59
<211> LENGTH: 20
<212> TYPE: DNA
<213> ORGANISM: Artificial Sequence
<220> FEATURE:
<223> OTHER INFORMATION: Oligomeric compound

<400> SEQUENCE: 59
tgtttcgtag gaggaagaag                                          20

<210> SEQ ID NO 60
<211> LENGTH: 20
<212> TYPE: DNA
<213> ORGANISM: Artificial Sequence
<220> FEATURE:
```

<223> OTHER INFORMATION: Oligomeric compound

<400> SEQUENCE: 60
ccaggcaggc ccctcctttt                   20

<210> SEQ ID NO 61
<211> LENGTH: 20
<212> TYPE: DNA
<213> ORGANISM: Artificial Sequence
<220> FEATURE:
<223> OTHER INFORMATION: Oligomeric compound

<400> SEQUENCE: 61
gctgactgtc ctttctcctg                   20

<210> SEQ ID NO 62
<211> LENGTH: 19
<212> TYPE: RNA
<213> ORGANISM: Artificial Sequence
<220> FEATURE:
<223> OTHER INFORMATION: Oligomeric compound

<400> SEQUENCE: 62
cgagaggcgg acgggaccg                    19

<210> SEQ ID NO 63
<211> LENGTH: 21
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: (1)...(19)
<223> OTHER INFORMATION: bases at these positions are RNA

<400> SEQUENCE: 63
cgagaggcgg acgggaccgt t                 21

<210> SEQ ID NO 64
<211> LENGTH: 21
<212> TYPE: DNA
<213> ORGANISM: Artificial Sequence
<220> FEATURE:
<223> OTHER INFORMATION: Oligomeric compound
<220> FEATURE:
<221> NAME/KEY: misc_feature
<222> LOCATION: (3)...(21)
<223> OTHER INFORMATION: bases at these positions are RNA

<400> SEQUENCE: 64
ttgctctccg cctgccctgg c                 21

<210> SEQ ID NO 65
<211> LENGTH: 19
<212> TYPE: RNA
<213> ORGANISM: Artificial Sequence
<220> FEATURE:
<223> OTHER INFORMATION: Oligomeric compound

<400> SEQUENCE: 65
gcucuccgcc ugcccuggc                    19

<210> SEQ ID NO 66
<211> LENGTH: 22
<212> TYPE: DNA
<213> ORGANISM: Artificial Sequence
<220> FEATURE:

<223> OTHER INFORMATION: PCR primer

<400> SEQUENCE: 66
gaaggcaggg ctgtctctgt at                22

<210> SEQ ID NO 67
<211> LENGTH: 19
<212> TYPE: DNA
<213> ORGANISM: Artificial Sequence
<220> FEATURE:
<223> OTHER INFORMATION: PCR primer

<400> SEQUENCE: 67
ccatcccagc catcatgag                    19

<210> SEQ ID NO 68
<211> LENGTH: 22
<212> TYPE: DNA
<213> ORGANISM: Artificial Sequence
<220> FEATURE:
<223> OTHER INFORMATION: PCR probe

<400> SEQUENCE: 68
aaccctcgcc acggcctatt gc                22

<210> SEQ ID NO 69
<211> LENGTH: 20
<212> TYPE: DNA
<213> ORGANISM: Artificial Sequence
<220> FEATURE:
<223> OTHER INFORMATION: Oligomeric compound

<400> SEQUENCE: 69
tgcctggatc tgctgagctg                   20

<210> SEQ ID NO 70
<211> LENGTH: 20
<212> TYPE: DNA
<213> ORGANISM: Artificial Sequence
<220> FEATURE:
<223> OTHER INFORMATION: Oligomeric compound

<400> SEQUENCE: 70
tctctttagt gcctggatct                   20

<210> SEQ ID NO 71
<211> LENGTH: 20
<212> TYPE: DNA
<213> ORGANISM: Artificial Sequence
<220> FEATURE:
<223> OTHER INFORMATION: Oligomeric compound

<400> SEQUENCE: 71
gactgctcct gcttgcagct                   20

<210> SEQ ID NO 72
<211> LENGTH: 20
<212> TYPE: DNA
<213> ORGANISM: Artificial Sequence
<220> FEATURE:
<223> OTHER INFORMATION: Oligomeric compound

<400> SEQUENCE: 72
cacagactct tgactgctcc                   20

<210> SEQ ID NO 73

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 73
ctgctggccc actccagtac                                               20

<210> SEQ ID NO 74
<211> LENGTH: 20
<212> TYPE: DNA
<213> ORGANISM: Artificial Sequence
<220> FEATURE:
<223> OTHER INFORMATION: Oligomeric compound

<400> SEQUENCE: 74
ccgtagcctt gggctgccat                                               20

<210> SEQ ID NO 75
<211> LENGTH: 20
<212> TYPE: DNA
<213> ORGANISM: Artificial Sequence
<220> FEATURE:
<223> OTHER INFORMATION: Oligomeric compound

<400> SEQUENCE: 75
gccgcaaata tgacagtgcg                                               20

<210> SEQ ID NO 76
<211> LENGTH: 20
<212> TYPE: DNA
<213> ORGANISM: Artificial Sequence
<220> FEATURE:
<223> OTHER INFORMATION: Oligomeric compound

<400> SEQUENCE: 76
acaaaggaga aggttttgcg                                               20

<210> SEQ ID NO 77
<211> LENGTH: 20
<212> TYPE: DNA
<213> ORGANISM: Artificial Sequence
<220> FEATURE:
<223> OTHER INFORMATION: Oligomeric compound

<400> SEQUENCE: 77
cagagcgatc tcatccacca                                               20

<210> SEQ ID NO 78
<211> LENGTH: 20
<212> TYPE: DNA
<213> ORGANISM: Artificial Sequence
<220> FEATURE:
<223> OTHER INFORMATION: Oligomeric compound

<400> SEQUENCE: 78
cttgtccaga gcgatctcat                                               20

<210> SEQ ID NO 79
<211> LENGTH: 20
<212> TYPE: DNA
<213> ORGANISM: Artificial Sequence
<220> FEATURE:
<223> OTHER INFORMATION: Oligomeric compound

<400> SEQUENCE: 79
```
tcgtccttgt ccagagcgat                    20

<210> SEQ ID NO 80
<211> LENGTH: 20
<212> TYPE: DNA
<213> ORGANISM: Artificial Sequence
<220> FEATURE:
<223> OTHER INFORMATION: Oligomeric compound

<400> SEQUENCE: 80
gagccccaaa tcgtccttgt                    20

<210> SEQ ID NO 81
<211> LENGTH: 20
<212> TYPE: DNA
<213> ORGANISM: Artificial Sequence
<220> FEATURE:
<223> OTHER INFORMATION: Oligomeric compound

<400> SEQUENCE: 81
gtgatgagcc ccaaatcgtc                    20

<210> SEQ ID NO 82
<211> LENGTH: 20
<212> TYPE: DNA
<213> ORGANISM: Artificial Sequence
<220> FEATURE:
<223> OTHER INFORMATION: Oligomeric compound

<400> SEQUENCE: 82
ggctgcttgt gatgagcccc                    20

<210> SEQ ID NO 83
<211> LENGTH: 20
<212> TYPE: DNA
<213> ORGANISM: Artificial Sequence
<220> FEATURE:
<223> OTHER INFORMATION: Oligomeric compound

<400> SEQUENCE: 83
ctgatggcgt aggctgccga                    20

<210> SEQ ID NO 84
<211> LENGTH: 20
<212> TYPE: DNA
<213> ORGANISM: Artificial Sequence
<220> FEATURE:
<223> OTHER INFORMATION: Oligomeric compound

<400> SEQUENCE: 84
gctcacaaac ttgctgatgg                    20

<210> SEQ ID NO 85
<211> LENGTH: 20
<212> TYPE: DNA
<213> ORGANISM: Artificial Sequence
<220> FEATURE:
<223> OTHER INFORMATION: Oligomeric compound

<400> SEQUENCE: 85
ccattaagaa accaaggagc                    20

<210> SEQ ID NO 86
<211> LENGTH: 20
<212> TYPE: DNA
<213> ORGANISM: Artificial Sequence
<220> FEATURE:

```
<223> OTHER INFORMATION: Oligomeric compound

<400> SEQUENCE: 86
agcccctgtg ccagaccatt                                              20

<210> SEQ ID NO 87
<211> LENGTH: 20
<212> TYPE: DNA
<213> ORGANISM: Artificial Sequence
<220> FEATURE:
<223> OTHER INFORMATION: Oligomeric compound

<400> SEQUENCE: 87
ccaaactggg atggctcaaa                                              20

<210> SEQ ID NO 88
<211> LENGTH: 20
<212> TYPE: DNA
<213> ORGANISM: Artificial Sequence
<220> FEATURE:
<223> OTHER INFORMATION: Oligomeric compound

<400> SEQUENCE: 88
tcatgctggt tgacaacaca                                              20

<210> SEQ ID NO 89
<211> LENGTH: 20
<212> TYPE: DNA
<213> ORGANISM: Artificial Sequence
<220> FEATURE:
<223> OTHER INFORMATION: Oligomeric compound

<400> SEQUENCE: 89
ccaaacttcc agccaggttc                                              20

<210> SEQ ID NO 90
<211> LENGTH: 20
<212> TYPE: DNA
<213> ORGANISM: Artificial Sequence
<220> FEATURE:
<223> OTHER INFORMATION: Oligomeric compound

<400> SEQUENCE: 90
gccagtgtgc tgcgccagct                                              20

<210> SEQ ID NO 91
<211> LENGTH: 20
<212> TYPE: DNA
<213> ORGANISM: Artificial Sequence
<220> FEATURE:
<223> OTHER INFORMATION: Oligomeric compound

<400> SEQUENCE: 91
acagggccag tgtgctgcgc                                              20

<210> SEQ ID NO 92
<211> LENGTH: 20
<212> TYPE: DNA
<213> ORGANISM: Artificial Sequence
<220> FEATURE:
<223> OTHER INFORMATION: Oligomeric compound

<400> SEQUENCE: 92
cagagggtcc agatttcgga                                              20

<210> SEQ ID NO 93
```

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 93
ccagtggaca gcacccagag                                               20

<210> SEQ ID NO 94
<211> LENGTH: 20
<212> TYPE: DNA
<213> ORGANISM: Artificial Sequence
<220> FEATURE:
<223> OTHER INFORMATION: Oligomeric compound

<400> SEQUENCE: 94
agaccacaag gtagccagtg                                               20

<210> SEQ ID NO 95
<211> LENGTH: 20
<212> TYPE: DNA
<213> ORGANISM: Artificial Sequence
<220> FEATURE:
<223> OTHER INFORMATION: Oligomeric compound

<400> SEQUENCE: 95
tacagcaagt ctttactccg                                               20

<210> SEQ ID NO 96
<211> LENGTH: 20
<212> TYPE: DNA
<213> ORGANISM: Artificial Sequence
<220> FEATURE:
<223> OTHER INFORMATION: Oligomeric compound

<400> SEQUENCE: 96
gccccagtct gtacagcaag                                               20

<210> SEQ ID NO 97
<211> LENGTH: 20
<212> TYPE: DNA
<213> ORGANISM: Artificial Sequence
<220> FEATURE:
<223> OTHER INFORMATION: Oligomeric compound

<400> SEQUENCE: 97
acccacaagg gcggactgcc                                               20

<210> SEQ ID NO 98
<211> LENGTH: 20
<212> TYPE: DNA
<213> ORGANISM: Artificial Sequence
<220> FEATURE:
<223> OTHER INFORMATION: Oligomeric compound

<400> SEQUENCE: 98
gagctaccca caagggcgga                                               20

<210> SEQ ID NO 99
<211> LENGTH: 20
<212> TYPE: DNA
<213> ORGANISM: Artificial Sequence
<220> FEATURE:
<223> OTHER INFORMATION: Oligomeric compound

<400> SEQUENCE: 99
```

```
ggcactgatg taggagctac                                                   20

<210> SEQ ID NO 100
<211> LENGTH: 20
<212> TYPE: DNA
<213> ORGANISM: Artificial Sequence
<220> FEATURE:
<223> OTHER INFORMATION: Oligomeric compound

<400> SEQUENCE: 100
aaggcctccg acctcgaggg                                                   20

<210> SEQ ID NO 101
<211> LENGTH: 20
<212> TYPE: DNA
<213> ORGANISM: Artificial Sequence
<220> FEATURE:
<223> OTHER INFORMATION: Oligomeric compound

<400> SEQUENCE: 101
aatgcttcct acaaggcctc                                                   20

<210> SEQ ID NO 102
<211> LENGTH: 20
<212> TYPE: DNA
<213> ORGANISM: Artificial Sequence
<220> FEATURE:
<223> OTHER INFORMATION: Oligomeric compound

<400> SEQUENCE: 102
cgccatggcc ctgtctgaca                                                   20

<210> SEQ ID NO 103
<211> LENGTH: 20
<212> TYPE: DNA
<213> ORGANISM: Artificial Sequence
<220> FEATURE:
<223> OTHER INFORMATION: Oligomeric compound

<400> SEQUENCE: 103
acagagacag ccctgccttc                                                   20

<210> SEQ ID NO 104
<211> LENGTH: 20
<212> TYPE: DNA
<213> ORGANISM: Artificial Sequence
<220> FEATURE:
<223> OTHER INFORMATION: Oligomeric compound

<400> SEQUENCE: 104
cgagggttcc catacagaga                                                   20

<210> SEQ ID NO 105
<211> LENGTH: 20
<212> TYPE: DNA
<213> ORGANISM: Artificial Sequence
<220> FEATURE:
<223> OTHER INFORMATION: Oligomeric compound

<400> SEQUENCE: 105
ataggccgtg gcgagggttc                                                   20

<210> SEQ ID NO 106
<211> LENGTH: 20
<212> TYPE: DNA
<213> ORGANISM: Artificial Sequence
<220> FEATURE:
```

```
<223> OTHER INFORMATION: Oligomeric compound

<400> SEQUENCE: 106
agccatcatg agtagcaata                                               20

<210> SEQ ID NO 107
<211> LENGTH: 20
<212> TYPE: DNA
<213> ORGANISM: Artificial Sequence
<220> FEATURE:
<223> OTHER INFORMATION: Oligomeric compound

<400> SEQUENCE: 107
tactcggaag agatacgtgg                                               20

<210> SEQ ID NO 108
<211> LENGTH: 20
<212> TYPE: DNA
<213> ORGANISM: Artificial Sequence
<220> FEATURE:
<223> OTHER INFORMATION: Oligomeric compound

<400> SEQUENCE: 108
atcttgggtg agtcactggt                                               20

<210> SEQ ID NO 109
<211> LENGTH: 20
<212> TYPE: DNA
<213> ORGANISM: Artificial Sequence
<220> FEATURE:
<223> OTHER INFORMATION: Oligomeric compound

<400> SEQUENCE: 109
aaccaggatc cagatcttgg                                               20

<210> SEQ ID NO 110
<211> LENGTH: 20
<212> TYPE: DNA
<213> ORGANISM: Artificial Sequence
<220> FEATURE:
<223> OTHER INFORMATION: Oligomeric compound

<400> SEQUENCE: 110
cacggctccc aaaaccagga                                               20

<210> SEQ ID NO 111
<211> LENGTH: 20
<212> TYPE: DNA
<213> ORGANISM: Artificial Sequence
<220> FEATURE:
<223> OTHER INFORMATION: Oligomeric compound

<400> SEQUENCE: 111
gaggttccac acaagttggg                                               20

<210> SEQ ID NO 112
<211> LENGTH: 20
<212> TYPE: DNA
<213> ORGANISM: Artificial Sequence
<220> FEATURE:
<223> OTHER INFORMATION: Oligomeric compound

<400> SEQUENCE: 112
atgagaggtt ccacacaagt                                               20

<210> SEQ ID NO 113
```

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 113
gctgaagggt aagccagcca                                                    20

<210> SEQ ID NO 114
<211> LENGTH: 20
<212> TYPE: DNA
<213> ORGANISM: Artificial Sequence
<220> FEATURE:
<223> OTHER INFORMATION: Oligomeric compound

<400> SEQUENCE: 114
tgtgctccag ctatagtgct                                                    20

<210> SEQ ID NO 115
<211> LENGTH: 20
<212> TYPE: DNA
<213> ORGANISM: Artificial Sequence
<220> FEATURE:
<223> OTHER INFORMATION: Oligomeric compound

<400> SEQUENCE: 115
acaactgtgc tggctccaca                                                    20

<210> SEQ ID NO 116
<211> LENGTH: 20
<212> TYPE: DNA
<213> ORGANISM: Artificial Sequence
<220> FEATURE:
<223> OTHER INFORMATION: Oligomeric compound

<400> SEQUENCE: 116
ggatatttcg aagcaagaag                                                    20

<210> SEQ ID NO 117
<211> LENGTH: 20
<212> TYPE: DNA
<213> ORGANISM: Artificial Sequence
<220> FEATURE:
<223> OTHER INFORMATION: Oligomeric compound

<400> SEQUENCE: 117
tcactctccc ttcttggata                                                    20

<210> SEQ ID NO 118
<211> LENGTH: 20
<212> TYPE: DNA
<213> ORGANISM: Artificial Sequence
<220> FEATURE:
<223> OTHER INFORMATION: Oligomeric compound

<400> SEQUENCE: 118
gctccatagc gaggactcga                                                    20

<210> SEQ ID NO 119
<211> LENGTH: 20
<212> TYPE: DNA
<213> ORGANISM: Artificial Sequence
<220> FEATURE:
<223> OTHER INFORMATION: Oligomeric compound

<400> SEQUENCE: 119
```

```
ccgtgtcctg ccagtaaggc                                              20

<210> SEQ ID NO 120
<211> LENGTH: 20
<212> TYPE: DNA
<213> ORGANISM: Artificial Sequence
<220> FEATURE:
<223> OTHER INFORMATION: Oligomeric compound

<400> SEQUENCE: 120
ctttccgtgt cctgccagta                                              20

<210> SEQ ID NO 121
<211> LENGTH: 20
<212> TYPE: DNA
<213> ORGANISM: Artificial Sequence
<220> FEATURE:
<223> OTHER INFORMATION: Oligomeric compound

<400> SEQUENCE: 121
gcagccgctc tcctttccgt                                              20

<210> SEQ ID NO 122
<211> LENGTH: 20
<212> TYPE: DNA
<213> ORGANISM: Artificial Sequence
<220> FEATURE:
<223> OTHER INFORMATION: Oligomeric compound

<400> SEQUENCE: 122
aggttctgtg ttagccagag                                              20

<210> SEQ ID NO 123
<211> LENGTH: 20
<212> TYPE: DNA
<213> ORGANISM: Artificial Sequence
<220> FEATURE:
<223> OTHER INFORMATION: Oligomeric compound

<400> SEQUENCE: 123
aaacgtaaag gttctgtgtt                                              20

<210> SEQ ID NO 124
<211> LENGTH: 20
<212> TYPE: DNA
<213> ORGANISM: Artificial Sequence
<220> FEATURE:
<223> OTHER INFORMATION: Oligomeric compound

<400> SEQUENCE: 124
cacagaaacg taaaggttct                                              20

<210> SEQ ID NO 125
<211> LENGTH: 20
<212> TYPE: DNA
<213> ORGANISM: Artificial Sequence
<220> FEATURE:
<223> OTHER INFORMATION: Oligomeric compound

<400> SEQUENCE: 125
gtggagacac agaaacgtaa                                              20

<210> SEQ ID NO 126
<211> LENGTH: 20
<212> TYPE: DNA
<213> ORGANISM: Artificial Sequence
<220> FEATURE:
```

```
<223> OTHER INFORMATION: Oligomeric compound

<400> SEQUENCE: 126
gggacctcat tagccactgg                                               20

<210> SEQ ID NO 127
<211> LENGTH: 20
<212> TYPE: DNA
<213> ORGANISM: Artificial Sequence
<220> FEATURE:
<223> OTHER INFORMATION: Oligomeric compound

<400> SEQUENCE: 127
cgtcatcatt ttaaatagag                                               20

<210> SEQ ID NO 128
<211> LENGTH: 20
<212> TYPE: DNA
<213> ORGANISM: Artificial Sequence
<220> FEATURE:
<223> OTHER INFORMATION: Oligomeric compound

<400> SEQUENCE: 128
atggagtcta gaaccaaacg                                               20

<210> SEQ ID NO 129
<211> LENGTH: 20
<212> TYPE: DNA
<213> ORGANISM: Artificial Sequence
<220> FEATURE:
<223> OTHER INFORMATION: Oligomeric compound

<400> SEQUENCE: 129
tataggagac accctgaatt                                               20

<210> SEQ ID NO 130
<211> LENGTH: 20
<212> TYPE: DNA
<213> ORGANISM: Artificial Sequence
<220> FEATURE:
<223> OTHER INFORMATION: Oligomeric compound

<400> SEQUENCE: 130
gaagggtata ggagacaccc                                               20

<210> SEQ ID NO 131
<211> LENGTH: 20
<212> TYPE: DNA
<213> ORGANISM: Artificial Sequence
<220> FEATURE:
<223> OTHER INFORMATION: Oligomeric compound

<400> SEQUENCE: 131
cctaggagaa gaagaagggt                                               20

<210> SEQ ID NO 132
<211> LENGTH: 20
<212> TYPE: DNA
<213> ORGANISM: Artificial Sequence
<220> FEATURE:
<223> OTHER INFORMATION: Oligomeric compound

<400> SEQUENCE: 132
ccacaggcca ttaatactca                                               20

<210> SEQ ID NO 133
```

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 133
ggcagaaacc acaggccatt                                               20

<210> SEQ ID NO 134
<211> LENGTH: 20
<212> TYPE: DNA
<213> ORGANISM: Artificial Sequence
<220> FEATURE:
<223> OTHER INFORMATION: Oligomeric compound

<400> SEQUENCE: 134
gggtacggca gaaaccacag                                               20

<210> SEQ ID NO 135
<211> LENGTH: 20
<212> TYPE: DNA
<213> ORGANISM: Artificial Sequence
<220> FEATURE:
<223> OTHER INFORMATION: Oligomeric compound

<400> SEQUENCE: 135
tattggcatc aattttgccc                                               20

<210> SEQ ID NO 136
<211> LENGTH: 20
<212> TYPE: DNA
<213> ORGANISM: Artificial Sequence
<220> FEATURE:
<223> OTHER INFORMATION: Oligomeric compound

<400> SEQUENCE: 136
gggactgagg tattggcatc                                               20

<210> SEQ ID NO 137
<211> LENGTH: 20
<212> TYPE: DNA
<213> ORGANISM: Artificial Sequence
<220> FEATURE:
<223> OTHER INFORMATION: Oligomeric compound

<400> SEQUENCE: 137
tcctctcctc ccttagggac                                               20

<210> SEQ ID NO 138
<211> LENGTH: 20
<212> TYPE: DNA
<213> ORGANISM: Artificial Sequence
<220> FEATURE:
<223> OTHER INFORMATION: Oligomeric compound

<400> SEQUENCE: 138
tcatgagagt ggtggactcc                                               20

<210> SEQ ID NO 139
<211> LENGTH: 20
<212> TYPE: DNA
<213> ORGANISM: Artificial Sequence
<220> FEATURE:
<223> OTHER INFORMATION: Oligomeric compound

<400> SEQUENCE: 139
```
agggtattca tgagagtggt                                              20

<210> SEQ ID NO 140
<211> LENGTH: 20
<212> TYPE: DNA
<213> ORGANISM: Artificial Sequence
<220> FEATURE:
<223> OTHER INFORMATION: Oligomeric compound

<400> SEQUENCE: 140
aagtcggttt gccctctata                                              20

<210> SEQ ID NO 141
<211> LENGTH: 20
<212> TYPE: DNA
<213> ORGANISM: Artificial Sequence
<220> FEATURE:
<223> OTHER INFORMATION: Oligomeric compound

<400> SEQUENCE: 141
tatacaagtc ggtttgccct                                              20

<210> SEQ ID NO 142
<211> LENGTH: 20
<212> TYPE: DNA
<213> ORGANISM: Artificial Sequence
<220> FEATURE:
<223> OTHER INFORMATION: Oligomeric compound

<400> SEQUENCE: 142
gctttattcg atctatacaa                                              20

<210> SEQ ID NO 143
<211> LENGTH: 20
<212> TYPE: DNA
<213> ORGANISM: Artificial Sequence
<220> FEATURE:
<223> OTHER INFORMATION: Oligomeric compound

<400> SEQUENCE: 143
ctgctagcct ctggatttga                                              20

<210> SEQ ID NO 144
<211> LENGTH: 20
<212> TYPE: DNA
<213> ORGANISM: Artificial Sequence
<220> FEATURE:
<223> OTHER INFORMATION: Oligomeric compound

<400> SEQUENCE: 144
ccttccctga aggttcctcc                                              20

<210> SEQ ID NO 145
<211> LENGTH: 20
<212> TYPE: DNA
<213> ORGANISM: Artificial Sequence
<220> FEATURE:
<223> OTHER INFORMATION: Oligomeric compound

<400> SEQUENCE: 145
tgggctgcca tggtagaaaa                                              20

<210> SEQ ID NO 146
<211> LENGTH: 20
<212> TYPE: DNA
<213> ORGANISM: Artificial Sequence
<220> FEATURE:

<223> OTHER INFORMATION: Oligomeric compound

<400> SEQUENCE: 146
ggcatgacaa aggagaaggt                                           20

<210> SEQ ID NO 147
<211> LENGTH: 20
<212> TYPE: DNA
<213> ORGANISM: Artificial Sequence
<220> FEATURE:
<223> OTHER INFORMATION: Oligomeric compound

<400> SEQUENCE: 147
gcccaccaag tgccaaactg                                           20

<210> SEQ ID NO 148
<211> LENGTH: 20
<212> TYPE: DNA
<213> ORGANISM: Artificial Sequence
<220> FEATURE:
<223> OTHER INFORMATION: Oligomeric compound

<400> SEQUENCE: 148
caggttcatg ctggttgaca                                           20

<210> SEQ ID NO 149
<211> LENGTH: 20
<212> TYPE: DNA
<213> ORGANISM: Artificial Sequence
<220> FEATURE:
<223> OTHER INFORMATION: Oligomeric compound

<400> SEQUENCE: 149
cgccagctgt agctctgggc                                           20

<210> SEQ ID NO 150
<211> LENGTH: 20
<212> TYPE: DNA
<213> ORGANISM: Artificial Sequence
<220> FEATURE:
<223> OTHER INFORMATION: Oligomeric compound

<400> SEQUENCE: 150
ctgcgccagc tgtagctctg                                           20

<210> SEQ ID NO 151
<211> LENGTH: 20
<212> TYPE: DNA
<213> ORGANISM: Artificial Sequence
<220> FEATURE:
<223> OTHER INFORMATION: Oligomeric compound

<400> SEQUENCE: 151
accacacaca gtgccccaga                                           20

<210> SEQ ID NO 152
<211> LENGTH: 20
<212> TYPE: DNA
<213> ORGANISM: Artificial Sequence
<220> FEATURE:
<223> OTHER INFORMATION: Oligomeric compound

<400> SEQUENCE: 152
ggagacaacc acacacagtg                                           20

<210> SEQ ID NO 153

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 153
ggttcattgt ggatgagcag                                              20

<210> SEQ ID NO 154
<211> LENGTH: 20
<212> TYPE: DNA
<213> ORGANISM: Artificial Sequence
<220> FEATURE:
<223> OTHER INFORMATION: Oligomeric compound

<400> SEQUENCE: 154
aggaagaact ggccccagtc                                              20

<210> SEQ ID NO 155
<211> LENGTH: 20
<212> TYPE: DNA
<213> ORGANISM: Artificial Sequence
<220> FEATURE:
<223> OTHER INFORMATION: Oligomeric compound

<400> SEQUENCE: 155
ggataaggaa gaactggccc                                              20

<210> SEQ ID NO 156
<211> LENGTH: 20
<212> TYPE: DNA
<213> ORGANISM: Artificial Sequence
<220> FEATURE:
<223> OTHER INFORMATION: Oligomeric compound

<400> SEQUENCE: 156
ttggcaatgg tgctgaaggg                                              20

<210> SEQ ID NO 157
<211> LENGTH: 20
<212> TYPE: DNA
<213> ORGANISM: Artificial Sequence
<220> FEATURE:
<223> OTHER INFORMATION: Oligomeric compound

<400> SEQUENCE: 157
acccagaagg ctgtgctcca                                              20

<210> SEQ ID NO 158
<211> LENGTH: 20
<212> TYPE: DNA
<213> ORGANISM: Artificial Sequence
<220> FEATURE:
<223> OTHER INFORMATION: Oligomeric compound

<400> SEQUENCE: 158
cggcccatct tggtgcggat                                              20

<210> SEQ ID NO 159
<211> LENGTH: 20
<212> TYPE: DNA
<213> ORGANISM: Artificial Sequence
<220> FEATURE:
<223> OTHER INFORMATION: Oligomeric compound

<400> SEQUENCE: 159
```

-continued

| | |
|---|---|
| ccaggagcag cccagaagag | 20 |

<210> SEQ ID NO 160
<211> LENGTH: 20
<212> TYPE: DNA
<213> ORGANISM: Artificial Sequence
<220> FEATURE:
<223> OTHER INFORMATION: Oligomeric compound

<400> SEQUENCE: 160

| | |
|---|---|
| ccaaccagga gcagcccaga | 20 |

<210> SEQ ID NO 161
<211> LENGTH: 20
<212> TYPE: DNA
<213> ORGANISM: Artificial Sequence
<220> FEATURE:
<223> OTHER INFORMATION: Oligomeric compound

<400> SEQUENCE: 161

| | |
|---|---|
| caggccaacc aggagcagcc | 20 |

<210> SEQ ID NO 162
<211> LENGTH: 20
<212> TYPE: DNA
<213> ORGANISM: Artificial Sequence
<220> FEATURE:
<223> OTHER INFORMATION: Oligomeric compound

<400> SEQUENCE: 162

| | |
|---|---|
| accaagtgcc aaactgagat | 20 |

<210> SEQ ID NO 163
<211> LENGTH: 20
<212> TYPE: DNA
<213> ORGANISM: Artificial Sequence
<220> FEATURE:
<223> OTHER INFORMATION: Oligomeric compound

<400> SEQUENCE: 163

| | |
|---|---|
| atggcccacc aagtgccaaa | 20 |

<210> SEQ ID NO 164
<211> LENGTH: 20
<212> TYPE: DNA
<213> ORGANISM: Artificial Sequence
<220> FEATURE:
<223> OTHER INFORMATION: Oligomeric compound

<400> SEQUENCE: 164

| | |
|---|---|
| ctggttgaca ggatggccca | 20 |

<210> SEQ ID NO 165
<211> LENGTH: 20
<212> TYPE: DNA
<213> ORGANISM: Artificial Sequence
<220> FEATURE:
<223> OTHER INFORMATION: Oligomeric compound

<400> SEQUENCE: 165

| | |
|---|---|
| catgctggtt gacaggatgg | 20 |

<210> SEQ ID NO 166
<211> LENGTH: 20
<212> TYPE: DNA
<213> ORGANISM: Artificial Sequence
<220> FEATURE:

<223> OTHER INFORMATION: Oligomeric compound

<400> SEQUENCE: 166
agccaggttc atgctggttg                                           20

<210> SEQ ID NO 167
<211> LENGTH: 20
<212> TYPE: DNA
<213> ORGANISM: Artificial Sequence
<220> FEATURE:
<223> OTHER INFORMATION: Oligomeric compound

<400> SEQUENCE: 167
tccagccagg ttcatgctgg                                           20

<210> SEQ ID NO 168
<211> LENGTH: 20
<212> TYPE: DNA
<213> ORGANISM: Artificial Sequence
<220> FEATURE:
<223> OTHER INFORMATION: Oligomeric compound

<400> SEQUENCE: 168
ccctccagcc aggttcatgc                                           20

<210> SEQ ID NO 169
<211> LENGTH: 20
<212> TYPE: DNA
<213> ORGANISM: Artificial Sequence
<220> FEATURE:
<223> OTHER INFORMATION: Oligomeric compound

<400> SEQUENCE: 169
ccagccctcc agccaggttc                                           20

<210> SEQ ID NO 170
<211> LENGTH: 20
<212> TYPE: DNA
<213> ORGANISM: Artificial Sequence
<220> FEATURE:
<223> OTHER INFORMATION: Oligomeric compound

<400> SEQUENCE: 170
gtgctgcgcc agctgtagct                                           20

<210> SEQ ID NO 171
<211> LENGTH: 20
<212> TYPE: DNA
<213> ORGANISM: Artificial Sequence
<220> FEATURE:
<223> OTHER INFORMATION: Oligomeric compound

<400> SEQUENCE: 171
ccagcgtgct gcgccagctg                                           20

<210> SEQ ID NO 172
<211> LENGTH: 20
<212> TYPE: DNA
<213> ORGANISM: Artificial Sequence
<220> FEATURE:
<223> OTHER INFORMATION: Oligomeric compound

<400> SEQUENCE: 172
acaaccacac acagtgcccc                                           20

<210> SEQ ID NO 173

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 173
gaaggagaca accacacaca                                                   20

<210> SEQ ID NO 174
<211> LENGTH: 20
<212> TYPE: DNA
<213> ORGANISM: Artificial Sequence
<220> FEATURE:
<223> OTHER INFORMATION: Oligomeric compound

<400> SEQUENCE: 174
agaggaagga gacaaccaca                                                   20

<210> SEQ ID NO 175
<211> LENGTH: 20
<212> TYPE: DNA
<213> ORGANISM: Artificial Sequence
<220> FEATURE:
<223> OTHER INFORMATION: Oligomeric compound

<400> SEQUENCE: 175
agcaggttca ttgtggatga                                                   20

<210> SEQ ID NO 176
<211> LENGTH: 20
<212> TYPE: DNA
<213> ORGANISM: Artificial Sequence
<220> FEATURE:
<223> OTHER INFORMATION: Oligomeric compound

<400> SEQUENCE: 176
acatcagcag gttcattgtg                                                   20

<210> SEQ ID NO 177
<211> LENGTH: 20
<212> TYPE: DNA
<213> ORGANISM: Artificial Sequence
<220> FEATURE:
<223> OTHER INFORMATION: Oligomeric compound

<400> SEQUENCE: 177
caaggagccc ttcttgccct                                                   20

<210> SEQ ID NO 178
<211> LENGTH: 20
<212> TYPE: DNA
<213> ORGANISM: Artificial Sequence
<220> FEATURE:
<223> OTHER INFORMATION: Oligomeric compound

<400> SEQUENCE: 178
tccttcaagg agcccttctt                                                   20

<210> SEQ ID NO 179
<211> LENGTH: 20
<212> TYPE: DNA
<213> ORGANISM: Artificial Sequence
<220> FEATURE:
<223> OTHER INFORMATION: Oligomeric compound

<400> SEQUENCE: 179
```

| | |
|---|---|
| tctcctcctt caaggagccc | 20 |

<210> SEQ ID NO 180
<211> LENGTH: 20
<212> TYPE: DNA
<213> ORGANISM: Artificial Sequence
<220> FEATURE:
<223> OTHER INFORMATION: Oligomeric compound

<400> SEQUENCE: 180

| | |
|---|---|
| gtgctctcct ccttcaagga | 20 |

<210> SEQ ID NO 181
<211> LENGTH: 20
<212> TYPE: DNA
<213> ORGANISM: Artificial Sequence
<220> FEATURE:
<223> OTHER INFORMATION: Oligomeric compound

<400> SEQUENCE: 181

| | |
|---|---|
| gaactggccc cagtcagtac | 20 |

<210> SEQ ID NO 182
<211> LENGTH: 20
<212> TYPE: DNA
<213> ORGANISM: Artificial Sequence
<220> FEATURE:
<223> OTHER INFORMATION: Oligomeric compound

<400> SEQUENCE: 182

| | |
|---|---|
| tctcctggat aaggaagaac | 20 |

<210> SEQ ID NO 183
<211> LENGTH: 20
<212> TYPE: DNA
<213> ORGANISM: Artificial Sequence
<220> FEATURE:
<223> OTHER INFORMATION: Oligomeric compound

<400> SEQUENCE: 183

| | |
|---|---|
| tcctttctcc tggataagga | 20 |

<210> SEQ ID NO 184
<211> LENGTH: 20
<212> TYPE: DNA
<213> ORGANISM: Artificial Sequence
<220> FEATURE:
<223> OTHER INFORMATION: Oligomeric compound

<400> SEQUENCE: 184

| | |
|---|---|
| ttacccggaa gaggtacatg | 20 |

<210> SEQ ID NO 185
<211> LENGTH: 20
<212> TYPE: DNA
<213> ORGANISM: Artificial Sequence
<220> FEATURE:
<223> OTHER INFORMATION: Oligomeric compound

<400> SEQUENCE: 185

| | |
|---|---|
| tcactgttac ccggaagagg | 20 |

<210> SEQ ID NO 186
<211> LENGTH: 20
<212> TYPE: DNA
<213> ORGANISM: Artificial Sequence
<220> FEATURE:

-continued

<223> OTHER INFORMATION: Oligomeric compound

<400> SEQUENCE: 186
ctggtcactg ttacccggaa                                                 20

<210> SEQ ID NO 187
<211> LENGTH: 20
<212> TYPE: DNA
<213> ORGANISM: Artificial Sequence
<220> FEATURE:
<223> OTHER INFORMATION: Oligomeric compound

<400> SEQUENCE: 187
gtcactggtc actgttaccc                                                 20

<210> SEQ ID NO 188
<211> LENGTH: 20
<212> TYPE: DNA
<213> ORGANISM: Artificial Sequence
<220> FEATURE:
<223> OTHER INFORMATION: Oligomeric compound

<400> SEQUENCE: 188
taccaggatc cagagcttgg                                                 20

<210> SEQ ID NO 189
<211> LENGTH: 20
<212> TYPE: DNA
<213> ORGANISM: Artificial Sequence
<220> FEATURE:
<223> OTHER INFORMATION: Oligomeric compound

<400> SEQUENCE: 189
tcccaatacc aggatccaga                                                 20

<210> SEQ ID NO 190
<211> LENGTH: 20
<212> TYPE: DNA
<213> ORGANISM: Artificial Sequence
<220> FEATURE:
<223> OTHER INFORMATION: Oligomeric compound

<400> SEQUENCE: 190
acagctccca ataccaggat                                                 20

<210> SEQ ID NO 191
<211> LENGTH: 20
<212> TYPE: DNA
<213> ORGANISM: Artificial Sequence
<220> FEATURE:
<223> OTHER INFORMATION: Oligomeric compound

<400> SEQUENCE: 191
caaatacagc tcccaatacc                                                 20

<210> SEQ ID NO 192
<211> LENGTH: 20
<212> TYPE: DNA
<213> ORGANISM: Artificial Sequence
<220> FEATURE:
<223> OTHER INFORMATION: Oligomeric compound

<400> SEQUENCE: 192
gaaaccaaat acagctccca                                                 20

<210> SEQ ID NO 193

-continued

```
<211> LENGTH: 20
<212> TYPE: DNA
<213> ORGANISM: Artificial Sequence
<220> FEATURE:
<223> OTHER INFORMATION: Oligomeric compound

<400> SEQUENCE: 193
gagaaaccaa atacagctcc                                               20

<210> SEQ ID NO 194
<211> LENGTH: 20
<212> TYPE: DNA
<213> ORGANISM: Artificial Sequence
<220> FEATURE:
<223> OTHER INFORMATION: Oligomeric compound

<400> SEQUENCE: 194
cgaggagaaa ccaaatacag                                               20

<210> SEQ ID NO 195
<211> LENGTH: 20
<212> TYPE: DNA
<213> ORGANISM: Artificial Sequence
<220> FEATURE:
<223> OTHER INFORMATION: Oligomeric compound

<400> SEQUENCE: 195
ccatacgagg agaaaccaaa                                               20

<210> SEQ ID NO 196
<211> LENGTH: 20
<212> TYPE: DNA
<213> ORGANISM: Artificial Sequence
<220> FEATURE:
<223> OTHER INFORMATION: Oligomeric compound

<400> SEQUENCE: 196
gtgcttggca atggtgctga                                               20

<210> SEQ ID NO 197
<211> LENGTH: 20
<212> TYPE: DNA
<213> ORGANISM: Artificial Sequence
<220> FEATURE:
<223> OTHER INFORMATION: Oligomeric compound

<400> SEQUENCE: 197
tgtagtgctt ggcaatggtg                                               20

<210> SEQ ID NO 198
<211> LENGTH: 20
<212> TYPE: DNA
<213> ORGANISM: Artificial Sequence
<220> FEATURE:
<223> OTHER INFORMATION: Oligomeric compound

<400> SEQUENCE: 198
gccacccaga aggctgtgct                                               20

<210> SEQ ID NO 199
<211> LENGTH: 20
<212> TYPE: DNA
<213> ORGANISM: Artificial Sequence
<220> FEATURE:
<223> OTHER INFORMATION: Oligomeric compound

<400> SEQUENCE: 199
```

-continued

```
ttcagccacc cagaaggctg                                                      20

<210> SEQ ID NO 200
<211> LENGTH: 20
<212> TYPE: DNA
<213> ORGANISM: Artificial Sequence
<220> FEATURE:
<223> OTHER INFORMATION: Oligomeric compound

<400> SEQUENCE: 200
ccatcttggt gcggatgttt                                                      20

<210> SEQ ID NO 201
<211> LENGTH: 20
<212> TYPE: DNA
<213> ORGANISM: Artificial Sequence
<220> FEATURE:
<223> OTHER INFORMATION: Oligomeric compound

<400> SEQUENCE: 201
actcggccca tcttggtgcg                                                      20

<210> SEQ ID NO 202
<211> LENGTH: 20
<212> TYPE: DNA
<213> ORGANISM: Artificial Sequence
<220> FEATURE:
<223> OTHER INFORMATION: Oligomeric compound

<400> SEQUENCE: 202
cagaccaacc aggagcagcc                                                      20

<210> SEQ ID NO 203
<211> LENGTH: 20
<212> TYPE: DNA
<213> ORGANISM: Artificial Sequence
<220> FEATURE:
<223> OTHER INFORMATION: Oligomeric compound

<400> SEQUENCE: 203
gtgcttggcg atggtactga                                                      20

<210> SEQ ID NO 204
<211> LENGTH: 380
<212> TYPE: DNA
<213> ORGANISM: M. musculus

<400> SEQUENCE: 204
gtcgttcggg gacccacagc cccgcagtac ggaccccta ctgatgtcgc agggacactg           60
ggttccctgg ttgctgcccc agcttaatga ttgtccagaa ggcggctata aagagcctgg        120
gtggaggaga gagaaagcgc acagaaaaac acagctcagc agatccaggc actaaagaga        180
gctagctgca acatggagca gtcaagaatc tgtggtcaga agtactggag tgggccagca        240
ggcgagtctt tttctaccat ggcagcccaa ggtacggcta ctatcgcact gtcatatttg        300
cggccatgtt tggaggctac agcctgtact atttcaaccg caaaaccttc tcctttgtca        360
tgccctcttg gtggatgaga                                                     380

<210> SEQ ID NO 205
<211> LENGTH: 20
<212> TYPE: DNA
<213> ORGANISM: Artificial Sequence
<220> FEATURE:
<223> OTHER INFORMATION: Oligomeric compound
```

-continued

<400> SEQUENCE: 205
ctcttgactg ctcctgcttg                                              20

<210> SEQ ID NO 206
<211> LENGTH: 20
<212> TYPE: DNA
<213> ORGANISM: Artificial Sequence
<220> FEATURE:
<223> OTHER INFORMATION: Oligomeric compound

<400> SEQUENCE: 206
cttctgacca cagactcttg                                              20

<210> SEQ ID NO 207
<211> LENGTH: 20
<212> TYPE: DNA
<213> ORGANISM: Artificial Sequence
<220> FEATURE:
<223> OTHER INFORMATION: Oligomeric compound

<400> SEQUENCE: 207
gcccactcca gtacttctga                                              20

<210> SEQ ID NO 208
<211> LENGTH: 20
<212> TYPE: DNA
<213> ORGANISM: Artificial Sequence
<220> FEATURE:
<223> OTHER INFORMATION: Oligomeric compound

<400> SEQUENCE: 208
aagctggccc tgctggccca                                              20

<210> SEQ ID NO 209
<211> LENGTH: 20
<212> TYPE: DNA
<213> ORGANISM: Artificial Sequence
<220> FEATURE:
<223> OTHER INFORMATION: Oligomeric compound

<400> SEQUENCE: 209
gtagaaaaag ctggccctgc                                              20

<210> SEQ ID NO 210
<211> LENGTH: 20
<212> TYPE: DNA
<213> ORGANISM: Artificial Sequence
<220> FEATURE:
<223> OTHER INFORMATION: Oligomeric compound

<400> SEQUENCE: 210
ttgggctgcc atggtagaaa                                              20

<210> SEQ ID NO 211
<211> LENGTH: 20
<212> TYPE: DNA
<213> ORGANISM: Artificial Sequence
<220> FEATURE:
<223> OTHER INFORMATION: Oligomeric compound

<400> SEQUENCE: 211
agtgcgatag tagccgtagc                                              20

<210> SEQ ID NO 212
<211> LENGTH: 20
<212> TYPE: DNA

```
<213> ORGANISM: Artificial Sequence
<220> FEATURE:
<223> OTHER INFORMATION: Oligomeric compound

<400> SEQUENCE: 212
aacatggccg caaatatgac                                                    20

<210> SEQ ID NO 213
<211> LENGTH: 20
<212> TYPE: DNA
<213> ORGANISM: Artificial Sequence
<220> FEATURE:
<223> OTHER INFORMATION: Oligomeric compound

<400> SEQUENCE: 213
tacaggctgt agcctccaaa                                                    20

<210> SEQ ID NO 214
<211> LENGTH: 20
<212> TYPE: DNA
<213> ORGANISM: Artificial Sequence
<220> FEATURE:
<223> OTHER INFORMATION: Oligomeric compound

<400> SEQUENCE: 214
tggtctgaca gaaccccgct                                                    20

<210> SEQ ID NO 215
<211> LENGTH: 20
<212> TYPE: DNA
<213> ORGANISM: Artificial Sequence
<220> FEATURE:
<223> OTHER INFORMATION: Oligomeric compound

<400> SEQUENCE: 215
cgctcatctg gtctgacaga                                                    20

<210> SEQ ID NO 216
<211> LENGTH: 20
<212> TYPE: DNA
<213> ORGANISM: Artificial Sequence
<220> FEATURE:
<223> OTHER INFORMATION: Oligomeric compound

<400> SEQUENCE: 216
tgtggagctc catgagaaga                                                    20

<210> SEQ ID NO 217
<211> LENGTH: 20
<212> TYPE: DNA
<213> ORGANISM: Artificial Sequence
<220> FEATURE:
<223> OTHER INFORMATION: Oligomeric compound

<400> SEQUENCE: 217
accaaggagc agcaaaggct                                                    20

<210> SEQ ID NO 218
<211> LENGTH: 20
<212> TYPE: DNA
<213> ORGANISM: Artificial Sequence
<220> FEATURE:
<223> OTHER INFORMATION: Oligomeric compound

<400> SEQUENCE: 218
ttgacaacac agcccaccaa                                                    20
```

```
<210> SEQ ID NO 219
<211> LENGTH: 20
<212> TYPE: DNA
<213> ORGANISM: Artificial Sequence
<220> FEATURE:
<223> OTHER INFORMATION: Oligomeric compound

<400> SEQUENCE: 219
ccagccaggt tcatgctggt                                               20

<210> SEQ ID NO 220
<211> LENGTH: 20
<212> TYPE: DNA
<213> ORGANISM: Artificial Sequence
<220> FEATURE:
<223> OTHER INFORMATION: Oligomeric compound

<400> SEQUENCE: 220
aagataggtc ccaaacttcc                                               20

<210> SEQ ID NO 221
<211> LENGTH: 20
<212> TYPE: DNA
<213> ORGANISM: Artificial Sequence
<220> FEATURE:
<223> OTHER INFORMATION: Oligomeric compound

<400> SEQUENCE: 221
cacagtgccc cagacagggc                                               20

<210> SEQ ID NO 222
<211> LENGTH: 20
<212> TYPE: DNA
<213> ORGANISM: Artificial Sequence
<220> FEATURE:
<223> OTHER INFORMATION: Oligomeric compound

<400> SEQUENCE: 222
tgtggatgag cagcagacag                                               20

<210> SEQ ID NO 223
<211> LENGTH: 20
<212> TYPE: DNA
<213> ORGANISM: Artificial Sequence
<220> FEATURE:
<223> OTHER INFORMATION: Oligomeric compound

<400> SEQUENCE: 223
cagcaggttc attgtggatg                                               20

<210> SEQ ID NO 224
<211> LENGTH: 20
<212> TYPE: DNA
<213> ORGANISM: Artificial Sequence
<220> FEATURE:
<223> OTHER INFORMATION: Oligomeric compound

<400> SEQUENCE: 224
aacatcagca ggttcattgt                                               20

<210> SEQ ID NO 225
<211> LENGTH: 20
<212> TYPE: DNA
<213> ORGANISM: Artificial Sequence
<220> FEATURE:
<223> OTHER INFORMATION: Oligomeric compound
```

```
<400> SEQUENCE: 225
cttcttgccc tcagagggca                                              20

<210> SEQ ID NO 226
<211> LENGTH: 20
<212> TYPE: DNA
<213> ORGANISM: Artificial Sequence
<220> FEATURE:
<223> OTHER INFORMATION: Oligomeric compound

<400> SEQUENCE: 226
gagcccttct tgccctcaga                                              20

<210> SEQ ID NO 227
<211> LENGTH: 20
<212> TYPE: DNA
<213> ORGANISM: Artificial Sequence
<220> FEATURE:
<223> OTHER INFORMATION: Oligomeric compound

<400> SEQUENCE: 227
tcaaggagcc cttcttgccc                                              20

<210> SEQ ID NO 228
<211> LENGTH: 20
<212> TYPE: DNA
<213> ORGANISM: Artificial Sequence
<220> FEATURE:
<223> OTHER INFORMATION: Oligomeric compound

<400> SEQUENCE: 228
ctccttcaag gagcccttct                                              20

<210> SEQ ID NO 229
<211> LENGTH: 20
<212> TYPE: DNA
<213> ORGANISM: Artificial Sequence
<220> FEATURE:
<223> OTHER INFORMATION: Oligomeric compound

<400> SEQUENCE: 229
ctctcctcct tcaaggagcc                                              20

<210> SEQ ID NO 230
<211> LENGTH: 20
<212> TYPE: DNA
<213> ORGANISM: Artificial Sequence
<220> FEATURE:
<223> OTHER INFORMATION: Oligomeric compound

<400> SEQUENCE: 230
gggtgctctc ctccttcaag                                              20

<210> SEQ ID NO 231
<211> LENGTH: 20
<212> TYPE: DNA
<213> ORGANISM: Artificial Sequence
<220> FEATURE:
<223> OTHER INFORMATION: Oligomeric compound

<400> SEQUENCE: 231
cagctcctgt agggtgctct                                              20

<210> SEQ ID NO 232
<211> LENGTH: 20
<212> TYPE: DNA
```

```
<213> ORGANISM: Artificial Sequence
<220> FEATURE:
<223> OTHER INFORMATION: Oligomeric compound

<400> SEQUENCE: 232
tctttactcc gaagaccaca                                                  20

<210> SEQ ID NO 233
<211> LENGTH: 20
<212> TYPE: DNA
<213> ORGANISM: Artificial Sequence
<220> FEATURE:
<223> OTHER INFORMATION: Oligomeric compound

<400> SEQUENCE: 233
ctcctggata aggaagaact                                                  20

<210> SEQ ID NO 234
<211> LENGTH: 20
<212> TYPE: DNA
<213> ORGANISM: Artificial Sequence
<220> FEATURE:
<223> OTHER INFORMATION: Oligomeric compound

<400> SEQUENCE: 234
actgccctct ctcctggata                                                  20

<210> SEQ ID NO 235
<211> LENGTH: 20
<212> TYPE: DNA
<213> ORGANISM: Artificial Sequence
<220> FEATURE:
<223> OTHER INFORMATION: Oligomeric compound

<400> SEQUENCE: 235
caagggcgga ctgccctctc                                                  20

<210> SEQ ID NO 236
<211> LENGTH: 20
<212> TYPE: DNA
<213> ORGANISM: Artificial Sequence
<220> FEATURE:
<223> OTHER INFORMATION: Oligomeric compound

<400> SEQUENCE: 236
ctccgacctc gagggcactg                                                  20

<210> SEQ ID NO 237
<211> LENGTH: 20
<212> TYPE: DNA
<213> ORGANISM: Artificial Sequence
<220> FEATURE:
<223> OTHER INFORMATION: Oligomeric compound

<400> SEQUENCE: 237
tgtctgacag gtaaccagct                                                  20

<210> SEQ ID NO 238
<211> LENGTH: 20
<212> TYPE: DNA
<213> ORGANISM: Artificial Sequence
<220> FEATURE:
<223> OTHER INFORMATION: Oligomeric compound

<400> SEQUENCE: 238
gctgccatcc cagccatcat                                                  20
```

<210> SEQ ID NO 239
<211> LENGTH: 20
<212> TYPE: DNA
<213> ORGANISM: Artificial Sequence
<220> FEATURE:
<223> OTHER INFORMATION: Oligomeric compound

<400> SEQUENCE: 239
ggaagagata cgtggatgct                                              20

<210> SEQ ID NO 240
<211> LENGTH: 20
<212> TYPE: DNA
<213> ORGANISM: Artificial Sequence
<220> FEATURE:
<223> OTHER INFORMATION: Oligomeric compound

<400> SEQUENCE: 240
agtcactggt caccgttact                                              20

<210> SEQ ID NO 241
<211> LENGTH: 20
<212> TYPE: DNA
<213> ORGANISM: Artificial Sequence
<220> FEATURE:
<223> OTHER INFORMATION: Oligomeric compound

<400> SEQUENCE: 241
caatgggacc ataagaagag                                              20

<210> SEQ ID NO 242
<211> LENGTH: 20
<212> TYPE: DNA
<213> ORGANISM: Artificial Sequence
<220> FEATURE:
<223> OTHER INFORMATION: Oligomeric compound

<400> SEQUENCE: 242
ctccaaacaa ggcaatggga                                              20

<210> SEQ ID NO 243
<211> LENGTH: 20
<212> TYPE: DNA
<213> ORGANISM: Artificial Sequence
<220> FEATURE:
<223> OTHER INFORMATION: Oligomeric compound

<400> SEQUENCE: 243
tggctatgac tccaaacaag                                              20

<210> SEQ ID NO 244
<211> LENGTH: 20
<212> TYPE: DNA
<213> ORGANISM: Artificial Sequence
<220> FEATURE:
<223> OTHER INFORMATION: Oligomeric compound

<400> SEQUENCE: 244
ccacaatagc atgagaggtt                                              20

<210> SEQ ID NO 245
<211> LENGTH: 20
<212> TYPE: DNA
<213> ORGANISM: Artificial Sequence
<220> FEATURE:
<223> OTHER INFORMATION: Oligomeric compound

```
<400> SEQUENCE: 245
tccacccaca ttggccataa                                           20

<210> SEQ ID NO 246
<211> LENGTH: 20
<212> TYPE: DNA
<213> ORGANISM: Artificial Sequence
<220> FEATURE:
<223> OTHER INFORMATION: Oligomeric compound

<400> SEQUENCE: 246
agtgcttggc aatggtgctg                                           20

<210> SEQ ID NO 247
<211> LENGTH: 20
<212> TYPE: DNA
<213> ORGANISM: Artificial Sequence
<220> FEATURE:
<223> OTHER INFORMATION: Oligomeric compound

<400> SEQUENCE: 247
accacttctg ccacccagaa                                           20

<210> SEQ ID NO 248
<211> LENGTH: 20
<212> TYPE: DNA
<213> ORGANISM: Artificial Sequence
<220> FEATURE:
<223> OTHER INFORMATION: Oligomeric compound

<400> SEQUENCE: 248
gctggctcca caaaccactt                                           20

<210> SEQ ID NO 249
<211> LENGTH: 20
<212> TYPE: DNA
<213> ORGANISM: Artificial Sequence
<220> FEATURE:
<223> OTHER INFORMATION: Oligomeric compound

<400> SEQUENCE: 249
cttggtgcgg atatttcgaa                                           20

<210> SEQ ID NO 250
<211> LENGTH: 20
<212> TYPE: DNA
<213> ORGANISM: Artificial Sequence
<220> FEATURE:
<223> OTHER INFORMATION: Oligomeric compound

<400> SEQUENCE: 250
tggatactcg gcccatcttg                                           20

<210> SEQ ID NO 251
<211> LENGTH: 20
<212> TYPE: DNA
<213> ORGANISM: Artificial Sequence
<220> FEATURE:
<223> OTHER INFORMATION: Oligomeric compound

<400> SEQUENCE: 251
ggactcgatt cactctccct                                           20

<210> SEQ ID NO 252
<211> LENGTH: 20
<212> TYPE: DNA
```

```
<213> ORGANISM: Artificial Sequence
<220> FEATURE:
<223> OTHER INFORMATION: Oligomeric compound

<400> SEQUENCE: 252
gggatgctcc atagcgagga                                              20

<210> SEQ ID NO 253
<211> LENGTH: 20
<212> TYPE: DNA
<213> ORGANISM: Artificial Sequence
<220> FEATURE:
<223> OTHER INFORMATION: Oligomeric compound

<400> SEQUENCE: 253
cctgccagta aggctgcagt                                              20

<210> SEQ ID NO 254
<211> LENGTH: 20
<212> TYPE: DNA
<213> ORGANISM: Artificial Sequence
<220> FEATURE:
<223> OTHER INFORMATION: Oligomeric compound

<400> SEQUENCE: 254
gagagacagt ggagacacag                                              20

<210> SEQ ID NO 255
<211> LENGTH: 20
<212> TYPE: DNA
<213> ORGANISM: Artificial Sequence
<220> FEATURE:
<223> OTHER INFORMATION: Oligomeric compound

<400> SEQUENCE: 255
tggaggttca gagagacagt                                              20

<210> SEQ ID NO 256
<211> LENGTH: 20
<212> TYPE: DNA
<213> ORGANISM: Artificial Sequence
<220> FEATURE:
<223> OTHER INFORMATION: Oligomeric compound

<400> SEQUENCE: 256
gtaacttgca gcaccatgga                                              20

<210> SEQ ID NO 257
<211> LENGTH: 20
<212> TYPE: DNA
<213> ORGANISM: Artificial Sequence
<220> FEATURE:
<223> OTHER INFORMATION: Oligomeric compound

<400> SEQUENCE: 257
gccactggta acttgcagca                                              20

<210> SEQ ID NO 258
<211> LENGTH: 20
<212> TYPE: DNA
<213> ORGANISM: Artificial Sequence
<220> FEATURE:
<223> OTHER INFORMATION: Oligomeric compound

<400> SEQUENCE: 258
aggagttgcc tgtctgccag                                              20
```

```
<210> SEQ ID NO 259
<211> LENGTH: 20
<212> TYPE: DNA
<213> ORGANISM: Artificial Sequence
<220> FEATURE:
<223> OTHER INFORMATION: Oligomeric compound

<400> SEQUENCE: 259
ccctgaattc aggagttgcc                                           20

<210> SEQ ID NO 260
<211> LENGTH: 20
<212> TYPE: DNA
<213> ORGANISM: Artificial Sequence
<220> FEATURE:
<223> OTHER INFORMATION: Oligomeric compound

<400> SEQUENCE: 260
tactcactag gagatcagga                                           20

<210> SEQ ID NO 261
<211> LENGTH: 20
<212> TYPE: DNA
<213> ORGANISM: Artificial Sequence
<220> FEATURE:
<223> OTHER INFORMATION: Oligomeric compound

<400> SEQUENCE: 261
caattttgcc ccctgccaag                                           20

<210> SEQ ID NO 262
<211> LENGTH: 20
<212> TYPE: DNA
<213> ORGANISM: Artificial Sequence
<220> FEATURE:
<223> OTHER INFORMATION: Oligomeric compound

<400> SEQUENCE: 262
gagtggtgga ctcctctcct                                           20

<210> SEQ ID NO 263
<211> LENGTH: 20
<212> TYPE: DNA
<213> ORGANISM: Artificial Sequence
<220> FEATURE:
<223> OTHER INFORMATION: Oligomeric compound

<400> SEQUENCE: 263
tcaaatctag ctttattcga                                           20

<210> SEQ ID NO 264
<211> LENGTH: 20
<212> TYPE: DNA
<213> ORGANISM: Artificial Sequence
<220> FEATURE:
<223> OTHER INFORMATION: Oligomeric compound

<400> SEQUENCE: 264
ggctgtgggt ccccgaacga                                           20

<210> SEQ ID NO 265
<211> LENGTH: 20
<212> TYPE: DNA
<213> ORGANISM: Artificial Sequence
<220> FEATURE:
<223> OTHER INFORMATION: Oligomeric compound
```

-continued

```
<400> SEQUENCE: 265
cagtgtccct gcgacatcag                                              20

<210> SEQ ID NO 266
<211> LENGTH: 20
<212> TYPE: DNA
<213> ORGANISM: Artificial Sequence
<220> FEATURE:
<223> OTHER INFORMATION: Oligomeric compound

<400> SEQUENCE: 266
gccgccttct ggacaatcat                                              20

<210> SEQ ID NO 267
<211> LENGTH: 20
<212> TYPE: DNA
<213> ORGANISM: Artificial Sequence
<220> FEATURE:
<223> OTHER INFORMATION: Oligomeric compound

<400> SEQUENCE: 267
ggctctttat agccgccttc                                              20

<210> SEQ ID NO 268
<211> LENGTH: 20
<212> TYPE: DNA
<213> ORGANISM: Artificial Sequence
<220> FEATURE:
<223> OTHER INFORMATION: Oligomeric compound

<400> SEQUENCE: 268
gcccactcca gtacttctga                                              20

<210> SEQ ID NO 269
<211> LENGTH: 20
<212> TYPE: DNA
<213> ORGANISM: Artificial Sequence
<220> FEATURE:
<223> OTHER INFORMATION: Oligomeric compound

<400> SEQUENCE: 269
cggatctgct gagctgtgtt                                              20

<210> SEQ ID NO 270
<211> LENGTH: 20
<212> TYPE: DNA
<213> ORGANISM: Artificial Sequence
<220> FEATURE:
<223> OTHER INFORMATION: Oligomeric compound

<400> SEQUENCE: 270
tccctctcca gtgcccggat                                              20

<210> SEQ ID NO 271
<211> LENGTH: 20
<212> TYPE: DNA
<213> ORGANISM: Artificial Sequence
<220> FEATURE:
<223> OTHER INFORMATION: Oligomeric compound

<400> SEQUENCE: 271
tcctgcttgc agctccctct                                              20

<210> SEQ ID NO 272
<211> LENGTH: 20
<212> TYPE: DNA
```

<213> ORGANISM: Artificial Sequence
<220> FEATURE:
<223> OTHER INFORMATION: Oligomeric compound

<400> SEQUENCE: 272
cacactcttg actgctcctg                                                    20

<210> SEQ ID NO 273
<211> LENGTH: 20
<212> TYPE: DNA
<213> ORGANISM: Artificial Sequence
<220> FEATURE:
<223> OTHER INFORMATION: Oligomeric compound

<400> SEQUENCE: 273
cacggtgctt ctgaccacac                                                    20

<210> SEQ ID NO 274
<211> LENGTH: 20
<212> TYPE: DNA
<213> ORGANISM: Artificial Sequence
<220> FEATURE:
<223> OTHER INFORMATION: Oligomeric compound

<400> SEQUENCE: 274
ggtccactca cggtgcttct                                                    20

<210> SEQ ID NO 275
<211> LENGTH: 20
<212> TYPE: DNA
<213> ORGANISM: Artificial Sequence
<220> FEATURE:
<223> OTHER INFORMATION: Oligomeric compound

<400> SEQUENCE: 275
gccatggtag aaaaagccgg                                                    20

<210> SEQ ID NO 276
<211> LENGTH: 20
<212> TYPE: DNA
<213> ORGANISM: Artificial Sequence
<220> FEATURE:
<223> OTHER INFORMATION: Oligomeric compound

<400> SEQUENCE: 276
catagccttg ggccgccatg                                                    20

<210> SEQ ID NO 277
<211> LENGTH: 20
<212> TYPE: DNA
<213> ORGANISM: Artificial Sequence
<220> FEATURE:
<223> OTHER INFORMATION: Oligomeric compound

<400> SEQUENCE: 277
atgacagtgc ggtaatagcc                                                    20

<210> SEQ ID NO 278
<211> LENGTH: 20
<212> TYPE: DNA
<213> ORGANISM: Artificial Sequence
<220> FEATURE:
<223> OTHER INFORMATION: Oligomeric compound

<400> SEQUENCE: 278
acatggctgt gaatatgaca                                                    20

```
<210> SEQ ID NO 279
<211> LENGTH: 20
<212> TYPE: DNA
<213> ORGANISM: Artificial Sequence
<220> FEATURE:
<223> OTHER INFORMATION: Oligomeric compound

<400> SEQUENCE: 279
taaaggctgt agcctccgaa                                              20

<210> SEQ ID NO 280
<211> LENGTH: 20
<212> TYPE: DNA
<213> ORGANISM: Artificial Sequence
<220> FEATURE:
<223> OTHER INFORMATION: Oligomeric compound

<400> SEQUENCE: 280
gcggttgaag tagtaaaggc                                              20

<210> SEQ ID NO 281
<211> LENGTH: 20
<212> TYPE: DNA
<213> ORGANISM: Artificial Sequence
<220> FEATURE:
<223> OTHER INFORMATION: Oligomeric compound

<400> SEQUENCE: 281
atgacaaaag agaaggtttt                                              20

<210> SEQ ID NO 282
<211> LENGTH: 20
<212> TYPE: DNA
<213> ORGANISM: Artificial Sequence
<220> FEATURE:
<223> OTHER INFORMATION: Oligomeric compound

<400> SEQUENCE: 282
caccaaggag ggcatgacaa                                              20

<210> SEQ ID NO 283
<211> LENGTH: 20
<212> TYPE: DNA
<213> ORGANISM: Artificial Sequence
<220> FEATURE:
<223> OTHER INFORMATION: Oligomeric compound

<400> SEQUENCE: 283
tgtccagagc gatctcatcc                                              20

<210> SEQ ID NO 284
<211> LENGTH: 20
<212> TYPE: DNA
<213> ORGANISM: Artificial Sequence
<220> FEATURE:
<223> OTHER INFORMATION: Oligomeric compound

<400> SEQUENCE: 284
ccccaaatcg tccttgtcca                                              20

<210> SEQ ID NO 285
<211> LENGTH: 20
<212> TYPE: DNA
<213> ORGANISM: Artificial Sequence
<220> FEATURE:
<223> OTHER INFORMATION: Oligomeric compound
```

```
<400> SEQUENCE: 285
ctggctgctc gtgatgagcc                                                  20

<210> SEQ ID NO 286
<211> LENGTH: 20
<212> TYPE: DNA
<213> ORGANISM: Artificial Sequence
<220> FEATURE:
<223> OTHER INFORMATION: Oligomeric compound

<400> SEQUENCE: 286
gatggcgtag gctgccgact                                                  20

<210> SEQ ID NO 287
<211> LENGTH: 20
<212> TYPE: DNA
<213> ORGANISM: Artificial Sequence
<220> FEATURE:
<223> OTHER INFORMATION: Oligomeric compound

<400> SEQUENCE: 287
ccaacgggca ctcatctgat                                                  20

<210> SEQ ID NO 288
<211> LENGTH: 20
<212> TYPE: DNA
<213> ORGANISM: Artificial Sequence
<220> FEATURE:
<223> OTHER INFORMATION: Oligomeric compound

<400> SEQUENCE: 288
cagaccaacc aggagcagcc                                                  20

<210> SEQ ID NO 289
<211> LENGTH: 20
<212> TYPE: DNA
<213> ORGANISM: Artificial Sequence
<220> FEATURE:
<223> OTHER INFORMATION: Oligomeric compound

<400> SEQUENCE: 289
tactgtagag ctccacgaga                                                  20

<210> SEQ ID NO 290
<211> LENGTH: 20
<212> TYPE: DNA
<213> ORGANISM: Artificial Sequence
<220> FEATURE:
<223> OTHER INFORMATION: Oligomeric compound

<400> SEQUENCE: 290
agaccattaa gaaaccagag                                                  20

<210> SEQ ID NO 291
<211> LENGTH: 20
<212> TYPE: DNA
<213> ORGANISM: Artificial Sequence
<220> FEATURE:
<223> OTHER INFORMATION: Oligomeric compound

<400> SEQUENCE: 291
cttcctcagg atcttcccac                                                  20

<210> SEQ ID NO 292
<211> LENGTH: 20
<212> TYPE: DNA
```

```
<213> ORGANISM: Artificial Sequence
<220> FEATURE:
<223> OTHER INFORMATION: Oligomeric compound

<400> SEQUENCE: 292
cccaccaagt accaaactgg                                              20

<210> SEQ ID NO 293
<211> LENGTH: 20
<212> TYPE: DNA
<213> ORGANISM: Artificial Sequence
<220> FEATURE:
<223> OTHER INFORMATION: Oligomeric compound

<400> SEQUENCE: 293
aaggattgtc gccaagatag                                              20

<210> SEQ ID NO 294
<211> LENGTH: 20
<212> TYPE: DNA
<213> ORGANISM: Artificial Sequence
<220> FEATURE:
<223> OTHER INFORMATION: Oligomeric compound

<400> SEQUENCE: 294
ccagggtgct gcgccagctg                                              20

<210> SEQ ID NO 295
<211> LENGTH: 20
<212> TYPE: DNA
<213> ORGANISM: Artificial Sequence
<220> FEATURE:
<223> OTHER INFORMATION: Oligomeric compound

<400> SEQUENCE: 295
ttcgttgtgg atgagcagga                                              20

<210> SEQ ID NO 296
<211> LENGTH: 20
<212> TYPE: DNA
<213> ORGANISM: Artificial Sequence
<220> FEATURE:
<223> OTHER INFORMATION: Oligomeric compound

<400> SEQUENCE: 296
ggtccagatt tcggagtcca                                              20

<210> SEQ ID NO 297
<211> LENGTH: 20
<212> TYPE: DNA
<213> ORGANISM: Artificial Sequence
<220> FEATURE:
<223> OTHER INFORMATION: Oligomeric compound

<400> SEQUENCE: 297
agggtgctct cctcctttga                                              20

<210> SEQ ID NO 298
<211> LENGTH: 20
<212> TYPE: DNA
<213> ORGANISM: Artificial Sequence
<220> FEATURE:
<223> OTHER INFORMATION: Oligomeric compound

<400> SEQUENCE: 298
gccagtggag agcacccaga                                              20
```

<210> SEQ ID NO 299
<211> LENGTH: 20
<212> TYPE: DNA
<213> ORGANISM: Artificial Sequence
<220> FEATURE:
<223> OTHER INFORMATION: Oligomeric compound

<400> SEQUENCE: 299
tacagcaagt ctttacccca                                               20

<210> SEQ ID NO 300
<211> LENGTH: 20
<212> TYPE: DNA
<213> ORGANISM: Artificial Sequence
<220> FEATURE:
<223> OTHER INFORMATION: Oligomeric compound

<400> SEQUENCE: 300
cctggataag gaagaactgg                                               20

<210> SEQ ID NO 301
<211> LENGTH: 20
<212> TYPE: DNA
<213> ORGANISM: Artificial Sequence
<220> FEATURE:
<223> OTHER INFORMATION: Oligomeric compound

<400> SEQUENCE: 301
gaactaccca caagggccga                                               20

<210> SEQ ID NO 302
<211> LENGTH: 20
<212> TYPE: DNA
<213> ORGANISM: Artificial Sequence
<220> FEATURE:
<223> OTHER INFORMATION: Oligomeric compound

<400> SEQUENCE: 302
ggcctccaac ctctagggca                                               20

<210> SEQ ID NO 303
<211> LENGTH: 20
<212> TYPE: DNA
<213> ORGANISM: Artificial Sequence
<220> FEATURE:
<223> OTHER INFORMATION: Oligomeric compound

<400> SEQUENCE: 303
gacagatagc cagctgcaat                                               20

<210> SEQ ID NO 304
<211> LENGTH: 20
<212> TYPE: DNA
<213> ORGANISM: Artificial Sequence
<220> FEATURE:
<223> OTHER INFORMATION: Oligomeric compound

<400> SEQUENCE: 304
cagacagccc tgcctttgcc                                               20

<210> SEQ ID NO 305
<211> LENGTH: 20
<212> TYPE: DNA
<213> ORGANISM: Artificial Sequence
<220> FEATURE:
<223> OTHER INFORMATION: Oligomeric compound

```
<400> SEQUENCE: 305
aacaggctgt ggcgagggtt                                                  20

<210> SEQ ID NO 306
<211> LENGTH: 20
<212> TYPE: DNA
<213> ORGANISM: Artificial Sequence
<220> FEATURE:
<223> OTHER INFORMATION: Oligomeric compound

<400> SEQUENCE: 306
tggatgctgc catgccagcc                                                  20

<210> SEQ ID NO 307
<211> LENGTH: 20
<212> TYPE: DNA
<213> ORGANISM: Artificial Sequence
<220> FEATURE:
<223> OTHER INFORMATION: Oligomeric compound

<400> SEQUENCE: 307
gtcgctggtc actgttaccc                                                  20

<210> SEQ ID NO 308
<211> LENGTH: 20
<212> TYPE: DNA
<213> ORGANISM: Artificial Sequence
<220> FEATURE:
<223> OTHER INFORMATION: Oligomeric compound

<400> SEQUENCE: 308
gctcccaata ccaggatcca                                                  20

<210> SEQ ID NO 309
<211> LENGTH: 20
<212> TYPE: DNA
<213> ORGANISM: Artificial Sequence
<220> FEATURE:
<223> OTHER INFORMATION: Oligomeric compound

<400> SEQUENCE: 309
aatgggacca taagaagaga                                                  20

<210> SEQ ID NO 310
<211> LENGTH: 20
<212> TYPE: DNA
<213> ORGANISM: Artificial Sequence
<220> FEATURE:
<223> OTHER INFORMATION: Oligomeric compound

<400> SEQUENCE: 310
tcattagcta tgactccaaa                                                  20

<210> SEQ ID NO 311
<211> LENGTH: 20
<212> TYPE: DNA
<213> ORGANISM: Artificial Sequence
<220> FEATURE:
<223> OTHER INFORMATION: Oligomeric compound

<400> SEQUENCE: 311
gagaggtacc acacaagttg                                                  20

<210> SEQ ID NO 312
<211> LENGTH: 20
<212> TYPE: DNA
```

```
<213> ORGANISM: Artificial Sequence
<220> FEATURE:
<223> OTHER INFORMATION: Oligomeric compound

<400> SEQUENCE: 312
cccacattgg ccatgagccc                                              20

<210> SEQ ID NO 313
<211> LENGTH: 20
<212> TYPE: DNA
<213> ORGANISM: Artificial Sequence
<220> FEATURE:
<223> OTHER INFORMATION: Oligomeric compound

<400> SEQUENCE: 313
gtactgaagg gtaacccagc                                              20

<210> SEQ ID NO 314
<211> LENGTH: 20
<212> TYPE: DNA
<213> ORGANISM: Artificial Sequence
<220> FEATURE:
<223> OTHER INFORMATION: Oligomeric compound

<400> SEQUENCE: 314
aggctgtgct ccagctatag                                              20

<210> SEQ ID NO 315
<211> LENGTH: 20
<212> TYPE: DNA
<213> ORGANISM: Artificial Sequence
<220> FEATURE:
<223> OTHER INFORMATION: Oligomeric compound

<400> SEQUENCE: 315
ctggctatac agatcacttc                                              20

<210> SEQ ID NO 316
<211> LENGTH: 20
<212> TYPE: DNA
<213> ORGANISM: Artificial Sequence
<220> FEATURE:
<223> OTHER INFORMATION: Oligomeric compound

<400> SEQUENCE: 316
atatttcgaa gcaagaagaa                                              20

<210> SEQ ID NO 317
<211> LENGTH: 20
<212> TYPE: DNA
<213> ORGANISM: Artificial Sequence
<220> FEATURE:
<223> OTHER INFORMATION: Oligomeric compound

<400> SEQUENCE: 317
gccttcttgg atactcggcc                                              20

<210> SEQ ID NO 318
<211> LENGTH: 20
<212> TYPE: DNA
<213> ORGANISM: Artificial Sequence
<220> FEATURE:
<223> OTHER INFORMATION: Oligomeric compound

<400> SEQUENCE: 318
atgctctata gtgagtgctc                                              20
```

```
<210> SEQ ID NO 319
<211> LENGTH: 20
<212> TYPE: DNA
<213> ORGANISM: Artificial Sequence
<220> FEATURE:
<223> OTHER INFORMATION: Oligomeric compound

<400> SEQUENCE: 319
gcagcctctc ttcctttctg                                                     20

<210> SEQ ID NO 320
<211> LENGTH: 20
<212> TYPE: DNA
<213> ORGANISM: Artificial Sequence
<220> FEATURE:
<223> OTHER INFORMATION: Oligomeric compound

<400> SEQUENCE: 320
acagatatgt aaaggctctg                                                     20

<210> SEQ ID NO 321
<211> LENGTH: 20
<212> TYPE: DNA
<213> ORGANISM: Artificial Sequence
<220> FEATURE:
<223> OTHER INFORMATION: Oligomeric compound

<400> SEQUENCE: 321
caccacggag gtccagagag                                                     20

<210> SEQ ID NO 322
<211> LENGTH: 20
<212> TYPE: DNA
<213> ORGANISM: Artificial Sequence
<220> FEATURE:
<223> OTHER INFORMATION: Oligomeric compound

<400> SEQUENCE: 322
ggacctcatt agccactggt                                                     20

<210> SEQ ID NO 323
<211> LENGTH: 20
<212> TYPE: DNA
<213> ORGANISM: Artificial Sequence
<220> FEATURE:
<223> OTHER INFORMATION: Oligomeric compound

<400> SEQUENCE: 323
cctaaaacca aacatcattt                                                     20

<210> SEQ ID NO 324
<211> LENGTH: 20
<212> TYPE: DNA
<213> ORGANISM: Artificial Sequence
<220> FEATURE:
<223> OTHER INFORMATION: Oligomeric compound

<400> SEQUENCE: 324
tctgctagaa ggtagaaaca                                                     20

<210> SEQ ID NO 325
<211> LENGTH: 20
<212> TYPE: DNA
<213> ORGANISM: Artificial Sequence
<220> FEATURE:
<223> OTHER INFORMATION: Oligomeric compound
```

```
<400> SEQUENCE: 325
ggagacaccc tgaatttagg                                              20

<210> SEQ ID NO 326
<211> LENGTH: 20
<212> TYPE: DNA
<213> ORGANISM: Artificial Sequence
<220> FEATURE:
<223> OTHER INFORMATION: Oligomeric compound

<400> SEQUENCE: 326
tgcagctgca gagatagaac                                              20

<210> SEQ ID NO 327
<211> LENGTH: 20
<212> TYPE: DNA
<213> ORGANISM: Artificial Sequence
<220> FEATURE:
<223> OTHER INFORMATION: Oligomeric compound

<400> SEQUENCE: 327
gtacagcaga aaccacaggc                                              20

<210> SEQ ID NO 328
<211> LENGTH: 20
<212> TYPE: DNA
<213> ORGANISM: Artificial Sequence
<220> FEATURE:
<223> OTHER INFORMATION: Oligomeric compound

<400> SEQUENCE: 328
gggactgagg tattggcaac                                              20

<210> SEQ ID NO 329
<211> LENGTH: 20
<212> TYPE: DNA
<213> ORGANISM: Artificial Sequence
<220> FEATURE:
<223> OTHER INFORMATION: Oligomeric compound

<400> SEQUENCE: 329
atgagagtgg tggcctcctc                                              20

<210> SEQ ID NO 330
<211> LENGTH: 20
<212> TYPE: DNA
<213> ORGANISM: Artificial Sequence
<220> FEATURE:
<223> OTHER INFORMATION: Oligomeric compound

<400> SEQUENCE: 330
ctacattcct ccctttttgtc                                             20

<210> SEQ ID NO 331
<211> LENGTH: 20
<212> TYPE: DNA
<213> ORGANISM: Artificial Sequence
<220> FEATURE:
<223> OTHER INFORMATION: Oligomeric compound

<400> SEQUENCE: 331
agacagtttg ctctctacat                                              20

<210> SEQ ID NO 332
<211> LENGTH: 20
<212> TYPE: DNA
```

-continued

<213> ORGANISM: Artificial Sequence
<220> FEATURE:
<223> OTHER INFORMATION: Oligomeric compound

<400> SEQUENCE: 332
caagacagtt tgctctctac                                          20

<210> SEQ ID NO 333
<211> LENGTH: 20
<212> TYPE: DNA
<213> ORGANISM: Artificial Sequence
<220> FEATURE:
<223> OTHER INFORMATION: Oligomeric compound

<400> SEQUENCE: 333
tacaagacag tttgctctct                                          20

<210> SEQ ID NO 334
<211> LENGTH: 20
<212> TYPE: DNA
<213> ORGANISM: Artificial Sequence
<220> FEATURE:
<223> OTHER INFORMATION: Oligomeric compound

<400> SEQUENCE: 334
tatacaagac agtttgctct                                          20

<210> SEQ ID NO 335
<211> LENGTH: 20
<212> TYPE: DNA
<213> ORGANISM: Artificial Sequence
<220> FEATURE:
<223> OTHER INFORMATION: Oligomeric compound

<400> SEQUENCE: 335
tctatacaag acagtttgct                                          20

<210> SEQ ID NO 336
<211> LENGTH: 20
<212> TYPE: DNA
<213> ORGANISM: Artificial Sequence
<220> FEATURE:
<223> OTHER INFORMATION: Oligomeric compound

<400> SEQUENCE: 336
agtctataca agacagtttg                                          20

<210> SEQ ID NO 337
<211> LENGTH: 20
<212> TYPE: DNA
<213> ORGANISM: Artificial Sequence
<220> FEATURE:
<223> OTHER INFORMATION: Oligomeric compound

<400> SEQUENCE: 337
ttagtctata caagacagtt                                          20

<210> SEQ ID NO 338
<211> LENGTH: 20
<212> TYPE: DNA
<213> ORGANISM: Artificial Sequence
<220> FEATURE:
<223> OTHER INFORMATION: Oligomeric compound

<400> SEQUENCE: 338
ttttagtatc aaatctagtt                                          20

```
<210> SEQ ID NO 339
<211> LENGTH: 18
<212> TYPE: DNA
<213> ORGANISM: Artificial Sequence
<220> FEATURE:
<223> OTHER INFORMATION: PCR primer

<400> SEQUENCE: 339
gctggaagcc tgggacct                                                    18

<210> SEQ ID NO 340
<211> LENGTH: 16
<212> TYPE: DNA
<213> ORGANISM: Artificial Sequence
<220> FEATURE:
<223> OTHER INFORMATION: PCR primer

<400> SEQUENCE: 340
ggtgctgcgc cagctg                                                      16

<210> SEQ ID NO 341
<211> LENGTH: 26
<212> TYPE: DNA
<213> ORGANISM: Artificial Sequence
<220> FEATURE:
<223> OTHER INFORMATION: PCR probe

<400> SEQUENCE: 341
tcttggcgac aatccttgct cagagc                                           26
```

MODULATION OF GLUCOSE-6-PHOSPHATASE TRANSLOCASE EXPRESSION

RELATED APPLICATIONS

This application is a divisional of U.S. application Ser. No. 11/111,288, filed Apr. 20, 2005, which claims priority under 35 USC 119(e) to U.S. provisional application Ser. No. 60/564,641 filed Apr. 21, 2004, U.S. Provisional application Ser. No. 60/576,478 filed Jun. 2, 2004, and U.S. Provisional Application Ser. No. 60/615,395 filed Sep. 30, 2004, all of which are incorporated herein by reference in their entirety.

SEQUENCE LISTING

The present application is being filed along with a Sequence Listing in electronic format. The Sequence Listing is provided as a file entitled HTS0009USD1SEQ.txt, created on Feb. 16, 2011 which is 72 Kb in size. The information in the electronic format of the sequence listing is incorporated herein by reference in its entirety.

FIELD OF THE INVENTION

Disclosed herein are compounds, compositions and methods for modulating the expression of glucose-6-phosphatase translocase in a cell, tissue or animal.

BACKGROUND OF THE INVENTION

Glucose production from glycogen by gluconeogenesis and glycogenolysis is a vital function of the liver and to a lesser extent, the kidney cortex during starvation. Both processes result in the formation of glucose-6-phosphatase (G6P). The glucose-6-phosphatase (G6Pase) system regulates the dephosphorylation of glucose-6-phosphatase to glucose thereby playing a critical role in glucose homeostasis (van Schaftingen and Gerin, Biochem. J., 362, 513-532).

G6Pase deficiency results in glycogen storage disease, also known as van Gierke disease, primarily resulting in hypoglycemia. The G6Pase protein system is composed of at least a catalase (G6PC1) and a translocase (G6PT1). Defects in G6PC1 are associated with glycogen storage disease type I (GSD I, later referred to as GSD Ia) and defects in G6PT1 are associated with a variant of GSD I referred to as GSD Ib (van Schaftingen and Gerin, Biochem. J., 362, 513-532).

GSD Ib, although less prevalent than GSD Ia, presents a panoply of maladies. At infancy, GSD type Ib patients exhibit a failure to thrive, hypoglycemia-induced seizures, hepatomegaly, recurrent bacterial infections, anemia and acute lactic acidosis. Dietary management of the disease in children requires continuous nighttime feedings by nasogastric or gastrostomy tube and by dietary regimens that include regular drinks of uncooked starch. As the children age, metabolic complications subside and the disease is more easily managed by frequent daytime meals. GSD Ib is clinically distinguishable from GSD Ia because GSD Ib patients frequently have neutropenia and/or neutrophil dysfunction rendering them more susceptible to bacterial infections, typically involving the skin, perirectal area, ears, and urinary tract. Gingivitis and mouth ulceration are common, and chronic inflammatory bowel disease does occur. Hyperlipidemia and hyperuricemia frequently occurs and require treatment as the patients age. With advancing years hepatoma, renal disease, gout and osteoporosis become more likely. Annual ultrasound or computed tomographic scans are indicated for patients over 20 years of age (Kannourakis, Semin. Hematol., 39, 103-106).

GSD Ib patients exhibit similar clinical symptoms to GSD Ia patients, yet unlike GSD Ia patients, the livers from GSD Ib patients possess normal or increased glucose-6-phosphatase activity in detergent-disrupted microsome preparations. In contrast, such enzymatic activity was absent or reduced in intact microsomes. (An et al., J. Biol. Chem., 276, 10722-10729) The identification of the G6PT1 cDNA confirmed that the disease was a result of deficient glucose-6-phosphatase transport rather than deficient catalytic activity.

The G6PT1 cDNA (also known as G6P translocase, glucose-6-phosphatase translocase, glucose-6-phosphatase, transport protein 1, glucose-6-phosphatase transporter 1, glycogen storage disease type Ib, GSD type Ib, GSD1b, MGC15729, and PRO0685) was isolated and found to be mutated in two patients with GSD type Ib (Gerin et al., FEBS Lett., 419, 235-238; Veiga-da-Cunha et al., Am. J. Hum. Genet., 63, 976-983). The gene was mapped to chromosome 11q23 (Veiga-da-Cunha et al., Am. J. Hum. Genet., 63, 976-983). Homologous cDNA clones were isolated from the mouse and rat (Lin et al., J. Biol. Chem., 273, 31656-31660).

The human G6PT1 gene contains nine exons. Exon 7 is absent in human liver and leukocyte RNA but present in heart and brain. The alternatively spliced products retain the reading frame. Also, there are two transcription start sites at approximately −200 and −100 relative to the initiator ATG (Gerin et al., Gene, 227, 189-195). G6PT1 expression increased 2-3 fold in insulin-deficient streptozocin-induced diabetes in liver, kidney and intestine of rats. Increased glucose concentrations increased G6PT1 mRNA levels while increased cAMP concentrations decreased G6PT1 mRNA levels. Consequently, these results indicate that G6PT1, as well as the catalytic subunit, is impaired in insulin-dependent diabetes (Li et al., J. Biol. Chem., 274, 33866-33868). Similarly, treatment of hyperglycemic rats with an inhibitor of G6PT1, a chlorogenic acid derivative, suppressed blood glucose levels (Herling et al., Eur. J. Pharmacol., 386, 75-82). Furthermore, treatment of rats with a chlorogenic acid derivative increased de novo lipogenesis and steatosis but left VLDL-triglyceride secretion unaffected (Bandsma et al., Diabetes, 50, 2591-2597). Unfortunately, while these properties make chlorogenic acid derivatives promising candidates as drugs for the treatment of type II diabetes, such compounds exhibit a short duration of action due to high plasma clearance and rapid elimination into the bile (Herling et al., Biochim. Biophys. Acta, 1569, 105-110).

As a consequence of G6PT1 involvement in diabetes and glycogen storage disease, there remains a long felt need for agents capable of effectively regulating G6PT1 function.

Antisense technology is emerging as an effective means for reducing the expression of specific gene products and has been proven to be uniquely useful in a number of therapeutic, diagnostic, and research applications.

Disclosed herein are antisense compounds useful for modulating gene expression and associated pathways via antisense mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

SUMMARY OF THE INVENTION

The present invention is directed to oligomeric compounds targeted to and hybridizable with a nucleic acid molecule encoding glucose-6-phosphatase translocase and which modulate the expression of glucose-6-phosphatase translocase. Contemplated and provided herein are oligomeric compounds comprising sequences 13 to 30 nucleotides in length. In a preferred embodiment of the present invention are oligomeric compounds comprising at least two chemical modifications selected from a modified internucleoside linkage, a modified nucleobase, or a modified sugar. Provided herein are chimeric oligonucleotides comprising a deoxy nucleotide region flanked on each of the 5' and 3' ends with at least one 2'-O-methoxyethyl nucleotide. Further provided are chimeric oligonucleotides comprising ten deoxynucleotides and flanked on both the 5' and 3' ends with five 2'-O-methoxyethyl nucleotides wherein each internucleoside linkage is a phosphorothioate. In a further embodiment, the oligomeric compounds of the present invention may have at least one 5-methylcytosine.

In one embodiment, the oligomeric compounds inhibit the expression of glucose-6-phosphatase translocase by at least 35%.

Further provided are methods of modulating the expression of glucose-6-phosphatase translocase in cells, tissues or animals comprising contacting said cells, tissues or animals with one or more of the compounds or compositions of the present invention. For example, in one embodiment, the compounds or compositions of the present invention can be used to inhibit the expression of glucose-6-phosphatase translocase in cells, tissues or animals.

In some embodiments, the compounds are used in the preparation of a medicament for administration to an animal in need of such treatment so that blood glucose, triglycerides, or cholesterol are lowered. In one embodiment, HbA1c levels are lowered. In certain embodiments, the compounds of the invention are used in the preparation of a medicament for administration to an animal for treatment of diabetes or a condition associated with metabolic syndrome.

In other embodiments, the present invention is directed to methods of ameliorating or lessening the severity of a condition in an animal comprising contacting said animal with an effective amount of an oligomeric compound of the invention. In other embodiments, the present invention is directed to methods of ameliorating or lessening the severity of a condition in an animal comprising contacting said animal with an effective amount of an oligomeric compound of the invention so that expression of glucose-6-phosphatase translocase is inhibited and measurement of one or more physical indicator of said condition indicates a lessening of the severity of said condition. In certain embodiments, the compounds of the invention are used in the preparation of a medicament for administration to an animal for ameliorating or lessening the severity of a condition. In some embodiments, the conditions include, but are not limited to, diabetes, insulin resistance, insulin deficiency, hypercholesterolemia, hyperglycemia, hyperlipidemia, hypertriglyceridemia, hyperfattyacidemia and liver steatosis. In one embodiment, the diabetes is type II diabetes. In another embodiment, the diabetes is diet-induced. In another embodiment, the condition is metabolic syndrome. In another embodiment, the condition is a cardiovascular disease. In another embodiment, the cardiovascular disease is coronary heart disease. In another embodiment, the condition is a cardiovascular risk factor.

DETAILED DESCRIPTION

Overview

Disclosed herein are oligomeric compounds, including antisense oligonucleotides and other antisense compounds for use in modulating the expression of nucleic acid molecules encoding glucose-6-phosphatase translocase. This is accomplished by providing oligomeric compounds which hybridize with one or more target nucleic acid molecules encoding glucose-6-phosphatase translocase.

In accordance with the present invention are compositions and methods for modulating the expression of glucose-6-phosphatase translocase (also known as Glucose-6-phosphatase/translocase, G6P Translocase, G6pt1, GSD Type Ib, GSD1b, MGC15729, PRO0685, glucose-6-phosphatase, transport protein 1, glucose-6-phosphate transporter 1, glycogen storage disease type 1b). Listed in Table 1 are GEN-BANK® accession numbers of sequences used to design oligomeric compounds targeted to glucose-6-phosphatase translocase. Oligomeric compounds of the invention include oligomeric compounds which hybridize with one or more target nucleic acid molecules shown in Table 1, as well as oligomeric compounds which hybridize to other nucleic acid molecules encoding glucose-6-phosphatase translocase. The oligomeric compounds may target any region, segment, or site of nucleic acid molecules which encode glucose-6-phosphatase translocase. Suitable target regions, segments, and sites include, but are not limited to, the 5'UTR, the start codon, the stop codon, the coding region, the 3'UTR, the 5' cap region, introns, exons, intron-exon junctions, exon-intron junctions, and exon-exon junctions.

TABLE 1

| Gene Targets | | |
|---|---|---|
| Species | Genbank # | SEQ ID NO |
| Human | NM_001467.1 | 1 |
| Human | NM_001467.2 | 2 |
| Mouse | NM_008063.1 | 3 |
| Mouse | AA896763.1 | 204 |
| Rat | AF080468.1 | 4 |

The locations on the target nucleic acid to which active oligomeric compounds hybridize are herein below referred to as "validated target segments." As used herein the term "validated target segment" is defined as at least a 13-nucleobase portion of a target region to which an active oligomeric compound is targeted. While not wishing to be bound by theory, it is presently believed that these target segments represent portions of the target nucleic acid which are accessible for hybridization.

Embodiments of the present invention include oligomeric compounds comprising sequences of 13 to 30 nucleotides in length and at least two modifications selected from a modified internucleoside linkage, a modified nucleobase, or a modified sugar. In one embodiment, the oligomeric compounds of the present invention are chimeric oligonucleotides. In one embodiment, the oligomeric compounds of the present invention are chimeric oligonucleotides comprising a deoxy nucleotide region flanked on each of the 5' and 3' ends with at least one 2'-O-(2-methoxyethyl) nucleotide. In another embodiment, the oligomeric compounds of the present invention are chimeric oligonucleotides comprising ten deoxynucleotides and flanked on both the 5' and 3' ends with five 2'-O-(2-methoxyethyl) nucleotides. In a further embodiment, the oligomeric compounds of the present invention may have at least one 5-methylcytosine.

In one embodiment the oligomeric compounds hybridize with glucose-6-phosphatase translocase. In another embodiment, the oligomeric compounds inhibit the expression of glucose-6-phosphatase translocase. In other embodiments, the oligomeric compounds inhibit the expression of glucose-6-phosphatase translocase wherein the expression of glucose-6-phosphatase translocase is inhibited by at least 10%, by at least 20%, by at least 30%, by at least 35%, by at least 40%, by at least 50%, by at least 60%, by at least 70%, by at least 80%, by at least 90%, or by 100%. In one embodiment, the oligomeric compounds inhibit the expression of glucose-6-phosphatase translocase by 35%.

In one embodiment, the present invention provides methods of lowering triglyceride levels in an animal by administering an oligomeric compound of the invention. In one embodiment, the triglycerides are circulating triglycerides. In another embodiment, provided are methods of lowering glucose in an animal by administering an oligomeric compound of the invention. In other embodiments, the present invention provides methods of lowering cholesterol levels or ALT or AST in an animal by administering an oligomeric compound of the invention. In other embodiments, the present invention provides methods of improving glucose tolerance in an animal by administering an oligomeric compound of the invention. Also provided are uses of the compounds of the invention in the preparation of medicaments for administration to an animal for lowering glucose, for lowering cholesterol, for lowering triglycerides, and for lowering ALT or AST. Triglycerides, cholesterol, glucose, HbA1c, and ALT or AST levels are routinely measured in the clinic. Circulating triglycerides include blood, serum, or plasma triglycerides. Glucose includes blood, serum, or plasma glucose. Cholesterol includes blood, serum, or plasma cholesterol. ALT or AST includes blood, serum, or plasma ALT or AST.

Other embodiments of the invention include methods of ameliorating or lessening the severity of a condition in an animal by administering an oligomeric compound which inhibits glucose-6-phosphatase translocase expression. Conditions include, but are not limited to, metabolic disorders, cardiovascular disorders, and disorders associated with glucose-6-phosphatase translocase expression. Metabolic disorders include, but are not limited to, obesity, diet-induced obesity, diabetes, insulin resistance, insulin deficiency, dyslipidemia, hyperlipidemia, hypercholesterolemia, hyperglycemia, hypertriglyceridemia, hyperfattyacidemia, liver steatosis and metabolic syndrome. Cardiovascular disorders include, but are not limited to, coronary heart disease. Also provided are methods of improving cardiovascular risk profile in an animal by improving one or more cardiovascular risk factors by administering an oligomeric compound of the invention. In one aspect, the invention provides the use of a compound in the preparation of a medicament for treating an animal having or suspected of having a condition selected from the group consisting of diabetes, type II diabetes, insulin resistance, insulin deficiency, hypercholesterolemia, hyperglycemia, hyperlipidemia, hypertriglyceridemia, hyperfattyacidemia, liver steatosis, metabolic syndrome, cardiovascular disease, or a cardiovascular risk factor.

Also provided are uses of the oligomeric compounds of the invention in the preparation of a medicament for administration to an animal in combination with other therapeutics to achieve an additive therapeutic effect. Other therapeutics include, but are not limited to, glucose-lowering drugs, anti-obesity drugs, and lipid-lowering drugs. In one embodiment, the oligomeric compounds are used in combination with glucose-lowering drugs for the treatment of diabetes. In one embodiment, the diabetes is type II diabetes. In another embodiment, the oligomeric compounds are used in combination with glucose lowering drugs wherein the glucose-lowering drug is a hormone, a hormone mimetic, a sulfonylurea, a biguanide, a meglitinide, a thiazolidinedione, an alpha glucosidase inhibitor, or an antisense compound not targeted to glucose-6-phosphatase translocase. In one embodiment, the oligomeric compounds are used in combination with rosiglitazone. In one embodiment, the oligomeric compounds are used in combination with a glucose-lowering drug to achieve an additive effect on lowering glucose. In another embodiment, the oligomeric compounds are used alone or in combination to decrease HbA1c levels. In other embodiments, the oligomeric compounds are used in combination with a glucose-lowering drug to achieve an additive effect in decreasing plasma triglycerides, plasma cholesterol, or to improve glucose tolerance.

In another embodiment, the compounds of the invention inhibit hepatic glucose output. In another embodiment, the compounds of the invention inhibit glucagon-stimulated hepatic glucose output.

In one embodiment, the oligomeric compounds of the invention are used alone or in combination, to lower glucose without causing increased plasma lactate levels, increased liver glycogen, neutropenia, or hypoglycemia.

In accordance with the invention, a series of duplexes, including dsRNA and mimetics thereof, comprising oligomeric compounds of the invention and their complements can be designed to target glucose-6-phosphatase translocase. In one embodiment of the invention, double-stranded antisense compounds encompass short interfering RNAs (siRNAs). In one nonlimiting example, the first strand of the siRNA is antisense to the target nucleic acid, while the second strand is complementary to the first strand. Once the antisense strand is designed to target a particular nucleic acid target, the sense strand of the siRNA can then be designed and synthesized as the complement of the antisense strand and either strand may contain modifications or additions to either terminus. For example, in one embodiment, both strands of the siRNA duplex would be complementary over the central nucleobases, each having overhangs at one or both termini. It is possible for one end of a duplex to be blunt and the other to have overhanging nucleobases. In one embodiment, the number of overhanging nucleobases is from 1 to 6 on the 3' end of each strand of the duplex. In another embodiment, the number of overhanging nucleobases is from 1 to 6 on the 3' end of only one strand of the duplex. In a further embodiment, the number of overhanging nucleobases is from 1 to 6 on one or both 5' ends of the duplexed strands. In another embodiment, the number of overhanging nucleobases is zero.

In one embodiment of the invention, double-stranded antisense compounds are canonical siRNAs.

Each strand of the siRNA duplex may be from about 13 to about 80 nucleobases, 13 to 80, 13 to 50, 13 to 30, 13 to 24, 19 to 23, 20 to 80, 20 to 50, 20 to 30, or 20 to 24 nucleobases. The central complementary portion may be from about 8 to about 80 nucleobases in length, 10 to 50, 13 to 80, 13 to 50, 13 to 30, 13 to 24, 19 to 23, 20 to 80, 20 to 50, 20 to 30, or 20 to 24 nucleobases. The terminal portions can be from 1 to 6 nucleobases. The siRNAs may also have no terminal portions. The two strands of an siRNA can be linked internally leaving free 3' or 5' termini or can be linked to form a continuous hairpin structure or loop. The hairpin structure may contain an overhang on either the 5' or 3' terminus producing an extension of single-stranded character.

In another embodiment, the double-stranded antisense compounds are blunt-ended siRNAs. siRNAs whether canonical or blunt act to elicit dsRNAse enzymes and trigger the recruitment or activation of the RNAi antisense mechanism. In a further embodiment, single-stranded RNAi (ssRNAi) compounds that act via the RNAi antisense mechanism are contemplated.

Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, the compounds can take the form of a self-complementary hairpin-type molecule that doubles back on itself to form a duplex. Thus, the compounds can be fully or partially double-stranded. When formed from two strands, or a single strand that takes the form of a self-complementary hairpin-type molecule doubled back on itself to form a duplex, the two strands (or duplex-forming regions of a single strand) are complementary when they base pair in Watson-Crick fashion.

Contained within the oligomeric compounds of the invention (whether single or double stranded and on at least one strand) are antisense portions. The "antisense portion" is that part of the oligomeric compound that is designed to work by an antisense mechanism.

In one embodiment, the oligomeric compounds of the invention have antisense portions of 13 to 80 nucleobases. One having ordinary skill in the art will appreciate that this embodies oligomeric compounds having antisense portions of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the oligomeric compounds of the invention have antisense portions of 13 to 50 nucleobases. One having ordinary skill in the art will appreciate that this embodies oligomeric compounds having antisense portions of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the oligomeric compounds of the invention have antisense portions of 13 to 30 nucleobases. One having ordinary skill in the art will appreciate that this embodies oligomeric compounds having antisense portions of 13, 14, 15, 16, 17, 18, 19, 20, 21, 22, 23, 24, 25, 26, 27, 28, 29 or 30 nucleobases.

In some embodiments, the oligomeric compounds of the invention have antisense portions of 13 to 24 nucleobases. One having ordinary skill in the art will appreciate that this embodies oligomeric compounds having antisense portions of 13, 14, 15, 16, 17, 18, 19, 20, 21, 22, 23 or 24 nucleobases.

In one embodiment, the oligomeric compounds of the invention have antisense portions of 19 to 23 nucleobases. One having ordinary skill in the art will appreciate that this embodies oligomeric compounds having antisense portions of 19, 20, 21, 22 or 23 nucleobases.

In one embodiment, the oligomeric compounds of the invention have antisense portions of 20 to 80 nucleobases. One having ordinary skill in the art will appreciate that this embodies oligomeric compounds having antisense portions of 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the oligomeric compounds of the invention have antisense portions of 20 to 50 nucleobases. One having ordinary skill in the art will appreciate that this embodies oligomeric compounds having antisense portions of 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds of the invention have antisense portions of 20 to 30 nucleobases. One having ordinary skill in the art will appreciate that this embodies oligomeric compounds having antisense portions of 20, 21, 22, 23, 24, 25, 26, 27, 28, 29, or 30 nucleobases.

In one embodiment, the antisense compounds of the invention have antisense portions of 20 to 24 nucleobases. One having ordinary skill in the art will appreciate that this embodies oligomeric compounds having antisense portions of 20, 21, 22, 23, or 24 nucleobases.

In one embodiment, the oligomeric compounds of the invention have antisense portions of 20 nucleobases.

In one embodiment, the oligomeric compounds of the invention have antisense portions of 19 nucleobases.

In one embodiment, the oligomeric compounds of the invention have antisense portions of 18 nucleobases.

In one embodiment, the oligomeric compounds of the invention have antisense portions of 17 nucleobases.

In one embodiment, the oligomeric compounds of the invention have antisense portions of 16 nucleobases.

In one embodiment, the oligomeric compounds of the invention have antisense portions of 15 nucleobases.

In one embodiment, the oligomeric compounds of the invention have antisense portions of 14 nucleobases.

In one embodiment, the oligomeric compounds of the invention have antisense portions of 13 nucleobases.

Oligomeric compounds 13-80 nucleobases in length comprising a stretch of at least thirteen (13) consecutive nucleobases selected from within the illustrative antisense compounds are considered to be suitable antisense compounds as well.

Compounds of the invention include oligonucleotide sequences that comprise at least the thirteen consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about thirteen to about 80 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about thirteen to about 80 nucleobases). It is also understood that compounds may be represented by oligonucleotide sequences that comprise at least thirteen consecutive nucleobases from an internal portion of the sequence of an illustrative compound, and may extend in either or both directions until the oligonucleotide contains about 13 about 80 nucleobases.

One having skill in the art armed with the antisense compounds illustrated herein will be able, without undue experimentation, to identify further antisense compounds.

Phenotypic Assays

Once modulator compounds of glucose-6-phosphatase translocase have been identified by the methods disclosed herein, the compounds can be further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of glucose-6-phosphatase translocase in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the glucose-6-phosphatase translocase modulators. Hallmark genes, or those genes suspected to be associated with a specific disease state, condition, or phenotype, are measured in both treated and untreated cells.

Kits, Research Reagents, Diagnostics, and Therapeutics

The oligomeric compounds of the present invention can be utilized for diagnostics, therapeutics, prophylaxis and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the oligomeric compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions of the present invention are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Compounds of the invention can be used to modulate the expression of glucose-6-phosphatase translocase in an animal, such as a human. In one non-limiting embodiment, the methods comprise the step of administering to said animal an effective amount of an antisense compound that inhibits expression of glucose-6-phosphatase translocase. In one embodiment, the antisense compounds of the present invention effectively inhibit the levels or function of glucose-6-phosphatase translocase RNA. Because reduction in glucose-6-phosphatase translocase mRNA levels can lead to alteration in glucose-6-phosphatase translocase protein products of expression as well, such resultant alterations can also be measured. Antisense compounds of the present invention that effectively inhibit the levels or function of an glucose-6-phosphatase translocase RNA or protein products of expression is considered an active antisense compound. In one embodiment, the antisense compounds of the invention inhibit the expression of glucose-6-phosphatase translocase causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of glucose-6-phosphatase translocase, can be measured in a bodily fluid, tissue or organ of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues or organs include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues or organs can be routinely obtained by biopsy. In some alternative situations, samples of tissues or organs can be recovered from an animal after death.

The cells contained within said fluids, tissues or organs being analyzed can contain a nucleic acid molecule encoding glucose-6-phosphatase translocase protein and/or the glucose-6-phosphatase translocase-encoded protein itself. For example, fluids, tissues or organs procured from an animal can be evaluated for expression levels of the target mRNA or protein. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the target gene expression in the aforementioned fluids, tissues or organs, collected from an animal contacted with one or more compounds of the invention, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

The compounds of the present invention can be utilized in pharmaceutical compositions by adding an effective amount of a compound to a suitable pharmaceutically acceptable diluent or carrier. In one aspect, the compounds of the present invention selectively inhibit the expression of glucose-6-phosphatase translocase. The compounds of the invention can also be used in the manufacture of a medicament for the treatment of diseases and disorders related to glucose-6-phosphatase translocase expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of glucose-6-phosphatase translocase expression in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

In one embodiment, provided are uses of a compound of an isolated double stranded RNA oligonucleotide in the manufacture of a medicament for inhibiting glucose-6-phosphatase translocase expression or overexpression. Thus, provided herein is the use of an isolated double stranded RNA oligonucleotide targeted to glucose-6-phosphatase translocase in the manufacture of a medicament for the treatment of a disease or disorder by means of the method described above.

DEFINITIONS

"Antisense mechanisms" are all those involving hybridization of a compound with target nucleic acid, wherein the outcome or effect of the hybridization is either target degradation or target occupancy with concomitant stalling of the cellular machinery involving, for example, transcription or splicing.
Targets As used herein, the terms "target nucleic acid" and "nucleic acid molecule encoding glucose-6-phosphatase translocase" have been used for convenience to encompass DNA encoding glucose-6-phosphatase translocase, RNA (including pre-mRNA and mRNA or portions thereof) transcribed from such DNA, and also cDNA derived from such RNA.
Regions, Segments, and Sites The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as unique nucleobase positions within a target nucleic acid.

Once one or more target regions, segments or sites have been identified, oligomeric compounds are designed which are sufficiently complementary to the target, i.e., hybridize sufficiently well and with sufficient specificity, to give the desired effect.

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon." A minority of genes have a translation initiation codon having the RNA sequence 5' GUG, 5' UUG or 5' CUG, and 5' AUA, 5' ACG and 5' CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. "Start codon" and "translation initiation codon" refer to the codon or codons that are used in vivo to initiate translation of an mRNA transcribed from a gene encoding a protein, regardless of the sequence(s) of such codons. It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with oligomeric compounds of the invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the "5' untranslated region" (5'UTR, known in the art to refer to the portion of an mRNA in the 5' direction from the translation initiation codon, and thus including nucleotides between the 5' cap site and the translation initiation codon of an mRNA (or corresponding nucleotides on the gene), and the "3' untranslated region" (3'UTR), known in the art to refer to the portion of an mRNA in the 3' direction from the translation termination codon, and thus including nucleotides between the translation termination codon and 3' end of an mRNA (or corresponding nucleotides on the gene). The "5' cap site" of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region is also a target.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Consequently, the types of variants described herein are also suitable target nucleic acids.

Suitable Target Segments

The oligomeric compounds of the present invention can be targeted to features of a target nucleobase sequence, such as those described in Table 1. All regions of a nucleobase sequence to which an oligomeric compound can be targeted, wherein the regions are greater than or equal to 13 and less than or equal to 80 nucleobases, are described as follows:

Let R(m, n+m−1) be a region from a target nucleobase sequence, where "n" is the 5'-most nucleobase position of the region, where "n+m−1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 13 and is less than or equal to 80.

This set of regions can be represented using the following mathematical notation:

$$A = \bigcup_m S(m) \text{ where } m \in N | 13 \le m \le 80$$

and $$S(m) = \{R_{n,n+m-1} | n \in \{1, 2, 3, \ldots, L-m+1\}\}$$

where the mathematical operator | indicates "such that",
where the mathematical operator ∈ indicates "a member of a set" (e.g. y∈Z indicates that element y is a member of set Z),
where x is a variable,
where N indicates all natural numbers, defined as positive integers,
and where the mathematical operator ∪ indicates "the union of sets".

For example, the set of regions for m equal to 13, 20 and 80 can be constructed in the following manner. The set of regions, each 13 nucleobases in length, S(m=13), in a target nucleobase sequence 100 nucleobases in length (L=100), beginning at position 1 (n=1) of the target nucleobase sequence, can be created using the following expression:

$$S(13) = \{R_{1,13} | n \in \{1,2,3,\ldots,88\}\}$$

and describes the set of regions comprising nucleobases 1-13, 2-14, 3-15, 4-16, 5-17, 6-18, 7-19, 8-20, 9-21, 10-22, 11-23, 12-24, 13-25, 14-26, 15-27, 16-28, 17-29, 18-30, 19-31, 20-32, 21-33, 22-34, 23-35, 24-36, 25-37, 26-38, 27-39, 28-40, 29-41, 30-42, 31-43, 32-44, 33-45, 34-46, 35-47, 36-48, 37-49, 38-50, 39-51, 40-52, 41-53, 42-54, 43-55, 44-56, 45-57, 46-58, 47-59, 48-60, 49-61, 50-62, 51-63, 52-64, 53-65, 54-66, 55-67, 56-68, 57-69, 58-70, 59-71, 60-72, 61-73, 62-74, 63-75, 64-76, 65-77, 66-78, 67-79, 68-80, 69-81, 70-82, 71-83, 72-84, 73-85, 74-86, 75-87, 76-88, 77-89, 78-90, 79-91, 80-92, 81-93, 82-94, 83-95, 84-96, 85-97, 86-98, 87-99, 88-100.

An additional set for regions 20 nucleobases in length, in a target sequence 100 nucleobases in length, beginning at position 1 of the target nucleobase sequence, can be described using the following expression:

$$S(20) = \{R_{1,20} | n \in \{1,2,3,\ldots,81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80) = \{R_{1,80} | n \in \{1,2,3,\ldots,21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-13, 2-14, 3-15 . . . 88-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where ∪ represents the union of the sets obtained by combining all members of all sets.

The mathematical expressions described herein defines all possible target regions in a target nucleobase sequence of any length L, where the region is of length m, and where m is greater than or equal to 13 and less than or equal to 80 nucleobases and, and where m is less than L, and where n is less than L−m+1.

Validated Target Segments

Target segments can include DNA or RNA sequences that comprise at least the 13 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 13 to about 80 nucleobases). Similarly validated target segments are represented by DNA or RNA sequences that comprise at least the 13 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 13 to about 80 nucleobases). It is also understood that a validated oligomeric target segment can be represented by DNA or RNA sequences that comprise at least 13 consecutive nucleobases from an internal portion of the sequence of a validated target segment, and can extend in either or both directions until the oligonucleotide contains about 13 about 80 nucleobases.

The validated target segments identified herein can be employed in a screen for additional compounds that modulate the expression of glucose-6-phosphatase translocase. The screening method comprises the steps of contacting a validated target segment of a nucleic acid molecule encoding glucose-6-phosphatase translocase with one or more candidate modulators, and selecting for one or more candidate modulators which perturb the expression of a nucleic acid molecule encoding glucose-6-phosphatase translocase. Once it is shown that the candidate modulator or modulators are capable of modulating the expression of a nucleic acid molecule encoding glucose-6-phosphatase translocase, the modulator can then be employed in further investigative studies of the function of glucose-6-phosphatase translocase, or for use as a research, diagnostic, or therapeutic agent. The validated target segments can also be combined with a second strand as disclosed herein to form stabilized double-stranded (duplexed) oligonucleotides for use as a research, diagnostic, or therapeutic agent.

Modulation of Target Expression

"Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. "Modulators" are those compounds that modulate the expression of glucose-6-phosphatase translocase and which comprise at least a 13-nucleobase portion which is complementary to a validated target segment.

Modulation of expression of a target nucleic acid can be achieved through alteration of any number of nucleic acid (DNA or RNA) functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of glucose-6-phosphatase translocase. Thus, in one embodiment modulation of expression can mean increase or decrease in target RNA or protein levels. In another embodiment modulation of expression can mean an increase or decrease of one or more RNA splice products, or a change in the ratio of two or more splice products.

Hybridization and Complementarity

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances. An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least 70%, or at least 75%, or at least 80%, or at least 85%, or at least 90%, or at least 92%, or at least 95%, or at least 97%, or at least 98%, or at least 99% sequence complementarity to a target region within the target nucleic acid sequence to which they are targeted. For example, an oligomeric compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Oligomeric Compounds

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Non-limiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

As used herein, the term "siRNA" is defined as a double-stranded compound having a first and second strand and comprises a central complementary portion between said first and second strands and terminal portions that are optionally complementary between said first and second strands or with the target mRNA. The ends of the strands may be modified by the addition of one or more natural or modified nucleobases to form an overhang.

As used herein, the term "canonical siRNA" is defined as a double-stranded oligomeric compound having a first strand and a second strand each strand being 21 nucleobases in length with the strands being complementary over 19 nucleobases and having on each 3' termini of each strand a deoxy thymidine dimer (dTdT) which in the double-stranded compound acts as a 3' overhang.

As used herein the term "blunt-ended siRNA" is defined as an siRNA having no terminal overhangs. That is, at least one end of the double-stranded compound is blunt.

"Chimeric" oligomeric compounds or "chimeras," in the context of this invention, are single- or double-stranded oligomeric compounds, such as oligonucleotides, which contain two or more chemically distinct regions, each comprising at least one monomer unit, i.e., a nucleotide in the case of an oligonucleotide compound.

A "gapmer" is defined as an oligomeric compound, generally an oligonucleotide, having a 2'-deoxyoligonucleotide region flanked by non-deoxyoligonucleotide segments. The central region is referred to as the "gap." The flanking segments are referred to as "wings." If one of the wings has zero non-deoxyoligonucleotide monomers, a "hemimer" is described.

Chemical Modifications

Modified Internucleoside Linkages

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Specific examples of oligomeric compounds of the present invention include oligonucleotides containing modified e.g. non-naturally occurring internucleoside linkages. Oligomeric compounds can have one or more modified internucleoside linkages. Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate and thiophosphonoacetate (see Sheehan et al., *Nucleic Acids Research*, 2003, 31(14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Modified Sugars

Oligomeric compounds may also contain one or more substituted sugar moieties. Suitable compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are O(($CH_2$)$_n$O)$_m$$CH_3$, O($CH_2$)$_n$O$CH_3$, O($CH_2$)$_n$$NH_2$, O($CH_2$)$_n$$CH_3$, O($CH_2$)$_n$ONH$_2$, and O($CH_2$)$_n$ON(($CH_2$)$_n$$CH_3$)$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, O$NO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-β-$CH_2$$CH_2$O$CH_3$, also known as 2'-O-(2-methoxyethyl) or 2'-MOE) (Martin et al., *Helv. Chim. Acta*, 1995, 78, 486-504), i.e., an alkoxyalkoxy group. A further modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—($CH_2$)$_2$—O—($CH_2$)$_2$—N($CH_3$)$_2$, also described in examples hereinbelow.

Other modifications include 2'-methoxy (2'-O—$CH_3$), 2'-aminopropoxy (2'-O$CH_2$$CH_2$$CH_2$$NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

DNA-Like and RNA-Like Conformations

The terms used to describe the conformational geometry of homoduplex nucleic acids are "A Form" for RNA and "B Form" for DNA. In general, RNA:RNA duplexes are more stable and have higher melting temperatures (Tm's) than DNA:DNA duplexes (Sanger et al., *Principles of Nucleic Acid Structure,* 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger et al., *Principles of Nucleic Acid Structure,* 1984, Springer-Verlag; New York, N.Y.). As used herein, B-form geometry is inclusive of both C2'-endo pucker and O4'-endo pucker.

The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533). Consequently, compounds that favor an A-form geometry can enhance stacking interactions, thereby increasing the relative Tm and potentially enhancing a compound's antisense effect.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. Also provided herein are oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-β-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application.

The synthesis of numerous of the modified nucleosides amenable to the present invention are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

Oligonucleotide Mimetics

The term "mimetic" as it is applied to oligonucleotides includes oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA) (Nielsen et al., Science, 1991, 254, 1497-1500). PNAs have favorable hybridization properties, high biological stability and are electrostatically neutral molecules. PNA compounds have been used to correct aberrant splicing in a transgenic mouse model (Sazani et al., Nat. Biotechnol., 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligonucleotides which are less likely to form undesired interactions with cellular proteins (Dwaine A. Braasch and David R. Corey, Biochemistry, 2002, 41(14), 4503-4510). Morpholino-based oligomeric compounds have been studied in zebrafish embryos (see: Genesis, volume 30, issue 3, 2001 and Heasman, J., Dev. Biol., 2002, 243, 209-214). Further studies of morpholino-based oligomeric compounds have also been reported (Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N(CH$_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH$_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10° C.), stability towards 3'-exonucleolytic degradation and good solubility properties. LNA's are commercially available from ProLigo (Paris, France and Boulder, Colo., USA).

An isomer of LNA that has also been studied is alpha-L-LNA which has been shown to have superior stability against a 3'-exonuclease. The alpha-L-LNA's were incorporated into antisense gapmers and chimeras that showed potent antisense activity (Frieden et al., Nucleic Acids Research, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11° C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA-LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., *Proc. Natl. Acad. Sci. U.S.A.*, 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., *Proc. Natl. Acad. Sci.*, 2000, 97, 5633-5638) and in another study showed a blockage of the translation of the large subunit of RNA polymerase II (Fluiter et al., *Nucleic Acids Res.*, 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in *Chemical and Engineering News*, 2003, 81, 9). In another study it was determined that TNA is capable of antiparallel Watson-Crick base pairing with complementary DNA, RNA and TNA oligonucleotides (Chaput et al., *J. Am. Chem. Soc.*, 2003, 125, 856-857).

In one study (3',2')-alpha-L-threose nucleic acid was prepared and compared to the 2' and 3' amidate analogs (Wu et al., *Organic Letters*, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., *Helv. Chim. Acta*, 1997, 80, 2426-2439; Steffens et al., *J. Am. Chem. Soc.*, 1999, 121, 3249-3255; Renneberg et al., *J. Am. Chem. Soc.*, 2002, 124, 5993-6002; and Renneberg et al., *Nucleic acids res.*, 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of olignucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Modified and Alternate Nucleobases

The oligomeric compounds of the invention also include variants in which a different base is present at one or more of the nucleotide positions in the compound. For example, if the first nucleotide is an adenosine, variants may be produced which contain thymidine, guanosine or cytidine at this position. This may be done at any of the positions of the oligomeric compound. These compounds are then tested using the methods described herein to determine their ability to inhibit expression of glucose-6-phosphatase translocase mRNA.

Oligomeric compounds can also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). A "substitution" is the replacement of an unmodified or natural base with another unmodified or natural base. "Modified" nucleobases mean other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido (5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2 (3H)-one), carbazole cytidine (2H-pyrimido(4,5-b)indol-2-one), pyridoindole cytidine (H-pyrido(3',':4,5)pyrrolo[2,3-d] pyrimidin-2-one). Modified nucleobases may also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Oligomeric compounds of the present invention can also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., *Nucleosides and Nucleotides*, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 20030207804 and 20030175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° C. relative to 5-methyl cytosine (dC5$^{me}$), which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Pre-Grant Publication 20030158403.

Conjugates

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylaminocarbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582;

4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5' cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270). For siRNA constructs, the 5' end (5' cap) is commonly but not limited to 5'-hydroxyl or 5'-phosphate.

Particularly suitable 3'-cap structures include, for example 4',5'-methylene nucleotide; 1-(beta-D-erythrofuranosyl) nucleotide; 4'-thio nucleotide, carbocyclic nucleotide; 5'-aminoalkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target when bound by a DNA-like oligomeric compound, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNAseL which cleaves both cellular and viral RNA. Cleavage products of the RNA target can be routinely detected by gel electrophoresis and, if necessary, associated nucleic acid hybridization techniques known in the art.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

An example of a chimeric oligonucleotide is a gapmer having a 2'-deoxyoligonucleotide region flanked by non-deoxyoligonucleotide segments. While not wishing to be bound by theory, the gap of the gapmer presents a substrate recognizable by RNase H when bound to the RNA target whereas the wings do not provide such a substrate but can confer other properties such as contributing to duplex stability or advantageous pharmacokinetic effects. Each wing can be one or more non-deoxyoligonucleotide monomers. In one embodiment, the gapmer is a ten deoxynucleotide gap flanked by five non-deoxynucleotide wings. This is referred to as a 5-10-5 gapmer. Other configurations are readily recognized by those skilled in the art. In one embodiment the wings comprise 2'-MOE modified nucleotides. In another embodiment the gapmer has a phosphorothioate backbone. In another embodiment the gapmer has 2'-MOE wings and a phosphorothioate backbone. Other suitable modifications are readily recognizable by those skilled in the art.

NAFLD and Metabolic Syndrome

The term "nonalcoholic fatty liver disease" (NAFLD) encompasses a disease spectrum ranging from simple triglyceride accumulation in hepatocytes (hepatic steatosis) to hepatic steatosis with inflammation (steatohepatitis), fibrosis, and cirrhosis. Nonalcoholic steatohepatitis (NASH) occurs from progression of NAFLD beyond deposition of triglycerides. A second-hit capable of inducing necrosis, inflammation, and fibrosis is required for development of NASH. Candidates for the second-hit can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, *J. Clin. Invest.*, 2004, 114, 147-152). Hypertriglyceridemia and hyperfattyacidemia can cause triglyceride accumulation in peripheral tissues (Shimamura et al., *Biochem. Biophys. Res. Commun.*, 2004, 322, 1080-1085).

"Metabolic syndrome" is defined as a clustering of lipid and non-lipid cardiovascular risk factors of metabolic origin. It is closely linked to the generalized metabolic disorder known as insulin resistance. The National Cholesterol Education Program (NCEP) Adult Treatment Panel III (ATPIII) established citeria for diagnosis of metabolic syndrome when three or more of five risk determinants are present. The five risk determinants are abdominal obesity defined as waist circumference of greater than 102 cm for men or greater than 88 cm for women, triglyceride levels greater than or equal to 150 mg/dL, HDL cholesterol levels of less than 40 mg/dL for men and less than 50 mg/dL for women, blood pressure greater than or equal to 130/85 mm Hg and fasting glucose levels greater than or equal to 110 mg/dL. These determinants can be readily measured in clinical practice (*JAMA*, 2001, 285, 2486-2497).

HbA1c

HbA1c is a stable minor hemoglobin variant formed in vivo via posttranslational modification by glucose, and it contains predominantly glycated NH2-terminal β-chains. There is a strong correlation between levels of HbA1c and the average blood glucose levels over the previous 3 months. Thus HbA1c is often viewed as the "gold standard" for measuring sustained blood glucose control (Bunn, H. F. et al., 1978, Science. 200, 21-7). HbA1c can be measured by ion-exchange HPLC or immunoassay; home blood collection and mailing kits for HbA1c measurement are now widely available. Serum fructosamine is another measure of stable glucose control and can be measured by a colorimetric method (Cobas Integra, Roche Diagnostics).

Cardiovascular Risk Profile

Conditions associated with risk of developing a cardiovascular disease include, but are not limited to, history of myocardial infarction, unstable angina, stable angina, coronary artery procedures (angioplasty or bypass surgery), evidence of clinically significant myocardial ischemia, noncoronary forms of atherosclerotic disease (peripheral arterial disease, abdominal aortic aneurysm, carotid artery disease), diabetes, cigarette smoking, hypertension, low HDL cholesterol, family history of premature CHD, obesity, physical inactivity, elevated triglyceride, or metabolic syndrome (Jama, 2001, 285, 2486-2497; Grundy et al., Circulation, 2004, 110, 227-239).

Salts, Prodrugs and Bioequivalents

The oligomeric compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the oligomeric compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 or WO 94/2064.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 22 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoc acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Sodium salts of antisense oligonucleotides are useful and are well accepted for therapeutic administration to humans. In another embodiment, sodium salts of dsRNA compounds are also provided.

Formulations

The oligomeric compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The present invention also includes pharmaceutical compositions and formulations which include the antisense compounds of the invention. The pharmaceutical, compositions of the present invention may be administered in a number of ways depending upon whether local or systemic treatment is desired and upon the area to be treated. Administration may be topical (including but not limited to ophthalmic and to mucous membranes including vaginal and rectal delivery), pulmonary, e.g., by inhalation or insufflation of powders or aerosols, including by nebulizer (intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Sites of administration are known to those skilled in the art. Oligonucleotides with at least one 2'-O-methoxyethyl modification are believed to be useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Formulations for topical administration include those in which the oligomeric compounds of the invention are in admixture with a topical delivery agent such as lipids, liposomes, fatty acids, fatty acid esters, steroids, chelating agents and surfactants.

For topical or other administration, oligomeric compounds of the invention may be encapsulated within liposomes or may form complexes thereto, such as to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860. Topical formulations are described in detail in U.S. patent application Ser. No. 09/315,298 filed on May 20, 1999.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to affect the efficient delivery of oligomeric compounds, particularly oligonucleotides. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property.

Oral compositions for administration of non-parenteral oligomeric compounds can be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. Such oral oligomeric compound compositions can be referred to as "mucosal penetration enhancers."

Oligomeric compounds, such as oligonucleotides, may be delivered orally, in granular form including sprayed dried particles, or complexed to form micro or nanoparticles. Oligonucleotide complexing agents and their uses are further described in U.S. Pat. No. 6,287,860. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002.

In one embodiment, oral oligomeric compound compositions comprise at least one member of the group consisting of surfactants, fatty acids, bile salts, chelating agents, and non-chelating surfactants. Further embodiments comprise oral oligomeric compound comprising at least one fatty acid, e.g. capric or lauric acid, or combinations or salts thereof. One combination is the sodium salt of lauric acid, capric acid and UDCA.

In one embodiment, oligomeric compound compositions for oral delivery comprise at least two discrete phases, which phases may comprise particles, capsules, gel-capsules, microspheres, etc. Each phase may contain one or more oligomeric compounds, penetration enhancers, surfactants, bioadhesives, effervescent agents, or other adjuvant, excipient or diluent.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Oral oligomeric compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers.

One of skill in the art will recognize that formulations are routinely designed according to their intended use, i.e. route of administration.

Combinations

Compositions of the invention can contain two or more oligomeric compounds. In another related embodiment, compositions of the present invention can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially.

Combination Therapy

The compounds of the invention may be used in combination therapies, wherein an additive effect is achieved by administering one or more compounds of the invention and one or more other suitable therapeutic/prophylactic compounds to treat a condition. Suitable therapeutic/prophylactic compound(s) include, but are not limited to, glucose-lowering agents, anti-obesity agents, lipid lowering agents, or inhibitors of genes or gene products implicated in glucose and/or insulin metabolism, lipid and/or triglyceride levels, or obesity. Glucose lowering agents include, but are not limited to hormones or hormone mimetics (e.g., insulin, GLP-1 or a GLP-1 analog, exendin-4 or liraglutide), a sulfonylurea (e.g., acetohexamide, chlorpropamide, tolbutamide, tolazamide, glimepiride, a glipizide, glyburide, a micronized gylburide, or a gliclazide), a biguanide (metformin), a meglitinide (e.g., nateglinide or repaglinide), a thiazolidinedione or other PPAR-gamma agonist (e.g., pioglitazone, rosiglitazone, troglitazone, or isagitazone), dual-acting PPAR agonists with affinity for both PPAR-gamma and PPAR-alpha (e.g., BMS-298585 and tesaglitazar), an alpha-glucosidase inhibitor (e.g., acarbose or miglitol), or an antisense compound not targeted to glucose-6-phosphatase translocase. Glucose-lowering drugs already used in combined formulations are also suitable for use with compounds of the invention to achieve an additive effect. Anti-obesity agents include, but are not limited to, appetite suppressants (e.g. phentermine or Meridia™), fat absorption inhibitors such as orlistat (e.g. Xenical™), modified forms of ciliary neurotrophic factor which inhibit huger signals that stimulate appetite, or an antisense compound not targeted to glucose-6-phosphatase translocase. Lipid lowering agents include, but are not limited to, bile salt sequestering resins (e.g., cholestyramine, colestipol, and colesevelam hydrochloride), HMGCoA-reductase inhibitors (e.g., lovastatin, cerivastatin, prevastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), CETP inhibitors (e.g. torcetrapib and JTT-705) MTP inhibitors (eg, implitapide), inhibitors of bile acid transporters (apical sodium-dependent bile acid transporters), regulators of hepatic CYP7a, ACAT inhibitors (e.g. Avasimibe), estrogen replacement therapeutics (e.g., tamoxigen), synthetic HDL (e.g. ETC-216), anti-inflammatories (e.g., glucocorticoids), or an antisense compound not targeted to glucose-6-phosphatase translocase. Inhibitors of genes or gene products implicated in glucose and/or insulin metabolism, lipid and/or triglyceride levels, or obesity may include but are not limited to small molecules, antibodies, peptide fragments or antisense inhibitors (including ribozymes and siRNA molecules). One or more of these agents may be combined with one or more of the antisense inhibitors of glucose-6-phosphatase translocase to achieve an additive therapeutic effect. Combined compounds may be used together or sequentially.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Precursor Compounds

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-$N^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-

Dimethoxytrityl-2'-O-(2-methoxyethyl)-5-methylcytidine intermediate, 5'-O-dimethoxytrityl-2'-O-(2-methoxyethyl)-$N^4$-benzoyl-5-methylcytidine penultimate intermediate, (5'-O-(4,4'-Dimethoxytriphenylmethyl)-2'-O-(2-methoxyethyl)-$N^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-$N^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-$N^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl)nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., *Nucleic Acids Research*, 1993, 21, 3197-3203) using commercially available phosphoramidites (Glen Research, Sterling Va. or ChemGenes, Needham, Mass.).

2'-fluoro oligonucleotides can be synthesized routinely as described (Kawasaki, et. al., *J. Med. Chem.*, 1993, 36, 831-841) and U.S. Pat. No. 5,670,633.

2'-O-Methoxyethyl-substituted nucleoside amidites can be prepared routinely as per the methods of Martin, P., *Helvetica Chimica Acta*, 1995, 78, 486-504.

Aminooxyethyl and dimethylaminooxyethyl amidites can be prepared routinely as per the methods of U.S. Pat. No. 6,127,533.

Oligonucleotide Synthesis

Phosphorothioate-containing oligonucleotides (P=S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide Nucleic Acid Synthesis

Peptide nucleic acids (PNAs) can be prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, 5,719,262, 6,559,279 and 6,762,281.

Synthesis of 2'-O-Protected Oligomers/RNA Synthesis

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound.

A large number of 2'-O-protecting groups have been used for the synthesis of oligoribonucleotides and any can be used. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese et al. have identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach is to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group, initially used for the synthesis of oligoribonucleotides, is the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal. For example, the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number of structurally related formaldehyde acetal-derived, 2'-O-protecting groups. Also prepared were a number of related protecting groups for preparing 2'-O-alkylated nucleoside phosphoramidites including 2'-β-[(triisopropylsilyl)oxy]methyl (2'-O—CH$_2$—O—Si(iPr)$_3$, TOM). One T-O-protecting group that was prepared to be used orthogonally to the TOM group was 2'-O—[(R)-1-(2-nitrophenyl)ethyloxy)methyl] ((R)-mnbm).

Another strategy using a fluoride labile 5'-O-protecting group (non-acid labile) and an acid labile T-O-protecting group has been reported (Scaringe, Stephen A., Methods, 2001, (23) 206-217). A number of possible silyl ethers were examined for 5'-O-protection and a number of acetals and orthoesters were examined for T-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

The main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O—[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

Synthesis of Chimeric Oligomeric Compounds (2'-O-Me)-(2'-deoxy)-(2'-O-Me) Chimeric Phosphorothioate Oligonucleotides Chimeric oligonucleotides having 2'-O-alkyl phosphorothioate and 2'-deoxy phosphorothioate oligonucleotide segments can be routinely synthesized by one skilled in the art, using, for example, an Applied Biosystems automated DNA synthesizer Model 394. Oligonucleotides can be synthesized using an automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-O-alkyl portion. In one nonlimiting example, the standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligonucleotide is then recovered by an appropriate method (precipitation, column chromatography, volume reduced in vacuo) and analyzed by methods routine in the art.

(2'-O-(2-Methoxyethyl))-(2'-deoxy)-(2'-O-(2-Methoxyethyl)) Chimeric Phosphorothioate Oligonucleotides (2'-O-(2-methoxyethyl))-(2'-deoxy)-(-2'-O-(2-methoxyethyl)) chimeric phosphorothioate oligonucleotides can be prepared as per the procedure above for the 2'-O-methyl chimeric oligonucleotide, with the substitution of 2'-O-(methoxyethyl) amidites for the 2'; O-methyl amidites.

(2'-O-(2-Methoxyethyl)Phosphodiester)-(2'-deoxy Phosphorothioate)-(2'-O-(2-Methoxyethyl) Phosphodiester) Chimeric Oligonucleotides (2'-O-(2-methoxyethyl phosphodiester)-(2'-deoxy phosphorothioate)-(2'-β-(methoxyethyl) phosphodiester) chimeric oligonucleotides can be prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides can be synthesized according to U.S. Pat. No. 5,623,065.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates.

Nonlimiting Disclosure and Incorporation by Reference

While certain compounds, compositions and methods of the present invention have been described with specificity in accordance with certain embodiments, the examples herein serve only to illustrate the compounds of the invention and are not intended to limit the same. Each of the references, GENBANK® accession numbers, and the like recited in the present application is incorporated herein by reference in its entirety.

Example 1

Assaying Modulation of Expression

Modulation of glucose-6-phosphatase translocase expression can be assayed in a variety of ways known in the art. glucose-6-phosphatase translocase mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of proteins encoded by glucose-6-phosphatase translocase can be quantitated in a variety of ways well known in the art, such as immunoprecipitation, Western blot analysis (immunoblotting), ELISA or fluorescence-activated cell sorting (FACS). Antibodies directed to a protein encoded by glucose-6-phosphatase translocase can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

The effect of oligomeric compounds of the present invention on target nucleic acid expression can be tested in any of a variety of cell types provided that the target nucleic acid is present at measurable levels. The effect of oligomeric compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and include: Caco-2, D1 TNC1, SKBR-3, SK-MEL-28, TRAMP-C1, U937, undifferentiated 3T3-L1, 7F2, 7D4, A375, ARIP, AML-12, A20, A549, A10, A431, BLO-11, BC3H1, B16-F10, BW5147.3, BB88, BHK-21, BT-474, BEAS2B, C6, CMT-93, C3H/10T1/2, CHO-K1, ConA, C2C12, C3A, COS-7, CT26.WT, DDT1-MF2, DU145, D1B, E14, EMT-6, EL4, FAT7, GH1, GH3, G-361, HT-1080, HeLa, HCT116, H-4-II-E, HEK-293, HFN 36.3, HuVEC, HEPA1-6, H2.35, HK-2, Hep3B, HepG2, HuT 78, HL-60, H9c2(2-1), H9c2(2-1), IEC-6, IC21, JAR, JEG-3, Jurkat, K-562, K204, L2, LA4, LC-540, LLC1, LBRM-33, L6, LNcAP, LL2, MLg2908, MMT 060562, MH-S, MCF7, MDA MB231, MRC-5, M-3, Mia Paca, MLE12, MDA MB 468, MDA, NOR-10, NCTC 3749, N1S1, NBT-II, NIH/3T3, NC1-H292, NTERA-2 c1.D1, NIT-1, NCCIT, NR-8383, NRK, NG108-15, P388D1, PC-3, PANC-1, PC-12, P-19, P388D1 (IL-1), RFL-6, R2c, RK3E, Rin-M, Rin-5F, RBL-2H3, RMC, RAW264.7, Raji, Rat-2, SV40 MES13, SMT/2A LNM, SW480, TCMK-1, THLE-3, TM-3, TM4, T3-3A1, T47D, T-24, THP-1, UMR-106, U-87 MG, U-2OS, VERO C1008, WISH, WEHI 231, Y-1, YB2/0, Y13-238, Y13-259, Yac-1, b.END, mIMCD-3, sw872 and 70Z3. Additional cell lines, such as HuH-7 and U373, can be obtained from the Japanese Cancer Research Resources Bank (Tokyo, Japan) and the Centre for Applied Microbiology and Research (Wiltshire, United Kingdom), respectively.

Primary cells, or those cells which are isolated from an animal and not subjected to continuous culture, can be prepared according to methods known in the art or obtained from various commercial suppliers. Additionally, primary cells include those obtained from donor human subjects in a clinical setting (i.e. blood donors, surgical patients). Primary cells prepared by methods known in the art include: mouse or rat bronchoalveolar lavage cells, mouse primary bone marrow-derived osteoclasts, mouse primary keratinocytes, human primary macrophages, mouse peritoneal macrophages, rat peritoneal macrophages, rat primary neurons, mouse primary osteoblasts, rat primary osteoblasts, rat cerebellum tissue cells, rat cerebrum tissue cells, rat hippocampal tissue cells, mouse primary splenocytes, human synoviocytes, mouse synoviocytes and rat synoviocytes. Additional types of primary cells, including human primary melanocytes, human primary monocytes, NHDC, NHDF, adult NHEK, neonatal NHEK, human primary renal proximal tubule epithelial cells, mouse embryonic fibroblasts, differentiated adipocytes, HASMC, HMEC, HMVEC-L, adult HMVEC-D, neonatal HMVEC-D, HPAEC, human primary hepatocytes, monkey primary hepatocytes, mouse primary hepatocytes, hamster primary hepatocytes, rabbit primary hepatocytes and rat primary hepatocytes, can be obtained from commercial suppliers such as Stem Cell Technologies; Zen-Bio, Inc. (Research Triangle Park, N.C.); Cambrex Biosciences (Walkersville, Md.); In Vitro Technologies (Baltimore, Md.); Cascade Biologics (Portland, Oreg.); Advanced Biotechnologies (Columbia, Md.).

Cell Types

The effect of oligomeric compounds on target nucleic acid expression was tested in one or more of the following cell types.

Hepatocytes, Mouse Primary:

Primary mouse hepatocytes were prepared from CD-1 mice purchased from Charles River Labs. Primary mouse hepatocytes were routinely cultured in Hepatocyte Attachment Media supplemented with 10% fetal bovine serum (Invitrogen Life Technologies, Carlsbad, Calif.), 250 nM dexamethasone, and 10 nM bovine insulin (Sigma-Aldrich, St. Louis, Mo.). Cells were seeded into 96-well plates (Falcon-Primaria #353872, BD Biosciences, Bedford, Mass.) at a density of approximately 4,000-6,000 cells/well for use in oligomeric compound transfection experiments.

HepG2:

The human hepatoblastoma cell line HepG2 was obtained from the American Type Culture Collection (Manassas, Va.). HepG2 cells were routinely cultured in Eagle's MEM supplemented with 10% fetal bovine serum, 1 mM non-essential amino acids, and 1 mM sodium pyruvate (Invitrogen Life Technologies, Carlsbad, Calif.). Cells were routinely passaged by trypsinization and dilution when they reached approximately 90% confluence. Multiwell culture plates are prepared for cell culture by coating with a 1:100 dilution of type 1 rat tail collagen (BD Biosciences, Bedford, Mass.) in phosphate-buffered saline. The collagen-containing plates were incubated at 37° C. for approximately 1 hour, after which the collagen was removed and the wells were washed twice with phosphate-buffered saline. Cells were seeded into 96-well plates (Falcon-Primaria #353872, BD Biosciences, Bedford, Mass.) at a density of approximately 8,000 cells/well for use in oligomeric compound transfection experiments.

T-24:

The transitional cell bladder carcinoma cell line T-24 was obtained from the American Type Culture Collection (ATCC) (Manassas, Va.). T-24 cells were routinely cultured in complete McCoy's 5A basal media (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 4000-6000 cells/well for use in oligomeric compound transfection experiments.

Treatment with Oligomeric Compounds

When cells reach appropriate confluency, they were treated with oligonucleotide using a transfection method as described.

LIPOFECTIN™

When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 μg/mL per 100 nM oligonucleotide. This transfection mixture was incubated at room temperature for approximately 0.5 hours. For cells grown in 96-well plates, wells were washed once with 100 μL OPTI-MEM™-1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

CYTOFECTIN™

When cells reached 65-75% confluency, they were treated with oligonucleotide. Oligonucleotide was mixed with CYTOFECTIN™ (Gene Therapy Systems, San Diego, Calif.) in OPTI-MEM™-1 reduced serum medium (Invitrogen Life Technologies, Carlsbad, Calif.) to achieve the desired concentration of oligonucleotide and a CYTOFECTIN™ concentration of 2 or 4 μg/mL per 100 nM oligonucleotide. This transfection mixture was incubated at room temperature for approximately 0.5 hours. For cells grown in 96-well plates, wells were washed once with 100 μL OPTI-MEM™-1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

LIPOFECTAMINE™

When cells reached 65-75% confluency, they were treated with oligonucleotide. Oligonucleotide was mixed with LIPOFECTAMINE™ (Invitrogen Life Technologies, Carlsbad, Calif.) in OPTI-MEM™-1 reduced serum medium (Invitrogen Life Technologies, Carlsbad, Calif.) to achieve the desired concentration of oligonucleotide and a Lipofectamine™ concentration of ranging from 2 to 12 μg/mL per 100 nM oligonucleotide. This transfection mixture was incubated at room temperature for approximately 0.5 hours. For cells grown in 96-well plates, wells were washed once with 100 μL OPTI-MEM™-1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh medium. Cells were harvested 16-24 hours after oligonucleotide treatment.

OLIGOFECTAMINE™

When cells reached 65-75% confluency, they were treated with oligonucleotide. Oligonucleotide was mixed with OLIGOFECTAMINE™ (Invitrogen Life Technologies, Carlsbad, Calif.) in OPTI-MEM™-1 reduced serum medium (Invitrogen Life Technologies, Carlsbad, Calif.) to achieve the desired concentration of oligonucleotide with an OLIGOFECTAMINE™ to oligonucleotide ratio of approximately 0.2 to 0.8 μL per 100 nM. This transfection mixture was incubated at room temperature for approximately 0.5 hours. For cells grown in 96-well plates, wells were washed once with 100 μl, OPTI-MEM™-1 and then treated with 100 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh medium. Cells were harvested 16-24 hours after oligonucleotide treatment.

FUGENE™

Oligomeric compounds were introduced into the cells using the non-liposomal transfection reagent FUGENE 6 (Roche Diagnostics Corp., Indianapolis, Ind.). Oligomeric compound was mixed with FUGENE 6 in 1 mL of serum-free RPMI to achieve the desired concentration of oligonucleotide with a FUGENE 6 to oligomeric compound ratio of 1 to 4 μl, of FUGENE 6 per 100 nM. The oligomeric compound/FUGENE 6 complex was allowed to form at room temperature for 20 minutes. For cells grown in 96-well plates, wells were washed once with 100 μL OPTI-MEM™-1 and then treated with 100 μl, of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh medium. Cells were harvested 16-24 hours after oligonucleotide treatment.

Electroporation

When cells reached approximately 80% confluency, oligonucleotide was introduced via electroporation. Oligonucleotide concentrations used in electroporation experiments range from 1 to 40 µM. Cells were harvested by routine trypsinization to produce a single cell suspension. Following cell counting using a hemocytometer and pelleting by centrifugation, cells were resuspended in OPTI-MEM™-1 reduced serum medium (Invitrogen Life Technologies, Carlsbad, Calif.) to achieve a density of 1×107 cells/mL. Cells were mixed with the desired concentration of oligonucleotide and transferred to a 0.1 cm electroporation cuvette (BTX Molecular Delivery Systems, Hollister, Mass.). Cells were subjected to a single pulse using an electroporation apparatus (for example, the BTX Electro Square Porator T820 or the BTX HT300, BTX Molecular Delivery Systems, Hollister, Mass.), diluted into culture medium and plated into 24-well plates. Cells were treated and data were obtained in duplicate or triplicate. Approximately 24 hours following electroporation, cells were harvested.

Control Oligonucleotides

Control oligonucleotides are used to determine the optimal oligomeric compound concentration for a particular cell line. Furthermore, when oligomeric compounds of the invention are tested in oligomeric compound screening experiments or phenotypic assays, control oligonucleotides are tested in parallel with compounds of the invention. In some embodiments, the control oligonucleotides are used as negative control oligonucleotides, i.e., as a means for measuring the absence of an effect on gene expression or phenotype. In alternative embodiments, control oligonucleotides are used as positive control oligonucleotides, i.e., as oligonucleotides known to affect gene expression or phenotype. Control oligonucleotides are shown in Table 2. "Target Name" indicates the gene to which the oligonucleotide is targeted. "Species of Target" indicates species in which the oligonucleotide is perfectly complementary to the target mRNA. "Motif" is indicative of chemically distinct regions comprising the oligonucleotide. Certain compounds in Table 2 are composed of 2'-O-(2-methoxyethyl) nucleotides, also known as 2'-MOE nucleotides, and are designated as "Uniform MOE". Certain compounds in Table 2 are chimeric oligonucleotides, composed of a central "gap" region consisting of 2'-deoxynucleotides, which is flanked on both sides (5' and 3') by "wings". The wings are composed of 2'-O-(2-methoxyethyl) nucleotides, also known as 2'-MOE nucleotides. The "motif" of each gapmer oligonucleotide is illustrated in Table 2 and indicates the number of nucleotides in each gap region and wing, for example, "5-10-5" indicates a gapmer having a 10-nucleotide gap region flanked by 5-nucleotide wings. Similarly, the motif "5-9-6" indicates a 9-nucleotide gap region flanked by 5-nucleotide wing on the 5' side and a 6-nucleotide wing on the 3' side. ISIS 29848 is a mixture of randomized oligomeric compound; its sequence is shown in Table 2, where N can be A, T, C or G. The internucleoside (backbone) linkages are phosphorothioate throughout the oligonucleotides in Table 2. Unmodified cytosines are indicated by ""C" in the nucleotide sequence; all other cytosines are 5-methylcytosines.

TABLE 2

Control oligonucleotides for cell line testing, oligomeric compound screening and phenotypic assays

| ISIS # | Target Name | Species of Target | Sequence (5' to 3') | Motif | SEQ ID NO |
|---|---|---|---|---|---|
| 113131 | CD86 | Human | CGTGTGTCTGTGCTAGTCCC | 5-10-5 | 5 |
| 289865 | forkhead box O1A (rhabdomyosarcoma) | Human | GGCAACGTGAACAGGTCCAA | 5-10-5 | 6 |
| 25237 | integrin beta 3 | Human | GCCCATTGCTGGACATGC | 4-10-4 | 7 |
| 196103 | integrin beta 3 | Human | AGCCCATTGCTGGACATGCA | 5-10-5 | 8 |
| 148715 | Jagged 2 | Human; Mouse; Rat | TTGTCCCAGTCCCAGGCCTC | 5-10-5 | 9 |
| 18076 | Jun N-Terminal Kinase-1 | Human | CTTTC"CGTTGGA"C"CCCTGGG | 5-9-6 | 10 |
| 18078 | Jun N-Terminal Kinase-2 | Human | GTGCG"CG"CGAG"C"C"CGAAATC | 5-9-6 | 11 |
| 183881 | kinesin-like 1 | Human | ATCCAAGTGCTACTGTAGTA | 5-10-5 | 12 |
| 29848 | none | none | NNNNNNNNNNNNNNNNNNNN | 5-10-5 | 13 |
| 226844 | Notch (Drosophila) homolog 1 | Human; Mouse | GCCCTCCATGCTGGCACAGG | 5-10-5 | 14 |
| 105990 | Peroxisome proliferator-activated receptor gamma | Human | AGCAAAAGATCAATCCGTTA | 5-10-5 | 15 |
| 336806 | Raf kinase C | Human | TACAGAAGGCTGGGCCTTGA | 5-10-5 | 16 |
| 15770 | Raf kinase C | Mouse; Murine sarcoma virus; Rat | ATGCATT"CTG"C"C"C"CAAGGA | 5-10-5 | 17 |

The concentration of oligonucleotide used varies from cell line to cell line. To determine the optimal oligonucleotide concentration for a particular cell line, the cells are treated with a positive control oligonucleotide at a range of concentrations. Positive controls are shown in Table 2. For human and non-human primate cells, the positive control oligonucleotide is selected from ISIS 13650 or ISIS 18078. For mouse or rat cells the positive control oligonucleotide is ISIS 15770 or ISIS 15346. The concentration of positive control oligonucleotide that results in 80% inhibition of the target mRNA, for example, human Raf kinase C for ISIS 13650, is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 1 μM to 40 μM when the antisense oligonucleotide is transfected by electroporation.

Example 2

Real-Time Quantitative PCR Analysis of Glucose 6-Phosphatase Translocase mRNA Levels Quantitation of glucose 6-phosphatase translocase mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 μL PCR cocktail (2.5×PCR buffer minus MgCl$_2$, 6.6 mM MgCl$_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 μL of RiboGreen™ working reagent (RiboGreen™ reagent diluted 1:350 in 10 mM Tris-HCl, 1 mM EDTA, pH 7.5) was pipetted into a 96-well plate containing 30 μL purified cellular RNA. The plate was read in a CytoFluor 4000 (PE Applied Biosystems) with excitation at 485 nm and emission at 530 nm.

Presented in Table 3 are primers and probes which may be used to measure GAPDH expression in the cell types described herein. The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

TABLE 3

GAPDH primers and probes for use in real-time PCR

| Species | Sequence Description | Sequence (5' to 3') | SEQ ID NO |
|---|---|---|---|
| Human | Forward Primer | GAAGGTGAAGGTCGGAGTC | 18 |
| Human | Reverse Primer | GAAGATGGTGATGGGATTTC | 19 |
| Human | Probe | CAAGCTTCCCGTTCTCAGCC | 20 |
| Mouse | Forward Primer | GGCAAATTCAACGGCACAGT | 21 |
| Mouse | Reverse Primer | GGGTCTCGCTCCTGGAAGAT | 22 |
| Mouse | Probe | AAGGCCGAGAATGGGAAGCTTGTCATC | 23 |

Example 3

Antisense Inhibition of Human Glucose-6-Phosphatase Translocase Expression by Oligomeric Compounds A series of oligomeric compounds was designed to target different regions of human glucose-6-phosphatase translocase, using published sequences cited in Table 1. The compounds are shown in Table 4. All compounds in Table 4 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the following primer-probe set designed to hybridize to human glucose-6-phosphatase translocase: Forward primer: GGGCACTGTGTGTGGTTGTC (incorporated herein as SEQ ID NO: 24) Reverse primer: GAGTCCAACATCAGCAGGTTCA (incorporated herein as SEQ ID NO: 25) And the PCR probe was: FAM-CCTTCCTCTGTCTCCTGCTCATCCACA-TAMRA (incorporated herein as SEQ ID NO: 26), where FAM is the fluorescent dye and TAMRA is the quencher dye.

Data are from experiments in which T-24 cells were treated with 100 nM of the antisense oligonucleotides of the present invention using LIPOFECTIN™. A reduction in expression is expressed as percent inhibition in Table 4. If present, "N.D." indicates "not determined". The control oligomeric compound used was SEQ ID NO: 11. The target regions to which these oligomeric compounds are inhibitory are herein referred to as "validated target segments."

TABLE 4

Inhibition of human glucose-6-phosphatase translocase mRNA levels by chimeric oligonucleotides having 2'-MOE wings and deoxy gap

| ISIS # | Region | Target SEQ ID NO | Target Site | Sequence (5' to 3') | % Inhib | SEQ ID NO |
|---|---|---|---|---|---|---|
| 194825 | Stop Codon | 1 | 1449 | GGACTCTCTTCACTCAGCCT | 73 | 27 |
| 194826 | Coding | 1 | 1407 | GGTGCGGATGTTTCGTAGGA | 76 | 28 |
| 194827 | Coding | 1 | 306 | GATGAACCCCAAATCATCCT | 55 | 29 |
| 194828 | 3'UTR | 1 | 1815 | CATTAGTGCCCTGCAGCTGC | 73 | 30 |
| 194829 | 3'UTR | 1 | 1931 | TGCGCCTAGTGGTACAGTGA | 82 | 31 |
| 194830 | Coding | 1 | 436 | AGGCAAAGAATATGTTGACC | 68 | 32 |
| 194831 | Coding | 1 | 1053 | ATGGCGAGGGTTCCCGTAGT | 54 | 33 |
| 194832 | Coding | 1 | 666 | AGATAGGGCCAGCGTGCTGC | 55 | 34 |
| 194833 | Coding | 1 | 848 | TAACCAGTGGAGAGCACCCA | 60 | 35 |
| 194834 | Coding | 1 | 924 | TGACTGTCCTTTCTCCTGGA | 71 | 36 |
| 194835 | Coding | 1 | 215 | CTGTAGCCCCCAAACATGGC | 59 | 37 |
| 194836 | 3'UTR | 1 | 1792 | GATAGCCTCACTTCAGGTGG | 58 | 38 |
| 194837 | 3'UTR | 1 | 1945 | CACCTATATCCAACTGCGCC | 81 | 39 |
| 194838 | 3'UTR | 1 | 1710 | TGACTGCAGAAGTTTCCTGT | 91 | 40 |
| 194839 | 3'UTR | 1 | 1946 | CCACCTATATCCAACTGCGC | 83 | 41 |
| 194840 | Coding | 1 | 957 | CAGGGCACTCATGTAGGAGC | 51 | 42 |
| 194841 | Coding | 1 | 274 | TCTCTTCCACCAATGATGGC | 41 | 43 |
| 194842 | Coding | 1 | 290 | TCCTTGTCCAAAGGGATCTC | 57 | 44 |
| 194843 | Coding | 1 | 651 | GCTGCGCCAGCTGTAGCTCT | 66 | 45 |
| 194844 | 5'UTR | 1 | 97 | CCTGCTTGCCGCTCTCACAG | 73 | 46 |
| 194845 | 5'UTR | 1 | 99 | TTCCTGCTTGCCGCTCTCAC | 50 | 47 |
| 194846 | Coding | 1 | 621 | GGTTGCCAGGATAGGGCCCA | 70 | 48 |
| 194847 | Coding | 1 | 1317 | CTTGGCAATGGTGCTGAAGG | 66 | 49 |
| 194848 | 3'UTR | 1 | 1925 | TAGTGGTACAGTGAGAATGA | 81 | 50 |
| 194849 | Coding | 1 | 979 | TGCCTACAAGGCCCCCAACT | 65 | 51 |
| 194850 | Coding | 1 | 354 | CCCACTGACAAACTTGCTGA | 88 | 52 |
| 194851 | 5'UTR | 1 | 80 | CAGTTCCCAGATCTGCTGAG | 73 | 53 |
| 194852 | Coding | 1 | 920 | TGTCCTTTCTCCTGGATAAG | 44 | 54 |
| 194853 | Coding | 1 | 684 | AACCACACACAGTGCCCCAG | 35 | 55 |

TABLE 4-continued

Inhibition of human glucose-6-phosphatase translocase mRNA levels by chimeric oligonucleotides having 2'-MOE wings and deoxy gap

| ISIS # | Region | Target SEQ ID NO | Target Site | Sequence (5' to 3') | % Inhib | SEQ ID NO |
|---|---|---|---|---|---|---|
| 194854 | 3'UTR | 1 | 1824 | GTCAAGGGTCATTAGTGCCC | 80 | 56 |
| 194855 | Coding | 1 | 800 | AGGGTGCTCTCCTCCTTCAA | 57 | 57 |
| 194856 | 5'UTR | 1 | 102 | CAGTTCCTGCTTGCCGCTCT | 56 | 58 |
| 194857 | Coding | 1 | 1399 | TGTTTCGTAGGAGGAAGAAG | 44 | 59 |
| 194858 | 3'UTR | 1 | 1523 | CCAGGCAGGCCCCTCCTTTT | 71 | 60 |
| 194859 | Coding | 1 | 926 | GCTGACTGTCCTTTCTCCTG | 62 | 61 |

Example 4

Design and Screening of Duplexed Oligomeric Compounds Targeting Glucose-6-Phosphatase Translocase In accordance with the invention, a series of duplexes, including dsRNA and mimetics thereof, comprising oligomeric compounds of the invention and their complements can be designed to target glucose-6-phosphatase translocase. The nucleobase sequence of the antisense strand of the duplex comprises at least a portion of an oligonucleotide targeted to glucose-6-phosphatase translocase as disclosed herein. The ends of the strands may be modified by the addition of one or more natural or modified nucleobases to form an overhang. The sense strand of the nucleic acid duplex is then designed and synthesized as the complement of the antisense strand and may also contain modifications or additions to either terminus. The antisense and sense strands of the duplex comprise from about 17 to 25 nucleotides, or from about 19 to 23 nucleotides. Alternatively, the antisense and sense strands comprise 20, 21 or 22 nucleotides.

For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (incorporated herein as SEQ ID NO: 62) and having a two-nucleobase overhang of deoxythymidine (dT) would have the following structure:

```
cgagaggcggacgggaccgTT     Antisense Strand
||||||||||||||||||||      (SEQ ID NO: 63)
TTgctctccgcctgccctggc     Complement
                          (SEQ ID NO: 64)
```

Overhangs can range from 2 to 6 nucleobases and these nucleobases may or may not be complementary to the target nucleic acid. In another embodiment, the duplexes can have an overhang on only one terminus.

In another embodiment, a duplex comprising an antisense strand having the same sequence, for example CGAGAGGCGGACGGGACCG (SEQ ID NO: 62), can be prepared with blunt ends (no single stranded overhang) as shown:

```
cgagaggcggacgggaccg       Antisense Strand
|||||||||||||||||||       (SEQ ID NO: 62)
gctctccgcctgccctggc       Complement
                          (SEQ ID NO: 65)
```

The RNA duplex can be unimolecular or bimolecular; i.e., the two strands can be part of a single molecule or may be separate molecules.

RNA strands of the duplex can be synthesized by methods routine to the skilled artisan or purchased from Dharmacon Research Inc. (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM.

Once prepared, the duplexed compounds are evaluated for their ability to modulate glucose-6-phosphatase translocase. When cells reached 80% confluency, they are treated with duplexed compounds of the invention. For cells grown in 96-well plates, wells are washed once with 200 µL, OPTI-MEM-1™ reduced-serum medium (Gibco BRL) and then treated with 130 µl, of OPTI-MEM-1™ containing 12 µg/mL LIPOFECTIN™ (Gibco BRL) and the desired duplex antisense compound at a final concentration of 200 nM (a ratio of 6 µg/mL LIPOFECTIN™ per 100 nM duplex antisense compound). After 5 hours of treatment, the medium is replaced with fresh medium. Cells are harvested 16 hours after treatment, at which time RNA is isolated and target reduction measured by RT-PCR.

Example 5

Antisense Inhibition of Mouse Glucose-6-Phosphatase Translocase Expression by Oligomeric Compounds A series of oligomeric compounds was designed to target different regions of mouse glucose-6-phosphatase translocase, using published sequences cited in Table 1. The compounds are shown in Table 5. All compounds in Table 5 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the following primer-probe set designed to hybridize to mouse glucose-6-phosphatase translocase:

forward primer: GAAGGCAGGGCTGTCTCTGTAT (SEQ ID NO: 66)

reverse primer: CCATCCCAGCCATCATGAG (SEQ ID NO: 67)

and the PCR probe was: FAM-AACCCTCGCCACGGC-CTATTGC-TAMRA (SEQ ID NO: 68) where FAM is the fluorescent reporter dye and TAMRA is the quencher dye. Mouse target gene quantities were normalized by quantifying total RNA using RIBOGREEN™.

Data are from experiments in which primary mouse hepatocytes were treated with 50 nM of the antisense oligonucleotides of the present invention. A reduction in expression is expressed as percent inhibition in Table 5. If present, "N.D." indicates "not determined". The target regions to which these oligomeric compounds are inhibitory are herein referred to as "validated target segments."

TABLE 5

Inhibition of mouse glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|--------|------------------|-------------|---------------------|---------|-----------|
| 148936 | 3 | 13 | TGCCTGGATCTGCTGAGCTG | 39 | 69 |
| 148937 | 3 | 22 | TCTCTTTAGTGCCTGGATCT | 52 | 70 |
| 148938 | 3 | 45 | GACTGCTCCTGCTTGCAGCT | 50 | 71 |
| 148939 | 3 | 56 | CACAGACTCTTGACTGCTCC | 41 | 72 |
| 148940 | 3 | 83 | CTGCTGGCCCACTCCAGTAC | 61 | 73 |
| 148941 | 3 | 120 | CCGTAGCCTTGGGCTGCCAT | 62 | 74 |
| 148942 | 3 | 147 | GCCGCAAATATGACAGTGCG | 17 | 75 |
| 148943 | 3 | 201 | ACAAAGGAGAAGGTTTTGCG | 47 | 76 |
| 148944 | 3 | 232 | CAGAGCGATCTCATCCACCA | 35 | 77 |
| 148945 | 3 | 238 | CTTGTCCAGAGCGATCTCAT | 35 | 78 |
| 148946 | 3 | 243 | TCGTCCTTGTCCAGAGCGAT | 70 | 79 |
| 148947 | 3 | 253 | GAGCCCCAAATCGTCCTTGT | 37 | 80 |
| 148948 | 3 | 258 | GTGATGAGCCCCAAATCGTC | 52 | 81 |
| 148949 | 3 | 266 | GGCTGCTTGTGATGAGCCCC | 52 | 82 |
| 148950 | 3 | 288 | CTGATGGCGTAGGCTGCCGA | 0 | 83 |
| 148951 | 3 | 301 | GCTCACAAACTTGCTGATGG | 57 | 84 |
| 148952 | 3 | 432 | CCATTAAGAAACCAAGGAGC | 20 | 85 |
| 148953 | 3 | 447 | AGCCCCTGTGCCAGACCATT | 58 | 86 |
| 148954 | 3 | 504 | CCAAACTGGGATGGCTCAAA | 48 | 87 |
| 148955 | 3 | 536 | TCATGCTGGTTGACAACACA | 36 | 88 |
| 148956 | 3 | 554 | CCAAACTTCCAGCCAGGTTC | 27 | 89 |
| 148957 | 3 | 609 | GCCAGTGTGCTGCGCCAGCT | 57 | 90 |
| 148958 | 3 | 614 | ACAGGGCCAGTGTGCTGCGC | 50 | 91 |
| 148959 | 3 | 706 | CAGAGGGTCCAGATTTCGGA | −6 | 92 |
| 148960 | 3 | 795 | CCAGTGGACAGCACCCAGAG | 28 | 93 |
| 148961 | 3 | 809 | AGACCACAAGGTAGCCAGTG | 36 | 94 |
| 148962 | 3 | 830 | TACAGCAAGTCTTTACTCCG | 47 | 95 |
| 148963 | 3 | 841 | GCCCCAGTCTGTACAGCAAG | 55 | 96 |

TABLE 5-continued

Inhibition of mouse glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 148964 | 3 | 886 | ACCCACAAGGGCGGACTGCC | 0 | 97 |
| 148965 | 3 | 891 | GAGCTACCCACAAGGGCGGA | 16 | 98 |
| 148966 | 3 | 904 | GGCACTGATGTAGGAGCTAC | 54 | 99 |
| 148967 | 3 | 922 | AAGGCCTCCGACCTCGAGGG | 34 | 100 |
| 148968 | 3 | 934 | AATGCTTCCTACAAGGCCTC | 26 | 101 |
| 148969 | 3 | 967 | CGCCATGGCCCTGTCTGACA | 24 | 102 |
| 148970 | 3 | 986 | ACAGAGACAGCCCTGCCTTC | 78 | 103 |
| 148971 | 3 | 999 | CGAGGGTTCCCATACAGAGA | 88 | 104 |
| 148972 | 3 | 1010 | ATAGGCCGTGGCGAGGGTTC | 36 | 105 |
| 148973 | 3 | 1027 | AGCCATCATGAGTAGCAATA | 35 | 106 |
| 148974 | 3 | 1060 | TACTCGGAAGAGATACGTGG | 8 | 107 |
| 148975 | 3 | 1086 | ATCTTGGGTGAGTCACTGGT | 42 | 108 |
| 148976 | 3 | 1099 | AACCAGGATCCAGATCTTGG | 48 | 109 |
| 148977 | 3 | 1111 | CACGGCTCCCAAAACCAGGA | 9 | 110 |
| 148978 | 3 | 1194 | GAGGTTCCACACAAGTTGGG | 34 | 111 |
| 148979 | 3 | 1198 | ATGAGAGGTTCCACACAAGT | 54 | 112 |
| 148980 | 3 | 1255 | GCTGAAGGGTAAGCCAGCCA | 43 | 113 |
| 148981 | 3 | 1285 | TGTGCTCCAGCTATAGTGCT | 59 | 114 |
| 148982 | 3 | 1329 | ACAACTGTGCTGGCTCCACA | 69 | 115 |
| 148983 | 3 | 1352 | GGATATTTCGAAGCAAGAAG | 43 | 116 |
| 148984 | 3 | 1390 | TCACTCTCCCTTCTTGGATA | 60 | 117 |
| 148985 | 3 | 1411 | GCTCCATAGCGAGGACTCGA | 84 | 118 |
| 148986 | 3 | 1444 | CCGTGTCCTGCCAGTAAGGC | 55 | 119 |
| 148987 | 3 | 1448 | CTTTCCGTGTCCTGCCAGTA | 45 | 120 |
| 148988 | 3 | 1460 | GCAGCCGCTCTCCTTTCCGT | 73 | 121 |
| 148989 | 3 | 1479 | AGGTTCTGTGTTAGCCAGAG | 58 | 122 |
| 148990 | 3 | 1487 | AAACGTAAAGGTTCTGTGTT | 16 | 123 |
| 148991 | 3 | 1492 | CACAGAAACGTAAAGGTTCT | 22 | 124 |
| 148992 | 3 | 1499 | GTGGAGACACAGAAACGTAA | 51 | 125 |
| 148993 | 3 | 1552 | GGGACCTCATTAGCCACTGG | 55 | 126 |
| 148994 | 3 | 1587 | CGTCATCATTTTAAATAGAG | 10 | 127 |
| 148995 | 3 | 1605 | ATGGAGTCTAGAACCAAACG | 56 | 128 |
| 148996 | 3 | 1665 | TATAGGAGACACCCTGAATT | −3 | 129 |
| 148997 | 3 | 1671 | GAAGGGTATAGGAGACACCC | 57 | 130 |
| 148998 | 3 | 1684 | CCTAGGAGAAGAAGAAGGGT | 21 | 131 |
| 148999 | 3 | 1718 | CCACAGGCCATTAATACTCA | 45 | 132 |
| 149000 | 3 | 1726 | GGCAGAAACCACAGGCCATT | 56 | 133 |

TABLE 5-continued

Inhibition of mouse glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 149001 | 3 | 1732 | GGGTACGGCAGAAACCACAG | 42 | 134 |
| 149002 | 3 | 1769 | TATTGGCATCAATTTTGCCC | 22 | 135 |
| 149003 | 3 | 1779 | GGGACTGAGGTATTGGCATC | 9 | 136 |
| 149004 | 3 | 1794 | TCCTCTCCTCCCTTAGGGAC | 42 | 137 |
| 149005 | 3 | 1811 | TCATGAGAGTGGTGGACTCC | 27 | 138 |
| 149006 | 3 | 1818 | AGGGTATTCATGAGAGTGGT | 36 | 139 |
| 149007 | 3 | 1855 | AAGTCGGTTTGCCCTCTATA | 64 | 140 |
| 149008 | 3 | 1860 | TATACAAGTCGGTTTGCCCT | 65 | 141 |
| 149009 | 3 | 1873 | GCTTTATTCGATCTATACAA | 5 | 142 |

ISIS 148985 and ISIS 149008 were found to significantly decrease mouse glucose-6-phosphatase translocase mRNA levels, by approximately 84% and 65%, respectively. Both of these oligomeric compounds target sites in the 3'UTR of the mouse glucose-6-phosphatase translocase mRNA. Because they effectively inhibited mouse glucose-6-phosphatase translocase expression, they were further tested in normal, db/db, and ob/ob mice.

Example 6

Effect of Antisense Inhibitors of Glucose-6-Phosphatase Translocase on Lean Mice (ob/ob+/−Mice)

Ob/ob mice have a mutation in the leptin gene which results in obesity and hyperglycemia. As such, these mice are a useful model for the investigation of obesity and diabetes and treatments designed to treat these conditions. ob/ob+/− mice are heterozygous littermates of ob/ob mice, often referred to as lean littermates because they do not display the ob (obesity and hyperglycemia) phenotype. Seven-week old ob/ob+/−male mice were dosed twice weekly with 50 mg/kg of antisense oligonucleotide, given subcutaneously. A total of five doses were given. glucose-6-phosphatase translocase antisense oligonucleotides used were ISIS 148985 (SEQ ID NO: 118) and ISIS 149008 (SEQ ID NO: 141). Each treatment group was comprised of 4 animals. Animals were sacrificed 48 hours after the last dose of oligonucleotide was administered, and liver triglycerides, liver glycogen content, and target reduction in liver were measured.

Liver triglyceride levels are used to assess hepatic steatosis, or accumulation (poor clearing) of lipids in the liver. Tissue triglyceride levels were measured using a Triglyceride GPO assay from Roche Diagnostics (Indianapolis, Ind.). Liver triglycerides were about 19 mg/dL for saline treated lean mice and were about 14 mg/dL for ISIS 149008-treated lean mice.

Tissue glycogen was measured using the Glucose Trinder Reagent (Sigma-Aldrich, St. Louis, Mo.). Glycogen levels of lean mice treated with saline alone were approximately 37 mg/g of tissue. Mice treated with ISIS 149008 or 148985, the antisense inhibitors of glucose-6-phosphatase translocase, had glycogen levels of approximately 39 mg/g and 36 mg/g, respectively.

Thus, antisense inhibition of glucose-6-phosphatase translocase expression did not substantially alter liver glycogen or triglyceride levels in ob/ob+/−mice as compared to levels observed for mice treated with saline alone.

Glucose-6-phosphatase translocase mRNA levels in liver were measured at the end of study using RiboGreen™ RNA quantification reagent (Molecular Probes, Inc. Eugene, Oreg.) as taught in previous examples above.

Glucose-6-phosphatase translocase mRNA levels were reduced by approximately 51% in lean mice treated with ISIS 148985, and by approximately 88% in lean mice treated with ISIS 149008, when compared to saline treatment. Thus the antisense compounds ISIS 149008 and ISIS 148985 were effective in reducing liver glucose-6-phosphatase translocase mRNA levels in vivo.

Example 7

Effect of Antisense Inhibitors of Glucose-6-Phosphatase Translocase on ob/ob Mice Ob/ob mice have a mutation in the leptin gene which results in obesity and hyperglycemia. As such, these mice are a useful model for the investigation of obesity and diabetes and treatments designed to treat these conditions. In accordance with the present invention, compounds targeted to glucose-6-phosphatase translocase were tested in the ob/ob model of obesity and diabetes.

Seven-week old male C57B1/6J-Lep ob/ob mice (Jackson Laboratory, Bar Harbor, Me.) were fed a diet with a fat content of about 22% and were subcutaneously injected with oligonucleotides at a dose of 25 mg/kg two times per week. A total of eight doses were administered. Glucose-6-phosphatase translocase antisense oligonucleotides used were ISIS 148985 (SEQ ID NO: 118) and ISIS 149008 (SEQ ID NO: 141). ISIS 116847 (CTGCTAGCCTCTGGATTTGA; incorporated herein as SEQ ID NO: 143), targeted to mouse PTEN, was used as a positive control. Saline-injected animals served as negative controls. Animals were sacrificed 48 hours after the last dose of oligonucleotide was administered, and liver triglycerides, liver glycogen, and target reduction in liver were measured.

The effects of target inhibition on glucose metabolism were evaluated in the ob/ob mice treated as described above. Routine clinical analyzer instruments (Olympus Clinical Analyzer, Melville, N.Y.) were used to measure plasma glucose. Plasma glucose was measured prior to antisense oligonucleotide treatment (week 0) and during the second and fourth week of treatment. Fasted glucose measurements were made during week 3 after an overnight (about 14 hours) fast. Data are presented as the average from seven animals per treatment group.

In ob/ob mice treated with ISIS 148985 (SEQ ID NO: 118), an antisense inhibitor of glucose-6-phosphatase translocase, fed plasma glucose levels were approximately 348 mg/dL during week 0, 315 mg/dL during week 2 and 241 mg/dL during week 4. In mice treated with ISIS 149008 (SEQ ID NO: 141), another antisense inhibitor of glucose-6-phosphatase translocase, fed plasma glucose levels were approximately 344 mg/dL during week 0, 249 mg/dL during week 2 and 153 mg/dL during week 4. In contrast, mice treated with saline alone had fed plasma glucose levels of approximately 339 mg/dL during week 0, 401 mg/dL during week 2 and 372 mg/dL during week 4. Mice treated with a positive control oligonucleotide, ISIS 116847 (SEQ ID NO: 143), targeted to PTEN, had fed plasma glucose levels of approximately 339 mg/dL during week 0, 230 mg/dL during week 2 and 188 mg/dL during week 4. Thus fed plasma glucose levels were reduced after treatment with antisense inhibitors of glucose-6-phosphatase translocase.

During week 3 (at which time a total of 6 doses of treatment had been administered), plasma glucose levels were measured in fasted ob/ob mice. In the ob/ob mice treated with ISIS 148985 (SEQ ID NO: 118), an antisense inhibitor of glucose-6-phosphatase translocase, fasted plasma glucose levels were approximately 293 mg/dL. In mice treated with ISIS 149008 (SEQ ID NO: 141), fasted plasma glucose levels were approximately 237 mg/dL. Mice treated with positive control oligonucleotide ISIS 116847 (SEQ ID NO: 143), targeted to PTEN, had fasted plasma glucose levels of approximately 286 mg/dL. Mice treated with saline alone had fasted plasma glucose levels of approximately 297 mg/dL.

Glucose-6-phosphatase translocase mRNA levels in ob/ob mouse livers were measured at the end of the study using RIBOGREEN™ RNA quantification reagent (Molecular Probes, Inc. Eugene, Oreg.) as taught in previous examples above. Unless otherwise noted, results are presented as average inhibition from 4 animals per treatment, normalized to saline-injected control. glucose-6-phosphatase translocase mRNA levels were reduced by approximately 87% in mice treated with ISIS 149008, and by approximately 52% in mice treated with ISIS 148985, when compared to saline treatment. Glucose-6-phosphatase translocase mRNA levels were decreased by approximately 36% in mice treated with the positive control oligonucleotide, ISIS 116847 (n=3).

Hepatic steatosis, or buildup of lipids in the liver, was assessed by measuring the liver triglyceride content. Tissue triglycerides were measured with a Triglyceride GPO assay from Roche Diagnostics (Indianapolis, Ind.). Data are presented as averages from 5 animals per treatment group. Triglycerides were approximately 178 mg/g for saline treated mice, 162 mg/g for ISIS 149008-treated mice, 168 mg/g for ISIS 148985-treated mice, and 187 mg/g for ISIS 116847 (PTEN)-treated mice. Thus liver triglycerides were not increased in antisense-treated animals.

Hepatic steatosis is also assessed by routine histological analysis of frozen liver tissue sections stained with oil red 0 stain, which is commonly used to visualize lipid deposits, and counterstained with hematoxylin and eosin, to visualize nuclei and cytoplasm, respectively.

Tissue glycogen was measured using the Glucose Trinder Reagent (Sigma-Aldrich, St. Louis, Mo.). Glycogen levels of mice treated with saline alone were approximately 31 mg/g of tissue. Levels in mice treated with the positive control antisense compound ISIS 116847, targeted to PTEN, had levels of approximately 25 mg/g. Mice treated with ISIS 149008 or 148985, the antisense inhibitors of glucose-6-phosphatase translocase, had glycogen levels of approximately 31 mg/g and 30 mg/g, respectively. Thus, antisense inhibition of glucose-6-phosphatase translocase expression did not substantially alter tissue glycogen in ob/ob mice as compared to those treated with saline alone.

Example 8

Effects of Antisense Inhibition of Glucose-6-Phosphatase Translocase in the ob/ob Mouse Model of Obesity and Diabetes: Glucose Tolerance Test The mice described in Example 7 were evaluated for performance on glucose tolerance tests after the $6^{th}$ dose of saline or antisense oligonucleotides. Through measurement of glucose levels following the administration of a bolus of glucose, tolerance tests assess the physiological response to a glucose challenge.

Oral glucose tolerance tests (OGTT) were performed during the third week of treatment with saline, ISIS 116847 (targeted to PTEN, SEQ ID NO: 143), ISIS 148985 (SEQ ID NO: 118), or ISIS 149008 (SEQ ID NO: 141). To provide a baseline glucose level, fasted blood glucose levels were measured before the challenge. Glucose was administered by oral gavage via an 18 g gavage needle at a dose of 1 g/kg. Plasma glucose levels were measured for 30, 60, 90 and 120 minutes post-challenge using an Ascencia Glucometer Elite XL (Bayer, Tarrytown, N.Y.).

The results are presented in Table 6 as the average result (plasma glucose in mg/dL) from each treatment group (n=7). Saline-treated mice served as the control to which glucose levels were compared.

TABLE 6

Effects of antisense inhibition of glucose-6-phosphatase translocase on glucose tolerance test performance in ob/ob mice

| TREATMENT | TIME POST-GLUCOSE CHALLENGE (min.) | | | | |
| --- | --- | --- | --- | --- | --- |
| | 0 | 30 | 60 | 90 | 120 |
| Saline | 297 | 425 | 422 | 418 | 376 |
| ISIS 116847 | 286 | 290 | 238 | 229 | 194 |
| ISIS 149008 | 237 | 372 | 276 | 238 | 214 |
| ISIS 148985 | 293 | 489 | 433 | 331 | 305 |

A graph of the data presented in Table 6 reveals the appearance of peaks in plasma glucose levels over time. ISIS 149008, in particular, gave results indicating improved glucose tolerance, similar to that obtained with the positive control oligonucleotides, ISIS 116847.

Example 9

Effects of Antisense Inhibition of Glucose-6-Phosphatase Translocase in the ob/ob Mouse Model of Obesity and Diabetes: Glycerol Tolerance Test The mice described in Example 7 were evaluated for performance on glycerol tolerance tests after the $6^{th}$ dose of saline or antisense oligonucleotides. This is a functional measure of glucose-6-phosphatase translocase inhibition; i.e., whether the conversion of glycogen to glucose is impaired by antisense inhibitors of glucose-6-phosphatase translocase.

Glycerol tolerance tests were performed after treatment with saline, ISIS 148985 (SEQ ID NO: 118), or ISIS 149008 (SEQ ID NO: 141). Glycerol was administered by oral gavage via an 18 g gavage needle at a dose of 1 g/kg. Plasma glucose levels were measured for 30, 60, 90 and 120 minutes post-challenge using an Ascencia Glucometer Elite XL (Bayer, Tarrytown, N.Y.) and plotted over time. Area under the curve (AUC) for each treatment graph was calculated. ISIS 148985 did not show significant decrease in AUC compared to saline in this experiment (perhaps due to less robust target inhibition than seen with 149008); however, ISIS 149008 showed a significant decrease in AUC (approximately 30% decrease) compared to saline control. This indicates that glucose-6-phosphatase translocase functional activity (conversion of glycerol to glucose) was effectively blocked by this antisense inhibitor of glucose-6-phosphatase translocase.

Example 10

Effect of Antisense Inhibitors of Glucose-6-Phosphatase Translocase in Leptin Receptor-Deficient Mice (db/db Mice)

Leptin is a hormone produced by fat that regulates appetite. Deficiencies in this hormone in both humans and non-human animals leads to obesity. db/db mice have a mutation in the leptin receptor gene which results in obesity and hyperglycemia. As such, these mice are a useful model for the investigation of obesity and diabetes and treatments designed to treat these conditions. db/db mice, which have lower circulating levels of insulin and are more hyperglycemic than the ob/ob mice which harbor a mutation in the leptin gene, are often used as a rodent model of type 2 diabetes. In accordance with the present invention, oligomeric compounds of the present invention were tested in the db/db model of obesity and diabetes.

Seven-week old male C57B1/6J-Lepr db/db mice (Jackson Laboratory, Bar Harbor, Me.) were fed a diet with a fat content of about 14% and were subcutaneously injected with one or more of the oligomeric compounds of the invention or a control compound at a dose of 25 mg/kg two times per week. Glucose-6-phosphatase translocase antisense oligonucleotides used were ISIS 148985 (SEQ ID NO: 118) and ISIS 149008 (SEQ ID NO: 141). ISIS 116847 (SEQ ID NO: 143), targeted to mouse PTEN, was used as a positive control. The scrambled control oligonucleotide ISIS 141923 (CCTTCCCTGAAGGTTCCTCC, incorporated herein as SEQ ID NO: 144) served as a negative control along with saline-injected animals. ISIS 141923 and ISIS 116847 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines.

48 hours after the final treatment, mice were sacrificed and target levels were evaluated in liver. RNA isolation and target mRNA expression level quantitation were performed as described by other examples herein.

The effects of target inhibition on glucose metabolism were evaluated in the db/db mice treated with the oligomeric compounds of the invention. For seven animals per treatment group, plasma glucose (fed) was measured prior to the start of the treatment (week 0) and during weeks 2 and 4 of treatment. Fasted glucose measurements were made during week three, after animals were fasted overnight (about 15 hours). Data are expressed as the averages per treatment group.

Mice treated with ISIS 148985 (SEQ ID NO: 118), an antisense inhibitor of glucose-6-phosphatase translocase, had fed plasma glucose levels of approximately 267 mg/dL during week 0, 512 mg/dL during week 2, and 552 mg/dL during week 4. Mice treated with ISIS 149008 (SEQ ID NO: 141), another antisense inhibitor of glucose-6-phosphatase translocase, had fed plasma glucose levels of approximately 272 mg/dL during week 0, 390 mg/dL during week 2, and 347 mg/dL during week 4. Mice treated with saline alone had fed plasma glucose levels of approximately 270 mg/dL during week 0, 534 mg/dL during week 2, and 627 mg/dL during week 4. db/db mice treated with a positive control oligonucleotide, ISIS 116847 (SEQ ID NO: 143), targeted to PTEN, had fed plasma glucose levels of approximately 267 mg/dL during week 0, 360 mg/dL during week 2, and 334 mg/dL during week 4. Mice treated with negative control oligonucleotide ISIS 141923 (SEQ ID NO: 144) had fed plasma glucose levels of approximately 272 mg/dL during week 0, 538 mg/dL during week 2, and 563 mg/dL during week 4. Thus the increase in fed plasma glucose levels over time observed in saline treated animals, or in animals treated with the negative control ISIS 141923, was diminished with treatment with ISIS 149008, an antisense inhibitor of glucose-6-phosphatase translocase.

During week 3 of treatment, plasma glucose levels were measured in the db/db mice described above after an overnight (about 15 hours) fast. In mice treated with ISIS 148985 (SEQ ID NO: 118), an antisense inhibitor of glucose-6-phosphatase translocase, fasted plasma glucose levels were approximately 288 mg/dL. In the mice treated with ISIS 149008 (SEQ ID NO: 141), another antisense inhibitor of glucose-6-phosphatase translocase, fasted plasma glucose levels were approximately 241 mg/dL. Mice treated with saline alone had fasted plasma glucose levels of approximately 343 mg/dL. db/db mice treated with a positive control oligonucleotide, ISIS 116847 (SEQ ID NO: 143), targeted to PTEN, had fasted plasma glucose levels of approximately 241 mg/dL. Mice treated with negative control oligonucleotide ISIS 141923 had fasted plasma glucose levels of approximately 287 mg/dL.

Glucose-6-phosphatase translocase mRNA levels in db/db mouse livers were measured at the end of study using RIBOGREEN™ RNA quantification reagent (Molecular Probes, Inc. Eugene, Oreg.) as taught in previous examples above. Unless otherwise noted, data are expressed as the average percent inhibition from 5 animals per treatment group. Glucose-6-phosphatase translocase mRNA levels were reduced by approximately 82% in mice treated with ISIS 149008, and by approximately 19% in mice treated with ISIS 148985, when compared to saline treatment. glucose-6-phosphatase translocase mRNA levels were not substantially decreased in mice treated with the control oligonucleotide, ISIS 116847 (about 8% inhibition, n=4) or in mice treated with the negative control oligonucleotide, ISIS 141923 (about 4% inhibition, n=3).

Patients with the human glycogen storage disease type 1b have mutations in the glucose-6-phosphatase translocase gene. Because one manifestation of these mutations is a defect in hepatic glycogen deposition leading to glycogen accumulation in the liver, the db/db mice were further evaluated at the end of the treatment period for liver glycogen stores. Tissue glycogen was measured using the Glucose Trinder Reagent (Sigma-Aldrich, St. Louis, Mo.). Results are presented as the average level from 5 animals per treatment. Glycogen levels of mice treated with saline alone were approximately 46 mg/g of tissue. Levels in mice treated with the positive control antisense compound ISIS 116847 had decreased levels of approximately 30 mg/g. Mice treated with the scrambled control compound ISIS 141923 had levels more similar to saline control of approximately 39 mg/g. Mice treated with ISIS 149008 or 148985, the antisense inhibitors of glucose-6-phosphatase translocase, had glycogen levels of approximately 38 mg/g and 37 mg/g, respectively. Thus inhibition of glucose-6-phosphatase translocase did not result in increased liver glycogen content.

Example 11

Effect of Antisense Inhibitors of Glucose-6-Phosphatase Translocase in Leptin Receptor-Deficient Mice (db/db Mice)-Dose-Response Study Because patients with human glycogen storage disease type 1b have mutations in the glucose-6-phosphatase translocase gene which result in hypoglycemia, lactic acidosis, hepatic glycogen deposition, renal enlargement, hyperuricemia, and neutropenia, the db/db mice treated with antisense inhibitors of glucose-6-phosphatase translocase were tested for these manifestations of loss of glucose-6-phosphatase translocase activity.

Seven-week old male C57B1/6J-Lepr db/db mice (Jackson Laboratory, Bar Harbor, Me.) were fed a diet with a fat content of about 14% (Formulab Diet 5008) and were subcutaneously injected with ISIS 116847 (SEQ ID NO: 143), ISIS 141923 (SEQ ID NO: 144), or ISIS 148985 (SEQ ID NO: 118), an antisense inhibitor of glucose-6-phosphatase translocase, at a dose of 25 mg/kg two times per week for 4 weeks. Other treatment groups were subcutaneously injected with ISIS 149008 (SEQ ID NO: 141), an antisense inhibitor of glucose-6-phosphatase translocase, at doses of 25 mg/kg, 12.5 mg/kg, or 6.25 mg/kg, twice weekly for four weeks. Saline-injected animals served as controls. 48 hours after the eighth and final dose was administered, mice were sacrificed and target levels were evaluated in liver. RNA isolation and target mRNA expression level quantitation were performed as described by other examples herein.

For seven animals per treatment group, plasma glucose was measured with routine clinical analyzer instruments (e.g. Olympus Clinical Analyzer). Data are expressed as averages per treatment group. In db/db mice treated with 25 mg/kg ISIS 148985 (SEQ ID NO: 118), an antisense inhibitor of glucose-6-phosphatase translocase, fed plasma glucose levels were approximately 289 mg/dL during week 0, 394 mg/dL during week 2, and 443 mg/dL during week 4.

In mice treated with 25 mg/kg ISIS 149008 (SEQ ID NO: 141), another antisense inhibitor of glucose-6-phosphatase translocase, fed plasma glucose levels were approximately 286 mg/dL during week 0, 359 mg/dL during week 2, and 299 mg/dL during week 4. In mice treated with 12.5 mg/kg ISIS 149008 fed plasma glucose levels were approximately 283 mg/dL during week 0, 411 mg/dL during week 2, and 203 mg/dL during week 4. Mice treated with 6.25 mg/kg ISIS 149008 showed fed plasma glucose levels of approximately 289 mg/dL during week 0, 397 mg/dL during week 2, and 478 mg/dL during week 4.

Mice treated with saline alone had fed plasma glucose levels of approximately 280 mg/dL during week 0, 517 mg/dL during week 2, 510 mg/dL during week 4. db/db mice treated with a positive control oligonucleotide, ISIS 116847 (SEQ ID NO: 143), targeted to PTEN, had fed plasma glucose levels of approximately 282 mg/dL during week 0, 291 mg/dL during week 2, 224 mg/dL during week 4. Mice treated with negative control oligonucleotide ISIS 141923 (SEQ ID NO: 144 had fed plasma glucose levels of approximately 287 mg/dL during week 0, 456 mg/dL during week 2, 510 mg/dL during week 4. Thus antisense inhibition of glucose-6-phosphatase translocase attenuated the rise in plasma glucose levels observed in db/db mice treated with saline only or the negative control ISIS 141923 over the 4-week time course.

Glucose-6-phosphatase translocase mRNA levels in db/db mouse livers were measured at the end of study using RIBOGREEN™ RNA quantification reagent (Molecular Probes, Inc. Eugene, Oreg.) as taught in previous examples above. Data are expressed as the average of 5 animals per treatment group. Glucose-6-phosphatase translocase mRNA levels were reduced by approximately 45% in mice treated with 6.25 mg/kg ISIS 149008, by approximately 69% in mice treated with 12.5 mg/kg ISIS 149008, and by approximately 81% in mice treated with 25 mg/kg ISIS 149008, when compared to saline treatment. Target mRNA levels were reduced by approximately 21% by ISIS 148985. Glucose-6-phosphatase translocase mRNA levels were decreased approximately 27% in mice treated with the positive control oligonucleotide, ISIS 116847, and were unaffected in mice treated with the negative control oligonucleotide, ISIS 141923 (approximately 1% inhibition). Therefore, antisense inhibitors of glucose-6-phosphatase translocase reduced target mRNA levels in the liver of db/db mice, and ISIS 149008 did so in a dose-dependent manner.

To further assess the physiological effects resulting from inhibition of target mRNA, the db/db mice were evaluated at the end of the treatment period for plasma triglycerides, plasma cholesterol, free fatty acids (FFA), lactate and plasma transaminase levels. The transaminases ALT and AST are indicators of liver function. Plasma triglycerides, cholesterol, free fatty acids, and transaminases were measured by routine clinical analyzer instruments (e.g. Olympus Clinical Analyzer, Melville, N.Y.). Results are presented in table 7 as the averages from seven animals per treatment group.

TABLE 7

Effects of antisense inhibition of glucose-6-phosphatase translocase on plasma triglycerides, cholesterol, free fatty acids, transaminases and lactate in db/db mice

| Treatment | Plasma Triglycerides (mg/dL) | Cholesterol (mg/dL) | Free Fatty Acids (mEq/L) | ALT (IU/L) | AST (IU/L) | Lactate (mg/dL) |
|---|---|---|---|---|---|---|
| Saline | 213 | 152 | 0.8 | 56 | 59 | 108 |
| ISIS 116847 | 166 | 161 | 0.8 | 70 | 62 | 131 |

TABLE 7-continued

Effects of antisense inhibition of glucose-6-phosphatase translocase on plasma triglycerides, cholesterol, free fatty acids, transaminases and lactate in db/db mice

| Treatment | Plasma Triglycerides (mg/dL) | Cholesterol (mg/dL) | Free Fatty Acids (mEq/L) | ALT (IU/L) | AST (IU/L) | Lactate (mg/dL) |
|---|---|---|---|---|---|---|
| ISIS 141923 | 166 | 167 | 0.9 | 72 | 56 | 128 |
| ISIS 149008, 25 mg/mL | 197 | 167 | 0.9 | 68 | 55 | 129 |
| ISIS 149008, 12.5 mg/mL | 247 | 172 | 1.0 | 64 | 56 | 127 |
| ISIS 149008, 6 mg/mL | 205 | 158 | 0.9 | 59 | 49 | 125 |
| ISIS 148985 | 202 | 164 | 1.1 | 73 | 48 | 105 |

Patients with the human glycogen storage disease type 1b have mutations in the glucose-6-phosphatase translocase gene. Because one manifestation of these mutations is a defect in hepatic glycogen deposition, the db/db mice were further evaluated at the end of the treatment period for liver glycogen stores. Tissue glycogen levels were measured using the Glucose Trinder Reagent (Sigma-Aldrich, St. Louis, Mo.). Tissue triglyceride levels were measured using a Triglyceride GPO Assay from Roche Diagnostics (Indianapolis, Ind.). Liver triglyceride levels were used to assess hepatic steatosis, or accumulation of lipids in the liver. Hepatic steatosis was also assessed by routine histological analysis of frozen liver tissue sections stained with oil red 0 stain, which is commonly used to visualize lipid deposits, and counterstained with hematoxylin and eosin, to visualize nuclei and cytoplasm, respectively. Data are presented in Table 8 as the averages from 5 animals per treatment group.

TABLE 8

Effects of antisense inhibition of glucose-6-phosphatase translocase on liver triglycerides and glycogen stores in db/db mice

| Treatment | Triglycerides mg/g | Glycogen mg/g |
|---|---|---|
| Saline | 25 | 47 |
| ISIS 116847 | 67 | 39 |
| ISIS 141923 | 30 | 43 |
| ISIS 149008, 25 mg/mL | 58 | 45 |
| ISIS 149008, 12.5 mg/mL | 41 | 45 |
| ISIS 149008, 6 mg/mL | 33 | 48 |
| ISIS 148985 | 24 | 47 |

As shown in table 8, ISIS 148985 did not significantly increase liver triglycerides above levels seen for saline-treated or ISIS 141923 (scrambled control) treated animals. Liver glycogen stores were unaffected by treatment with antisense inhibitors of glucose-6-phosphatase translocase as compared to the levels observed for saline-treated animals.

Because mutations in the glucose-6-phosphatase translocase gene responsible for human glycogen storage disease type 1b result in neutropenia, plasma neutrophils and lymphocytes were measured for animals in each treatment group. Data are expressed in Table 9 as the averages from the number (n) of animals indicated in the table.

TABLE 9

Effects of antisense inhibition of glucose-6-phosphatase translocase on plasma neutrophils and lymphocytes in db/db mice

| Treatment | Neutrophils Plasma cells/nL | Lymphocytes Plasma cells/nL | n |
|---|---|---|---|
| Saline | 0.9 | 2.7 | 5 |
| ISIS 116847 | 0.8 | 3.1 | 5 |
| ISIS 141923 | 0.9 | 2.6 | 4 |
| ISIS 149008, 25 mg/mL | 1.0 | 3.7 | 5 |
| ISIS 149008, 12.5 mg/mL | 0.9 | 3.2 | 6 |
| ISIS 149008, 6 mg/mL | 1.1 | 2.8 | 6 |
| ISIS 148985 | 1.0 | 3.3 | 6 |

Treatment with the compounds of the invention did not affect plasma neutrophil levels, demonstrating that reduction of glucose-6-phosphatase translocase mRNA with antisense inhibitors did not cause neutropenia as is observed in human glycogen storage disease type 1b.

Furthermore, treatment with the compounds of the invention did not cause an increase in kidney weight, demonstrating that antisense inhibition of glucose-6-phosphatase translocase expression in db/db mice did not cause kidney enlargement as is observed in human glycogen storage disease type 1b.

Example 12

Effects of Antisense Inhibition of Glucose-6-Phosphatase Translocase in the db/db Mouse Model of Obesity and Diabetes: Glucose Tolerance Test The mice described in Example 11 were evaluated for performance on glucose tolerance tests after the $6^{th}$ dose of saline or antisense oligonucleotides. Through measurement of glucose levels following the administration of a bolus of glucose, tolerance tests assess the physiological response to a glucose challenge.

Oral glucose tolerance tests (OGTT) were performed during week 3 of treatment with saline, ISIS 116847 (targeted to PTEN, SEQ ID NO: 143), ISIS 149008 (SEQ ID NO: 141), ISIS 148985 (SEQ ID NO: 118), or ISIS 141923 (SEQ ID NO: 144). To provide a baseline glucose level, fasted blood glucose levels were measured before the challenge. Glucose was administered by oral gavage via an 18 g gavage needle at a dose of 1 g/kg. Plasma glucose levels were measured for 30, 60, 90 and 120 minutes post-challenge using an Ascencia Glucometer Elite XL (Bayer, Tarrytown, N.Y.).

The results are presented in Table 10 as the average plasma glucose level (in mg/dL) per time point from each treatment group (n=7).

TABLE 10

Effects of antisense inhibition of glucose-6-phosphatase translocase on glucose tolerance test performance in db/db mice

| TREATMENT | TIME POST-GLUCOSE CHALLENGE (min.) | | | | |
|---|---|---|---|---|---|
| | 0 | 30 | 60 | 90 | 120 |
| Saline | 176 | 467 | 437 | 315 | 349 |
| ISIS 116847 | 181 | 441 | 367 | 305 | 286 |
| ISIS 141923 | 284 | 522 | 445 | 338 | 339 |
| ISIS 149008, 25 mg/kg | 227 | 462 | 326 | 272 | 231 |
| ISIS 149008, 12.5 mg/kg | 152 | 529 | 427 | 348 | 329 |
| ISIS 149008, 6 mg/kg | 204 | 518 | 468 | 377 | 330 |
| ISIS 148985 | 230 | 494 | 445 | 335 | 355 |

A graph of the data presented in Table 10 reveals the appearance of peaks in plasma glucose levels over time for animals treated with ISIS 148985 or varied doses of ISIS 149008, antisense inhibitors of glucose-6-phosphatase translocase. A dose-dependent improvement in glucose tolerance is seen for ISIS 149008. This is confirmed by calculating the area under the curve (AUC) for the graphed glucose values; ISIS 149008 at 25 mg/kg significantly reduced the AUC compared to saline.

The results presented in Examples 5 to 12 suggest that inhibition of glucose-6-phosphatase translocase with antisense oligonucleotides cause marked and beneficial glucose lowering effects in well accepted animal models of diabetes without producing many of the deleterious side effects observed after global knockout of the gene. Thus, inhibition of glucose-6-phosphatase translocase using antisense oligonucleotides is believed to be a viable and advantageous therapeutic approach for the treatment of type 2 diabetes.

Example 13

Antisense Inhibition of Human Glucose-6-Phosphatase Translocase Expression by Oligomeric Compounds A series of oligomeric compounds was designed to target different regions of human glucose-6-phosphatase translocase, using published sequences cited in Table 1. The compounds are shown in Table 11. All compounds in Table 4 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using a primer-probe set designed to hybridize to human glucose-6-phosphatase translocase.

Data are from experiments in which HepG2 cells were treated with antisense oligonucleotides of the present invention using LIPOFECTIN™. A reduction in expression is expressed as percent inhibition in Table 11. If present, "N.D." indicates "not determined". The target regions to which these oligomeric compounds are inhibitory are herein referred to as "validated target segments."

TABLE 11

Inhibition of human glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 145652 | 1 | 161 | TGGGCTGCCATGGTAGAAAA | 50 | 145 |
| 145657 | 1 | 257 | GGCATGACAAAGGAGAAGGT | 43 | 146 |
| 145662 | 1 | 566 | GCCCACCAAGTGCCAAACTG | 52 | 147 |
| 145664 | 1 | 591 | CAGGTTCATGCTGGTTGACA | 66 | 148 |
| 145667 | 1 | 647 | CGCCAGCTGTAGCTCTGGGC | 54 | 149 |
| 145668 | 1 | 650 | CTGCGCCAGCTGTAGCTCTG | 47 | 150 |
| 145670 | 1 | 683 | ACCACACACAGTGCCCCAGA | 42 | 151 |
| 145671 | 1 | 690 | GGAGACAACCACACACAGTG | 39 | 152 |
| 145673 | 1 | 722 | GGTTCATTGTGGATGAGCAG | 47 | 153 |
| 145685 | 1 | 902 | AGGAAGAACTGGCCCCAGTC | 71 | 154 |
| 145686 | 1 | 907 | GGATAAGGAAGAACTGGCCC | 32 | 155 |
| 145700 | 1 | 1316 | TTGGCAATGGTGCTGAAGGG | 24 | 156 |
| 145702 | 1 | 1346 | ACCCAGAAGGCTGTGCTCCA | 74 | 157 |
| 145706 | 1 | 1418 | CGGCCCATCTTGGTGCGGAT | 96 | 158 |
| 194838 | 1 | 1710 | TGACTGCAGAAGTTTCCTGT | 42 | 40 |
| 194839 | 1 | 1946 | CCACCTATATCCAACTGCGC | 75 | 41 |

TABLE 11-continued

Inhibition of human glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 194850 | 1 | 354 | CCCACTGACAAACTTGCTGA | 38 | 52 |
| 194855 | 1 | 800 | AGGGTGCTCTCCTCCTTCAA | 66 | 57 |
| 359506 | 1 | 409 | CCAGGAGCAGCCCAGAAGAG | 58 | 159 |
| 359507 | 1 | 413 | CCAACCAGGAGCAGCCCAGA | 49 | 160 |
| 359508 | 1 | 417 | CAGGCCAACCAGGAGCAGCC | 68 | 161 |
| 359509 | 1 | 562 | ACCAAGTGCCAAACTGAGAT | 24 | 162 |
| 359510 | 1 | 569 | ATGGCCCACCAAGTGCCAAA | 38 | 163 |
| 359511 | 1 | 581 | CTGGTTGACAGGATGGCCCA | 55 | 164 |
| 359512 | 1 | 585 | CATGCTGGTTGACAGGATGG | 43 | 165 |
| 359513 | 1 | 594 | AGCCAGGTTCATGCTGGTTG | 62 | 166 |
| 359514 | 1 | 597 | TCCAGCCAGGTTCATGCTGG | 37 | 167 |
| 359515 | 1 | 600 | CCCTCCAGCCAGGTTCATGC | 62 | 168 |
| 359516 | 1 | 604 | CCAGCCCTCCAGCCAGGTTC | 69 | 169 |
| 359517 | 1 | 653 | GTGCTGCGCCAGCTGTAGCT | 25 | 170 |
| 359518 | 1 | 658 | CCAGCGTGCTGCGCCAGCTG | 47 | 171 |
| 359519 | 1 | 686 | ACAACCACACAGTGCCCC | 53 | 172 |
| 359520 | 1 | 693 | GAAGGAGACAACCACACACA | 42 | 173 |
| 359521 | 1 | 697 | AGAGGAAGGAGACAACCACA | 32 | 174 |
| 359522 | 1 | 726 | AGCAGGTTCATTGTGGATGA | 91 | 175 |
| 359523 | 1 | 731 | ACATCAGCAGGTTCATTGTG | 43 | 176 |
| 359524 | 1 | 783 | CAAGGAGCCCTTCTTGCCCT | 56 | 177 |
| 359525 | 1 | 788 | TCCTTCAAGGAGCCCTTCTT | 56 | 178 |
| 359526 | 1 | 793 | TCTCCTCCTTCAAGGAGCCC | 54 | 179 |
| 359527 | 1 | 797 | GTGCTCTCCTCCTTCAAGGA | 45 | 180 |
| 359528 | 1 | 897 | GAACTGGCCCCAGTCAGTAC | 45 | 181 |
| 359529 | 1 | 913 | TCTCCTGGATAAGGAAGAAC | 15 | 182 |
| 359530 | 1 | 918 | TCCTTTCTCCTGGATAAGGA | 59 | 183 |
| 359531 | 1 | 1111 | TTACCCGGAAGAGGTACATG | 62 | 184 |
| 359532 | 1 | 1117 | TCACTGTTACCCGGAAGAGG | 48 | 185 |
| 359533 | 1 | 1121 | CTGGTCACTGTTACCCGGAA | 69 | 186 |
| 359534 | 1 | 1125 | GTCACTGGTCACTGTTACCC | 75 | 187 |
| 359535 | 1 | 1149 | TACCAGGATCCAGAGCTTGG | 58 | 188 |
| 359536 | 1 | 1155 | TCCCAATACCAGGATCCAGA | 55 | 189 |
| 359537 | 1 | 1160 | ACAGCTCCCAATACCAGGAT | 93 | 190 |
| 359538 | 1 | 1165 | CAAATACAGCTCCCAATACC | 29 | 191 |
| 359539 | 1 | 1170 | GAACCAAATACAGCTCCCA | 38 | 192 |

TABLE 11-continued

Inhibition of human glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 359540 | 1 | 1172 | GAGAAACCAAATACAGCTCC | 92 | 193 |
| 359541 | 1 | 1176 | CGAGGAGAAACCAAATACAG | 41 | 194 |
| 359542 | 1 | 1181 | CCATACGAGGAGAAACCAAA | 46 | 195 |
| 359543 | 1 | 1320 | GTGCTTGGCAATGGTGCTGA | 74 | 196 |
| 359544 | 1 | 1324 | TGTAGTGCTTGGCAATGGTG | 7 | 197 |
| 359545 | 1 | 1349 | GCCACCCAGAAGGCTGTGCT | 65 | 198 |
| 359546 | 1 | 1353 | TTCAGCCACCCAGAAGGCTG | 39 | 199 |
| 359547 | 1 | 1414 | CCATCTTGGTGCGGATGTTT | 91 | 200 |
| 359548 | 1 | 1421 | ACTCGGCCCATCTTGGTGCG | 96 | 201 |

Certain oligomeric compounds presented in Table 11 are cross-species oligos that are complementary to rat glucose 6-phosphatase translocase. Other oligomeric compounds in Table 11 contain mismatches to the rat glucose 6-phosphatase translocase sequence. ISIS 359508 and ISIS 359453 are oligos designed to target human glucose-6-phosphatase translocase and which contain one or two mismatches to the rat target, respectively. For further studies in rat models, the sequences of these human oligonucleotides were adjusted to have 100% complementary to published sequences for rat glucose 6-phosphatase translocase (GENBANK™ accession no: AF080468.1, incorporated herein as SEQ ID NO: 4). The rat oligomeric compounds are ISIS 349113 (CAGACCAAC-CAGGAGCAGCC, incorporated herein as SEQ ID NO: 202) and ISIS 366228 (GTGCTTGGCGATGGTACTGA, incorporated herein as SEQ ID NO: 203). ISIS 349113 and ISIS 366228 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines.

Example 14

Antisense Inhibition of Glucose-6-Phosphatase Translocase in Normal Rats: Dose-Response Study In accord with the present invention, oligomeric compounds were selected for further investigation in vivo. For three weeks, male Sprague-Dawley rats were injected twice-weekly with doses of 12.5 mg/kg, 25 mg/kg, or 50 mg/kg of ISIS 145760, ISIS 359543, or ISIS 366228. Each treatment group was comprised of 4 animals. Animals which received twice weekly injections of saline served as controls.

At the end of the treatment period, animals were sacrificed and target reduction in liver was measured by real-time PCR as described in other examples herein. Results are shown in Table 12 as the average percent reduction in glucose-6-phosphatase translocase levels as compared to saline treated control.

TABLE 12

Target reduction in liver: rat dose-response study

| Treatment | SEQ ID NO | % Inhibition Dose (mg/kg) | | |
|---|---|---|---|---|
| | | 12.5 | 25 | 50 |
| ISIS 145706 | 158 | 12 | 56 | 77 |
| ISIS 359543 | 196 | 50 | 62 | 77 |
| ISIS 366228 | 203 | 69 | 82 | 90 |

As shown in Table 12, ISIS 145706, ISIS 359543, and ISIS 366228 were effective in reducing target mRNA levels in rat liver in a dose-dependent manner.

Body weight was monitored throughout the study period. Increases in body weights for animals treated with doses of ISIS 145706, ISIS 359543, or ISIS 366228 were comparable to the increases in body weight observed for saline-treated control animals. Tissue weights were also measured at the end of the study. Average body weights measured in week 3 and tissue weights measured at the end of the study are presented in Table 13 (in grams) for each treatment group.

TABLE 13

Body weight and tissue weights of rats treated with antisense oligonucleotides targeting glucose-6-phosphatase translocase

| Treatment Group | Body weight | Liver | Fat | Spleen | Kidney |
|---|---|---|---|---|---|
| Saline | 290 | 15 | 1.8 | 0.7 | 3 |
| ISIS 145706, 12.5 mg/kg | 289 | 15 | 1.5 | 0.7 | 3 |
| ISIS 145706, 25 mg/kg | 300 | 15 | 1.3 | 1.0 | 3 |
| ISIS 145706, 50 mg/kg | 290 | 16 | 1.2 | 0.9 | 3 |
| ISIS 359543, 12.5 mg/kg | 285 | 15 | 1.4 | 0.9 | 3 |
| ISIS 359543, 25 mg/kg | 295 | 16 | 1.3 | 1.1 | 3 |
| ISIS 359543, 50 mg/kg | 277 | 13 | 1.0 | 1.4 | 3 |
| ISIS 366228, 12.5 mg/kg | 296 | 15 | 1.6 | 1.1 | 3 |
| ISIS 366228, 25 mg/kg | 279 | 15 | 1.5 | 1.1 | 3 |
| ISIS 366228, 50 mg/kg | 271 | 15 | 1.1 | 1.1 | 3 |

As shown in Table 13, renal or hepatic enlargement are not associated with antisense oligonucleotide treatment.

To further assess the physiological effects resulting from inhibition of target mRNA, the rats were evaluated at the beginning (Wk 0) and at the end (Wk 3) of the treatment period for plasma glucose, plasma cholesterol, and plasma triglyceride levels. Triglycerides and cholesterol were measured by routine clinical analyzer instruments (e.g. Olympus Clinical Analyzer, Melville, N.Y.). Glucose levels were measured using a glucose analyzer, for example a YSI glucose analyzer (YSI Scientific, Yellow Springs, Ohio). Results are presented in Table 14 as the average level of plasma glucose, plasma cholesterol (CHOL), or plasma triglycerides (TRIG) measured per treatment group.

TABLE 14

Effects of antisense inhibition of glucose-6-phosphatase translocase on plasma glucose, triglycerides, and cholesterol levels

| Treatment | GLUCOSE | | CHOL | | TRIG | |
|---|---|---|---|---|---|---|
| | WK 0 | WK 3 | WK 0 | WK 3 | WK 0 | WK 3 |
| Saline | 135 | 139 | 74 | 58 | 69 | 140 |
| ISIS 145706, 12.5 mg/kg | 149 | 151 | 69 | 51 | 54 | 61 |
| ISIS 145706, 25 mg/kg | 149 | 148 | 80 | 59 | 45 | 58 |
| ISIS 145706, 50 mg/kg | 148 | 151 | 79 | 57 | 66 | 52 |
| ISIS 359543, 12.5 mg/kg | 138 | 165 | 80 | 57 | 69 | 61 |
| ISIS 359543, 25 mg/kg | 138 | 154 | 82 | 57 | 62 | 37 |
| ISIS 359543, 50 mg/kg | 135 | 136 | 87 | 54 | 69 | 19 |
| ISIS 366228, 12.5 mg/kg | 147 | 146 | 70 | 49 | 54 | 84 |
| ISIS 366228, 25 mg/kg | 148 | 149 | 93 | 70 | 56 | 76 |
| ISIS 366228, 50 mg/kg | 137 | 139 | 76 | 54 | 65 | 64 |

Hypoglycemia was not observed for any of the treatment groups. As shown in Table 14, animals treated with ISIS 359543 showed dose-dependent reductions in plasma triglycerides. Treatment with ISIS 145706 or ISIS 366228 prevented the increases in triglycerides observed in saline-treated animals. Therefore, one embodiment of the present invention is a method of reducing triglycerides in an animal by administering an oligomeric compound of the invention.

Example 15

Antisense Inhibition of Glucose-6-Phosphatase Translocase in ZDF Aged Rats in Combination with Rosiglitazone The Zucker fatty (fa/fa) rat is an example of a genetic obesity with an autosomal recessive pattern of inheritance. The obesity in fa/fa animals is correlated with excessive eating, decreased energy expenditure, compromised thermoregulatory heat production, hyperinsulinemia (overproduction of insulin), and hypercorticosteronemia (overproduction of corticosteroids). The fa mutation has been identified as an amino acid substitution in the extracellular domain of the receptor for leptin. As a consequence, the fa/fa animal has elevated plasma leptin levels and is resistant to exogenous leptin administration.

In a further embodiment, the effects of antisense inhibition of glucose-6-phosphatase translocase are evaluated in the aged Zucker fa/fa rat model of obesity against the standard care therapeutic rosiglitazone and in combination with rosiglitazone. Aged Zucker fa/fa rats are resistant to standard glucose-lowering therapeutics (for example metformin or rosiglitazone), thus the combination of rosiglitazone with an antisense oligonucleotide targeting glucose-6-phosphatase translocase was investigated for additive therapeutic effects. Male Zucker fa/fa rats, about 17 to 18 weeks of age, purchased from Charles River Laboratories (Wilmington, Mass.), are maintained on a normal rodent diet. Animals are placed into treatment groups of 8 animals each. One treatment group was dosed subcutaneously twice weekly with 12.5 mg/kg of ISIS 366228 (SEQ ID NO: 203). Another treatment group was dosed twice weekly with 25 mg/kg of ISIS 366228. Other treatment groups were dosed with 12.5 mg/kg or 25 mg/kg ISIS 366228 twice weekly in combination with daily 3 mg/kg doses of rosiglitazone (Rosi) administered in powdered food. Another treatment group received the food-administered daily doses of 3 mg/kg of rosiglitazone alone. Saline-injected animals served as a control treatment group.

At the end of the treatment period, animals were sacrificed and target reduction in liver and kidney were measured by real-time PCR as described in other examples herein. Also measured were reductions in the catalytic subunit of glucose-6-phosphatase (G6PC) using a primer-probe set designed to hybridize to that mRNA. For example, the following primer-probe set was designed to hybridize to rat glucose-6-phosphatase translocase sequences cited in Table 1:
Forward primer: GCTGGAAGCCTGGGACCT (incorporated herein as SEQ ID NO: 339)
Reverse primer: GGTGCTGCGCCAGCTG (incorporated herein as SEQ ID NO: 340)
PCR probe: FAM-TCTTGGCGACAATCCTTGCTCA-GAGC-TAMRA (incorporated herein as SEQ ID NO: 341), where FAM is the fluorescent dye and TAMRA is the quencher dye.

Results for each treatment group are shown in Table 15 as the average percent reduction in glucose-6-phosphatase translocase levels or in G6PC as compared to saline treated control.

TABLE 15

Reduction of glucose-6-phosphatase translocase or glucose-6-phosphatase translocase expression in liver or kidney of ZDF rats

| Treatment group | % Inhibition of glucose-6-phosphatase translocase | | % Inhibition of G6PC | |
|---|---|---|---|---|
| | Liver | Kidney | Liver | Kidney |
| ISIS 366228, 12.5 mg/kg | 40 | 35 | 39 | 17 |
| ISIS 366228, 25 mg/kg | 80 | 46 | 0 | 33 |
| Rosi + ISIS 366228, 12.5 mg/kg | 46 | 37 | 12 | 2 |
| Rosi + ISIS 366228, 25 mg/kg | 89 | 49 | 26 | 21 |
| Rosiglitazone | 46 | 0 | 63 | 5 |

As shown in Table 15, ISIS 366228 reduced glucose-6-phosphatase translocase levels in liver and kidney at both doses either alone or in combination with rosiglitazone. Rosiglitazone alone caused reductions in glucose-6-phosphatase translocase levels in liver.

Plasma glucose levels were evaluated at the beginning of the study (Wk 0), during the first week of treatment (Wk 1), during the third week of treatment (Wk 3), and during the fifth week of treatment (Wk 5).

TABLE 16

Plasma glucose levels of ZDF rats treated with antisense oligonucleotides targeting glucose-6-phosphatase translocase in combination with rosiglitazone

| Treatment | Plasma glucose (mg/dL) | | | |
|---|---|---|---|---|
| | Wk 0 | Wk 1 | Wk 3 | Wk 5 |
| Saline | 571 | 549 | 552 | 536 |
| ISIS 366228, 12.5 mg/kg | 570 | 549 | 547 | 532 |
| ISIS 366228, 25 mg/kg | 569 | 542 | 507 | 488 |
| Rosi + ISIS 366228, 12.5 mg/kg | 569 | 512 | 457 | 462 |
| Rosi + ISIS 366228, 25 mg/kg | 569 | 470 | 351 | 403 |
| Rosiglitazone | 570 | 462 | 487 | 498 |

As shown in Table 16, treatment with ISIS 366228 alone or rosiglitazone alone caused reductions in plasma glucose over the course of the study. However, in combination, ISIS 366228 and rosiglitazone were more effective in reducing glucose demonstrating an additive effect of the combination therapy. One embodiment of the present invention is a method of lowering glucose in an animal by administering an oligomeric compound targeting glucose-6-phosphatase translocase. Another embodiment of the present invention is a method of lowering glucose in an animal by administering an oligomeric compound targeting glucose-6-phosphatase translocase in combination with another glucose lowering-drug to achieve an additive therapeutic effect.

Food consumption was monitored throughout the study, and no changes in food consumption were observed for animals treated with ISIS 366228 in combination with rosiglitazone as compared to either treatment alone.

To further evaluate the effects of ISIS 366228 alone or in combination with rosiglitazone, oral glucose tolerance tests were performed during the third week of treatment. To provide a baseline glucose level, fasted blood glucose levels were measured before the challenge. Glucose was administered by oral gavage via an 18 gauge gavage needle at a dose of 1 g/kg. Plasma glucose levels were measured for 15, 30, 60, 90, and 120 minutes post-challenge, using a glucose analyzer (for example, an Ascencia Glucometer Elite XL, Bayer, Tarrytown, N.Y.). The results are presented in Table 17 as the average plasma glucose level (in mg/dL) for each treatment group at the indicated time point.

TABLE 17

Effects of antisense inhibition of glucose-6-phosphatase translocase alone or in combination with rosiglitazone: oral glucose tolerance test

| Treatment | Time post glucose-challenge (min.) | | | | | |
|---|---|---|---|---|---|---|
| | 0 | 15 | 30 | 60 | 90 | 120 |
| Saline | 283 | 424 | 507 | 460 | 427 | 430 |
| ISIS 366228, 12.5 mg/kg | 317 | 418 | 553 | 485 | 441 | 444 |
| ISIS 366228, 25 mg/kg | 303 | 453 | 540 | 461 | 427 | 408 |

TABLE 17-continued

Effects of antisense inhibition of glucose-6-phosphatase translocase alone or in combination with rosiglitazone: oral glucose tolerance test

| Treatment | Time post glucose-challenge (min.) | | | | | |
|---|---|---|---|---|---|---|
| | 0 | 15 | 30 | 60 | 90 | 120 |
| Rosi + ISIS 366228, 12.5 mg/kg | 215 | 399 | 519 | 403 | 400 | 366 |
| Rosi + ISIS 366228, 25 mg/kg | 172 | 345 | 474 | 355 | 332 | 296 |
| Rosiglitazone | 251 | 429 | 490 | 417 | 409 | 384 |

As shown in Table 17, animals treated with ISIS 366228 in combination with rosiglitazone displayed reduced fasting plasma glucose levels. Comparison of the area under the curves created by plotting the plasma glucose level as a function of time showed improved performance of animals treated with ISIS 366228 in combination with rosiglitazone as compared with animals treated with rosiglitazone alone or saline-treated controls.

Body weight was monitored throughout the study period. Average body weights at the indicated time points are presented in Table 18 (in grams) for each treatment group.

TABLE 18

Body weights of ZDF rats treated with ISIS 366228 alone or in combination with rosiglitazone

| Treatment | Body weight (g) | | | | |
|---|---|---|---|---|---|
| | Wk 0 | Wk 1 | Wk 2 | Wk 3 | Wk 4 |
| Saline | 414 | 413 | 420 | 422 | 423 |
| ISIS 366228, 12.5 mg/kg | 393 | 400 | 408 | 411 | 410 |
| ISIS 366228, 25 mg/kg | 406 | 405 | 419 | 425 | 419 |
| Rosi + ISIS 366228, 12.5 mg/kg | 402 | 419 | 441 | 453 | 463 |
| Rosi + ISIS 366228, 25 mg/kg | 401 | 430 | 456 | 473 | 485 |
| Rosiglitazone | 404 | 422 | 444 | 453 | 465 |

As shown in Table 18, treatment with rosiglitazone alone was associated with increased body weight and the combination of rosiglitazone with ISIS 366228 did not exacerbate the effect. Treatment with ISIS 366228 alone did not cause increased body weight.

Also monitored throughout the study was body composition. Baseline body composition was measured by MRI prior to the start of treatment (BL). Body composition was also measured during week 3 (Wk 3) and during week 5 (Wk 5) of treatment. Average percentage body fat determined for each treatment group at each time point is indicated in Table 19.

TABLE 19

Effect of combination treatment on body fat percentage in Zucker rats

| Treatment group | % Fat | | |
|---|---|---|---|
| | BL | Wk 3 | Wk 5 |
| Saline | 24 | 24 | 26 |
| ISIS 366228, 12.5 mg/kg | 25 | 26 | 27 |
| ISIS 366228, 25 mg/kg | 25 | 26 | 28 |
| Rosi + ISIS 366228, 12.5 mg/kg | 25 | 31 | 36 |

TABLE 19-continued

Effect of combination treatment on body fat percentage in Zucker rats

| Treatment group | % Fat | | |
|---|---|---|---|
| | BL | Wk 3 | Wk 5 |
| Rosi + ISIS 366228, 25 mg/kg | 25 | 32 | 37 |
| Rosiglitazone | 24 | 32 | 36 |

As shown in Table 19, treatment with ISIS 366228 alone did not cause marked increases in body fat percentage over the course of the study. Treatment with rosiglitazone alone resulted in increased body fat, but combination treatment with rosiglitazone and ISIS 366228 did not exacerbate the effect.

Tissue weights were also determined at the end of the study. Average kidney, spleen, liver, and fat pad weights are shown for each treatment group in Table 20 (in grams).

TABLE 20

Effect of combination therapy on tissue weights of ZDF rats

| Treatment group | Liver | Fat | Spleen | Kidney |
|---|---|---|---|---|
| Saline | 23 | 6 | 0.7 | 4 |
| ISIS 366228, 12.5 mg/kg | 26 | 7 | 1.0 | 4 |
| ISIS 366228, 25 mg/kg | 29 | 6 | 1.3 | 4 |
| Rosi + ISIS 366228, 12.5 mg/kg | 26 | 8 | 0.9 | 4 |
| Rosi + ISIS 366228, 25 mg/kg | 30 | 9 | 1.1 | 4 |
| Rosiglitazone | 21 | 9 | 0.6 | 4 |

As shown in Table 20, the renal enlargement associated with human glycogen storage disease type 1B is not observed as a result of inhibition of glucose-6-phosphatase translocase levels in ZDF rats with ISIS 366228.

To further assess the physiological effects resulting from inhibition of target mRNA with antisense oligonucleotide alone or in combination with rosiglitazone, the rats were evaluated throughout the treatment period for plasma free fatty acids, plasma cholesterol, and plasma triglyceride levels. Free fatty acids, triglycerides and cholesterol were measured by routine clinical analyzer instruments (e.g. Olympus Clinical Analyzer, Melville, N.Y.). Glucose levels were measured using a glucose analyzer, for example a YSI glucose analyzer (YSI Scientific, Yellow Springs, Ohio). Results are presented in Table 21 as the average level of plasma cholesterol (CHOL), or plasma triglycerides (TRIG) measured per treatment group.

TABLE 21

Effects of combination therapy on plasma lipids in ZDF rats

| Treatment group | CHOL (mg/dL) | | | | TRIG (mg/dL) | | | |
|---|---|---|---|---|---|---|---|---|
| | Wk 0 | Wk 1 | Wk 3 | Wk 5 | Wk 0 | Wk 1 | Wk 3 | Wk 5 |
| Saline | 203 | 220 | 243 | 246 | 543 | 451 | 516 | 494 |
| ISIS 366228, 12.5 mg/kg | 207 | 201 | 196 | 176 | 460 | 379 | 416 | 478 |
| ISIS 366228, 25 mg/kg | 210 | 196 | 206 | 183 | 470 | 307 | 354 | 472 |
| Rosi + ISIS 366228, 12.5 mg/kg | 216 | 200 | 204 | 205 | 540 | 344 | 342 | 482 |
| Rosi + ISIS 366228, 25 mg/kg | 223 | 197 | 219 | 262 | 576 | 251 | 315 | 590 |
| Rosiglitazone | 202 | 217 | 220 | 234 | 478 | 300 | 327 | 384 |

As shown in Table 21, all of the treatments caused initial decreases in plasma triglycerides. Treatment with ISIS 366228 alone prevented increases in plasma cholesterol observed for saline-treated control animals or animals treated with rosiglitazone alone.

The liver transaminases, ALT and AST, were measured throughout the study. Animals treated with rosiglitazone alone, ISIS 366228 alone, or with rosiglitazone in combination with ISIS 366228 showed reductions in levels of these indicators of liver function at week 5 of the study.

Because patients with human glycogen storage disease type 1b have mutations in the glucose-6-phosphatase translocase gene which manifest as defects in hepatic glycogen deposition, the ZDF rats were further evaluated at the end of the treatment period for alterations in liver glycogen stores. Tissue glycogen was measured using the Glucose Trinder reagent (Sigma-Aldrich, St. Louis, Mo.). None of the treatment groups showed substantial alterations in liver glycogen levels as compared to saline-treated control levels.

Example 15

Antisense Inhibition of Mouse Glucose-6-Phosphatase Translocase Expression by Oligomeric Compounds A series of oligomeric compounds was designed to target different regions of mouse glucose-6-phosphatase translocase, using published sequences cited in Table 1. The compounds are shown in Table 22. All compounds in Table 22 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the following primer-probe set designed to hybridize to mouse glucose-6-phosphatase translocase:

forward primer: GAAGGCAGGGCTGTCTCTGTAT (SEQ ID NO: 66)
reverse primer: CCATCCCAGCCATCATGAG (SEQ ID NO: 67)

and the PCR probe was: FAM-AACCCTCGCCACGGC-CTATTGC-TAMRA (SEQ ID NO: 68) where FAM is the fluorescent reporter dye and TAMRA is the quencher dye. Data are from experiments in which primary mouse hepatocytes were treated with 150 nM of the antisense oligonucleotides of the present invention using LIPOFECTIN™. A reduction in expression is expressed as percent inhibition in Table 22. If present, "N.D." indicates "not determined". The control oligomeric compound was SEQ ID NO: 11. The target regions to which these oligomeric compounds are inhibitory are herein referred to as "validated target segments."

TABLE 22

Inhibition of mouse glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 145647 | 3 | 50 | CTCTTGACTGCTCCTGCTTG | 52 | 205 |
| 145648 | 3 | 64 | CTTCTGACCACAGACTCTTG | 26 | 206 |
| 145649 | 3 | 77 | GCCCACTCCAGTACTTCTGA | 61 | 207 |
| 145650 | 3 | 92 | AAGCTGGCCCTGCTGGCCCA | 54 | 208 |
| 145651 | 3 | 99 | GTAGAAAAGCTGGCCCTGC | 31 | 209 |
| 145652 | 3 | 111 | TGGGCTGCCATGGTAGAAAA | 36 | 145 |
| 145653 | 3 | 112 | TTGGGCTGCCATGGTAGAAA | 42 | 210 |
| 145654 | 3 | 133 | AGTGCGATAGTAGCCGTAGC | 47 | 211 |
| 145655 | 3 | 153 | AACATGGCCGCAAATATGAC | 29 | 212 |
| 145656 | 3 | 171 | TACAGGCTGTAGCCTCCAAA | 47 | 213 |
| 145657 | 3 | 207 | GGCATGACAAAGGAGAAGGT | 45 | 146 |
| 145658 | 3 | 318 | TGGTCTGACAGAACCCCGCT | 36 | 214 |
| 145659 | 3 | 326 | CGCTCATCTGGTCTGACAGA | 15 | 215 |
| 145660 | 3 | 397 | TGTGGAGCTCCATGAGAAGA | 40 | 216 |
| 145661 | 3 | 422 | ACCAAGGAGCAGCAAAGGCT | 25 | 217 |
| 145662 | 3 | 516 | GCCCACCAAGTGCCAAACTG | 19 | 147 |
| 145663 | 3 | 527 | TTGACAACACAGCCCACCAA | 48 | 218 |
| 145664 | 3 | 541 | CAGGTTCATGCTGGTTGACA | 50 | 148 |
| 145665 | 3 | 546 | CCAGCCAGGTTCATGCTGGT | 22 | 219 |
| 145666 | 3 | 564 | AAGATAGGTCCCAAACTTCC | 28 | 220 |
| 145667 | 3 | 597 | CGCCAGCTGTAGCTCTGGGC | 49 | 149 |
| 145668 | 3 | 600 | CTGCGCCAGCTGTAGCTCTG | 39 | 150 |
| 145669 | 3 | 627 | CACAGTGCCCCAGACAGGGC | 9 | 221 |
| 145670 | 3 | 633 | ACCACACACAGTGCCCCAGA | 45 | 151 |
| 145671 | 3 | 640 | GGAGACAACCACACACAGTG | 25 | 152 |
| 145672 | 3 | 665 | TGTGGATGAGCAGCAGACAG | 8 | 222 |
| 145673 | 3 | 672 | GGTTCATTGTGGATGAGCAG | 4 | 153 |
| 145674 | 3 | 677 | CAGCAGGTTCATTGTGGATG | 43 | 223 |
| 145675 | 3 | 682 | AACATCAGCAGGTTCATTGT | 23 | 224 |
| 145676 | 3 | 687 | AGTCCAACATCAGCAGGTTC | 51 | 25 |
| 145677 | 3 | 724 | CTTCTTGCCCTCAGAGGGCA | 9 | 225 |
| 145678 | 3 | 729 | GAGCCCTTCTTGCCCTCAGA | 60 | 226 |
| 145679 | 3 | 734 | TCAAGGAGCCCTTCTTGCCC | 17 | 227 |
| 145680 | 3 | 739 | CTCCTTCAAGGAGCCCTTCT | 0 | 228 |
| 145681 | 3 | 744 | CTCTCCTCCTTCAAGGAGCC | 36 | 229 |
| 145682 | 3 | 749 | GGGTGCTCTCCTCCTTCAAG | 31 | 230 |

TABLE 22-continued

Inhibition of mouse glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 145683 | 3 | 760 | CAGCTCCTGTAGGGTGCTCT | 0 | 231 |
| 145684 | 3 | 821 | TCTTTACTCCGAAGACCACA | 43 | 232 |
| 145685 | 3 | 852 | AGGAAGAACTGGCCCCAGTC | 43 | 154 |
| 145686 | 3 | 857 | GGATAAGGAAGAACTGGCCC | 26 | 155 |
| 145687 | 3 | 862 | CTCCTGGATAAGGAAGAACT | 12 | 233 |
| 145688 | 3 | 872 | ACTGCCCTCTCCTGGATA | 25 | 234 |
| 145689 | 3 | 881 | CAAGGGCGGACTGCCCTCTC | 34 | 235 |
| 145690 | 3 | 917 | CTCCGACCTCGAGGGCACTG | 56 | 236 |
| 145691 | 3 | 956 | TGTCTGACAGGTAACCAGCT | 30 | 237 |
| 145692 | 3 | 1038 | GCTGCCATCCCAGCCATCAT | 65 | 238 |
| 145693 | 3 | 1055 | GGAAGAGATACGTGGATGCT | 0 | 239 |
| 145694 | 3 | 1076 | AGTCACTGGTCACCGTTACT | 23 | 240 |
| 145695 | 3 | 1139 | CAATGGGACCATAAGAAGAG | 24 | 241 |
| 145696 | 3 | 1151 | CTCCAAACAAGGCAATGGGA | 37 | 242 |
| 145697 | 3 | 1160 | TGGCTATGACTCCAAACAAG | 45 | 243 |
| 145698 | 3 | 1208 | CCACAATAGCATGAGAGGTT | 33 | 244 |
| 145699 | 3 | 1231 | TCCACCCACATTGGCCATAA | 41 | 245 |
| 145700 | 3 | 1266 | TTGGCAATGGTGCTGAAGGG | 1 | 156 |
| 145701 | 3 | 1271 | AGTGCTTGGCAATGGTGCTG | 54 | 246 |
| 145702 | 3 | 1296 | ACCCAGAAGGCTGTGCTCCA | 45 | 157 |
| 145703 | 3 | 1308 | ACCACTTCTGCCACCCAGAA | 42 | 247 |
| 145704 | 3 | 1321 | GCTGGCTCCACAAACCACTT | 54 | 248 |
| 145705 | 3 | 1360 | CTTGGTGCGGATATTTCGAA | 49 | 249 |
| 145706 | 3 | 1368 | CGGCCCATCTTGGTGCGGAT | 54 | 158 |
| 145707 | 3 | 1376 | TGGATACTCGGCCCATCTTG | 56 | 250 |
| 145708 | 3 | 1399 | GGACTCGATTCACTCTCCCT | 48 | 251 |
| 145709 | 3 | 1416 | GGGATGCTCCATAGCGAGGA | 14 | 252 |
| 145710 | 3 | 1438 | CCTGCCAGTAAGGCTGCAGT | 13 | 253 |
| 145711 | 3 | 1507 | GAGAGACAGTGGAGACACAG | 33 | 254 |
| 145712 | 3 | 1517 | TGGAGGTTCAGAGAGACAGT | 42 | 255 |
| 145713 | 3 | 1533 | GTAACTTGCAGCACCATGGA | 63 | 256 |
| 145714 | 3 | 1540 | GCCACTGGTAACTTGCAGCA | 66 | 257 |
| 145715 | 3 | 1644 | AGGAGTTGCCTGTCTGCCAG | 50 | 258 |
| 145716 | 3 | 1654 | CCCTGAATTCAGGAGTTGCC | 52 | 259 |
| 145717 | 3 | 1704 | TACTCACTAGGAGATCAGGA | 52 | 260 |
| 145718 | 3 | 1760 | CAATTTTGCCCCCTGCCAAG | 26 | 261 |

TABLE 22-continued

Inhibition of mouse glucose-6-phosphatase translocase mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 145719 | 3 | 1805 | GAGTGGTGGACTCCTCTCCT | 47 | 262 |
| 145720 | 3 | 1882 | TCAAATCTAGCTITATTCGA | 11 | 263 |
| 145721 | 204 | 2 | GGCTGTGGGTCCCCGAACGA | 0 | 264 |
| 145722 | 204 | 41 | CAGTGTCCCTGCGACATCAG | 8 | 265 |
| 145723 | 204 | 87 | GCCGCCTTCTGGACAATCAT | 0 | 266 |
| 145724 | 204 | 98 | GGCTCTTTATAGCCGCCTTC | 0 | 267 |
| 371389 | 3 | 77 | GCCCACTCCAGTACTTCTGA | N.D. | 268 |

Example 16

Oligomeric Compounds Designed to Target Rat Glucose-6-Phosphatase Translocase A series of oligomeric compounds was designed to target different regions of mouse glucose-6-phosphatase translocase, using published sequences cited in Table 1. The compounds are shown in Table 23. All compounds in Table 23 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines.

TABLE 23

Chimeric oligonucleotides having 2'-MOE wings and deoxy gap targeted to ratglucose-6-phosphatase translocase mRNA

| ISIS # | Target SEQ ID NO | Target Site | Sequence (5' to 3') | SEQ ID NO |
|---|---|---|---|---|
| 349094 | 4 | 4 | CGGATCTGCTGAGCTGTGTT | 269 |
| 349095 | 4 | 19 | TCCCTCTCCAGTGCCCGGAT | 270 |
| 349096 | 4 | 32 | TCCTGCTTGCAGCTCCCTCT | 271 |
| 349097 | 4 | 47 | CACACTCTTGACTGCTCCTG | 272 |
| 349098 | 4 | 62 | CACGGTGCTTCTGACCACAC | 273 |
| 349099 | 4 | 70 | GGTCCACTCACGGTGCTTCT | 274 |
| 349100 | 4 | 97 | GCCATGGTAGAAAAAGCCGG | 275 |
| 349101 | 4 | 111 | CATAGCCTTGGGCCGCCATG | 276 |
| 349102 | 4 | 130 | ATGACAGTGCGGTAATAGCC | 277 |
| 349103 | 4 | 144 | ACATGGCTGTGAATATGACA | 278 |
| 349104 | 4 | 163 | TAAAGGCTGTAGCCTCCGAA | 279 |
| 349105 | 4 | 176 | GCGGTTGAAGTAGTAAAGGC | 280 |
| 349106 | 4 | 196 | ATGACAAAAGAGAAGGTTTT | 281 |
| 349107 | 4 | 209 | CACCAAGGAGGGCATGACAA | 282 |
| 349108 | 4 | 228 | TGTCCAGAGCGATCTCATCC | 283 |
| 349109 | 4 | 242 | CCCCAAATCGTCCTTGTCCA | 284 |
| 349110 | 4 | 260 | CTGGCTGCTCGTGATGAGCC | 285 |
| 349111 | 4 | 278 | GATGGCGTAGGCTGCCGACT | 286 |
| 349112 | 4 | 326 | CCAACGGGCACTCATCTGAT | 287 |
| 349113 | 4 | 359 | CAGACCAACCAGGAGCAGCC | 288 |
| 349114 | 4 | 392 | TACTGTAGAGCTCCACGAGA | 289 |
| 349115 | 4 | 427 | AGACCATTAAGAAACCAGAG | 290 |
| 349116 | 4 | 473 | CTTCCTCAGGATCTTCCCAC | 291 |
| 349117 | 4 | 507 | CCCACCAAGTACCAAACTGG | 292 |
| 349118 | 4 | 569 | AAGGATTGTCGCCAAGATAG | 293 |
| 349119 | 4 | 600 | CCAGGGTGCTGCGCCAGCTG | 294 |
| 349120 | 4 | 662 | TTCGTTGTGGATGAGCAGGA | 295 |
| 349121 | 4 | 693 | GGTCCAGATTTCGGAGTCCA | 296 |
| 349122 | 4 | 742 | AGGGTGCTCTCCTCCTTTGA | 297 |
| 349123 | 4 | 788 | GCCAGTGGAGAGCACCCAGA | 298 |
| 349124 | 4 | 822 | TACAGCAAGTCTTTACCCCA | 299 |
| 349125 | 4 | 852 | CCTGGATAAGGAAGAACTGG | 300 |
| 349126 | 4 | 883 | GAACTACCCACAAGGGCCGA | 301 |
| 349127 | 4 | 912 | GGCCTCCAACCTCTAGGGCA | 302 |
| 349128 | 4 | 943 | GACAGATAGCCAGCTGCAAT | 303 |

TABLE 23-continued

Chimeric oligonucleotides having 2'-MOE wings and deoxy gap targeted to ratglucose-6-phosphatase translocase mRNA

| ISIS # | Target SEQ ID NO | Target Site | Sequence (5' to 3') | SEQ ID NO |
|---|---|---|---|---|
| 349129 | 4 | 975 | CAGACAGCCCTGCCTTTGCC | 304 |
| 349130 | 4 | 1003 | AACAGGCTGTGGCGAGGGTT | 305 |
| 349131 | 4 | 1035 | TGGATGCTGCCATGCCAGCC | 306 |
| 349132 | 4 | 1067 | GTCGCTGGTCACTGTTACCC | 307 |
| 349133 | 4 | 1099 | GCTCCCAATACCAGGATCCA | 308 |
| 349134 | 4 | 1130 | AATGGGACCATAAGAAGAGA | 309 |
| 349135 | 4 | 1156 | TCATTAGCTATGACTCCAAA | 310 |
| 349136 | 4 | 1188 | GAGAGGTACCACACAAGTTG | 311 |
| 349137 | 4 | 1219 | CCCACATTGGCCATGAGCCC | 312 |
| 349138 | 4 | 1249 | GTACTGAAGGGTAACCCAGC | 313 |
| 349139 | 4 | 1281 | AGGCTGTGCTCCAGCTATAG | 314 |
| 349140 | 4 | 1312 | CTGGCTATACAGATCACTTC | 315 |
| 349141 | 4 | 1342 | ATATTTCGAAGCAAGAAGAA | 316 |
| 349142 | 4 | 1375 | GCCTTCTTGGATACTCGGCC | 317 |
| 349143 | 4 | 1405 | ATGCTCTATAGTGAGTGCTC | 318 |
| 349144 | 4 | 1453 | GCAGCCTCTCTTCCTTTCTG | 319 |
| 349145 | 4 | 1484 | ACAGATATGTAAAGGCTCTG | 320 |
| 349146 | 4 | 1515 | CACCACGGAGGTCCAGAGAG | 321 |
| 349147 | 4 | 1544 | GGACCTCATTAGCCACTGGT | 322 |
| 349148 | 4 | 1576 | CCTAAAACCAAACATCATTT | 323 |
| 349149 | 4 | 1609 | TCTGCTAGAAGGTAGAAACA | 324 |
| 349150 | 4 | 1638 | GGAGACACCCTGAATTTAGG | 325 |
| 349151 | 4 | 1702 | TGCAGCTGCAGAGATAGAAC | 326 |
| 349152 | 4 | 1733 | GTACAGCAGAAACCACAGGC | 327 |
| 349153 | 4 | 1782 | GGGACTGAGGTATTGGCAAC | 328 |
| 349154 | 4 | 1812 | ATGAGAGTGGTGGCCTCCTC | 329 |
| 349155 | 4 | 1844 | CTACATTCCTCCCTTTTGTC | 330 |
| 349156 | 4 | 1858 | AGACAGTTTGCTCTCTACAT | 331 |
| 349157 | 4 | 1860 | CAAGACAGTTTGCTCTCTAC | 332 |
| 349158 | 4 | 1862 | TACAAGACAGTTTGCTCTCT | 333 |
| 349159 | 4 | 1864 | TATACAAGACAGTTTGCTCT | 334 |
| 349160 | 4 | 1866 | TCTATACAAGACAGTTTGCT | 335 |
| 349161 | 4 | 1868 | AGTCTATACAAGACAGTTTG | 336 |
| 349162 | 4 | 1870 | TTAGTCTATACAAGACAGTT | 337 |
| 349163 | 4 | 1893 | TTTTAGTATCAAATCTAGTT | 338 |

What is claimed:

1. A method of lowering glucose levels in an animal, comprising administering to the animal a therapeutically effective amount of a glucose-6-phosphatase translocase specific inhibitor, wherein the inhibitor is a nucleic acid and the glucose levels are reduced in the animal.

2. A method of lowering triglycerides levels in an animal, comprising administering to the animal a therapeutically effective amount of a glucose-6-phosphatase translocase specific inhibitor, wherein the inhibitor is a nucleic acid and the triglyceride levels are reduced in the animal.

3. A method of lowering cholesterol in an animal, comprising administering to the animal a therapeutically effective amount of a glucose-6-phosphatase translocase specific inhibitor, wherein the inhibitor is a nucleic acid and the cholesterol is reduced in the animal.

4. The method of claim 2, wherein the triglycerides are circulating triglycerides.

5. The method of claim 1, wherein the glucose is blood glucose.

6. The method of claims 1-3, wherein the animal is need of such treatment.

7. The method of claims 1-3, wherein said animal has condition selected from diabetes, type II diabetes, insulin resistance, insulin deficiency, hypercholesterolemia, hyperglycemia, hyperlipidemia, hypertriglyceridemia, hyperfattyacidemia, liver steatosis, metabolic syndrome, cardiovascular disease, or a cardiovascular risk factor.

8. The method of claim 7, wherein said animal has a condition associated with metabolic syndrome.

9. The method of claims 1-3, wherein the nucleic acid is a modified oligonucleotide.

10. The method of claim 9, wherein the modified oligonucleotide consists of 13 to 80 linked nucleosides.

11. The method of claim 9, wherein the modified oligonucleotide consists of 13 to 50 linked nucleosides.

12. The method of claim 9, wherein the modified oligonucleotide consists of 13 to 30 linked nucleosides.

13. The method of claim 9, wherein the modified oligonucleotide is a single-stranded oligonucleotide.

14. The method of claim 13, wherein the modified oligonucleotide has a nucleobase sequence that is 90% complementary to a human glucose-6-phosphatase translocase.

15. The method of claim 13, wherein the modified oligonucleotide has a nucleobase sequence that is 95% complementary to a human glucose-6-phosphatase translocase.

16. The method of claim 13, wherein the modified oligonucleotide has a nucleobase sequence that is 99% complementary to a human glucose-6-phosphatase translocase.

17. The method of claim 13, wherein the modified oligonucleotide has a nucleobase sequence that is 100% complementary to a human glucose-6-phosphatase translocase.

18. The method of claim 9, wherein the modified oligonucleotide comprises at least one modified internucleoside linkage.

19. The method of claim 18, wherein the at least one modified internucleoside linkage is a phosphorothioate internucleoside linkage.

20. The method of claim 9, wherein at least one nucleoside of the modified oligonucleotide comprises a modified sugar.

21. The method of claim 20, wherein the modified sugar is a bicyclic sugar.

22. The method of claim 20, wherein the modified sugar comprises a 2'-O-methoxyethyl group.

23. The method of claim 9, wherein at least one nucleoside of the modified oligonucleotide comprises a modified nucleobase.

24. The method of claim 23, wherein the modified nucleobase is a 5-methylcytosine.

25. The method of claim 9, wherein the modified oligonucleotide comprises:
   a gap segment consisting of linked deoxy nucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

26. The method of claim 9, further comprising the step of administering at least one additional glucose-lowering drug.

27. The method of claim 26 wherein the glucose-lowering drug is a hormone, a hormone mimetic, a sulfonylurea, a biguanide, a meglitinide, a thiazolidinedione, an alpha glucosidase inhibitor, or an antisense compound not targeted to glucose-6-phosphatase translocase.

28. The method of claim 27 wherein the hormone or hormone mimetic is insulin, GLP-1 or a GLP-1 analog.

29. The method of claim 28 wherein the GLP-1 analog is exendin-4 or liraglutide.

30. The method of claim 27 wherein the sulfonylurea is acetohexamide, chlorpropamide, tolbutamide, tolazamide, glimepiride, a glipizide, glyburide or a gliclazide.

31. The method of claim 27 wherein the biguanide is metformin.

32. The method of claim 27 wherein the meglitinide is nateglinide or repaglinide.

33. The method of claim 27 wherein the thiazolidinedione is pioglitazone, rosiglitazone or troglitazone.

34. The method of claim 27 wherein the alpha-glucosidase inhibitor is acarbose or miglitol.

* * * * *